(12) United States Patent
Thiel et al.

(10) Patent No.: US 12,304,900 B2
(45) Date of Patent: May 20, 2025

(54) ISLET CELL MANUFACTURING COMPOSITIONS AND METHODS OF USE

(71) Applicant: Vertex Pharmaceuticals Incorporated, Boston, MA (US)

(72) Inventors: Austin Thiel, Southborough, MA (US); Jihad Yasin, Gardner, MA (US); Evrett Thompson, Wobum, MA (US); Felicia J. Pagliuca, Boston, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 18/581,700

(22) Filed: Feb. 20, 2024

(65) Prior Publication Data
US 2024/0294501 A1 Sep. 5, 2024

Related U.S. Application Data

(60) Division of application No. 16/864,886, filed on May 1, 2020, now Pat. No. 11,945,795, which is a continuation of application No. PCT/US2018/061364, filed on Nov. 15, 2018.

(60) Provisional application No. 62/669,170, filed on May 9, 2018, provisional application No. 62/586,808, filed on Nov. 15, 2017.

(51) Int. Cl.
| C07D 401/14 | (2006.01) |
| C07D 401/04 | (2006.01) |
| C07K 14/495 | (2006.01) |
| C07K 14/50 | (2006.01) |
| C12N 5/071 | (2010.01) |

(52) U.S. Cl.
CPC ......... *C07D 401/14* (2013.01); *C07D 401/04* (2013.01); *C07K 14/495* (2013.01); *C07K 14/50* (2013.01); *C12N 5/0676* (2013.01); *C12N 2501/117* (2013.01); *C12N 2501/155* (2013.01); *C12N 2501/16* (2013.01); *C12N 2501/385* (2013.01); *C12N 2501/41* (2013.01)

(58) Field of Classification Search
None
See application file for complete search history.

(56) References Cited

U.S. PATENT DOCUMENTS

| | | |
|---|---|---|
| 4,378,016 A | 3/1983 | Loeb |
| 4,391,909 A | 7/1983 | Lim |
| 5,674,289 A | 10/1997 | Fournier et al. |
| 5,843,780 A | 12/1998 | Thomson |
| 6,090,622 A | 7/2000 | Gearhart et al. |
| 6,200,806 B1 | 3/2001 | Thomson |
| 6,436,704 B1 | 8/2002 | Roberts et al. |
| 6,667,176 B1 | 12/2003 | Funk et al. |
| 6,800,480 B1 | 10/2004 | Bodnar et al. |
| 7,029,913 B2 | 4/2006 | Thomson |
| 7,033,831 B2 | 4/2006 | Fisk et al. |
| 7,153,684 B1 | 12/2006 | Hogan |
| 7,157,278 B2 | 1/2007 | Jin |
| 7,163,918 B2 | 1/2007 | Piccariello et al. |
| 7,297,539 B2 | 11/2007 | Mandalam et al. |
| 7,326,572 B2 | 2/2008 | Fisk et al. |
| 7,410,798 B2 | 8/2008 | Mandalam et al. |
| 7,432,104 B2 | 10/2008 | Mitalipova et al. |
| 7,510,876 B2 | 3/2009 | Kevin |
| 7,534,608 B2 | 5/2009 | Martinson et al. |
| 7,541,185 B2 | 6/2009 | Kevin |
| 7,625,753 B2 | 12/2009 | Kelly et al. |
| 7,695,963 B2 | 4/2010 | Agulnick et al. |
| 7,695,965 B2 | 4/2010 | Martinson et al. |
| 7,704,738 B2 | 4/2010 | Kevin |
| 7,964,402 B2 | 6/2011 | Terskikh et al. |
| 7,985,585 B2 | 7/2011 | Kevin |
| 7,993,916 B2 | 8/2011 | Agulnick et al. |
| 7,993,920 B2 | 8/2011 | Martinson et al. |
| 8,008,075 B2 | 8/2011 | Green et al. |
| 8,129,182 B2 | 3/2012 | Kevin |
| 8,153,429 B2 | 4/2012 | Robins et al. |
| 8,187,878 B2 | 5/2012 | Dalton et al. |
| 8,211,699 B2 | 7/2012 | Robins et al. |
| 8,216,836 B2 | 7/2012 | Kevin |
| 8,278,106 B2 | 10/2012 | Martinson et al. |
| 8,334,138 B2 | 12/2012 | Robins et al. |
| 8,338,170 B2 | 12/2012 | Kelly et al. |
| 8,415,153 B2 | 4/2013 | Majumdar et al. |
| 8,445,273 B2 | 5/2013 | Green et al. |
| 8,603,811 B2 | 12/2013 | Kevin |
| 8,623,645 B2 | 1/2014 | Kevin |
| 8,647,873 B2 | 2/2014 | Kevin |

(Continued)

FOREIGN PATENT DOCUMENTS

| CN | 105349517 A | 2/2016 |
| CN | 106414718 A | 2/2017 |

(Continued)

OTHER PUBLICATIONS

Rezania, et al., Enrichment of Human Embryonic Stem Cell-Derived NKX6.1—Expressing Pancreatic Progenitor Cells Accelerates the Maturation of InsulinSecretin Cells in Vivo, Stem Cells, 31 (2013): 2432-2442.

(Continued)

*Primary Examiner* — David W Berke-Schlessel
(74) *Attorney, Agent, or Firm* — Klarquist Sparkman, LLP

(57) ABSTRACT

Disclosed herein are compositions and methods useful for manufacturing SC-β cell, and isolated populations of SC-β cells for use in various applications, such as cell therapy.

24 Claims, 18 Drawing Sheets

Specification includes a Sequence Listing.

(56) References Cited

U.S. PATENT DOCUMENTS

| | | |
|---|---|---|
| 8,658,151 B2 | 2/2014 | Kelly et al. |
| 8,785,184 B2 | 7/2014 | Xu |
| 8,785,185 B2 | 7/2014 | Xu et al. |
| 8,859,286 B2 | 10/2014 | Agulnick |
| 9,096,832 B2 | 8/2015 | Xu |
| 9,109,245 B2 | 8/2015 | Agulnick et al. |
| 9,186,381 B2 | 11/2015 | Zender et al. |
| 9,650,610 B2 | 5/2017 | Agulnick |
| 9,974,784 B2 | 5/2018 | Groppe |
| 10,030,229 B2 | 7/2018 | Peterson et al. |
| 10,138,465 B2 | 11/2018 | Rezania |
| 10,190,096 B2 | 1/2019 | Melton et al. |
| 10,253,298 B2 | 4/2019 | Melton et al. |
| 10,443,042 B2 | 10/2019 | Melton et al. |
| 10,655,106 B2 | 5/2020 | Peterson et al. |
| 2001/0049130 A1 | 12/2001 | Spielberg |
| 2002/0094569 A1 | 7/2002 | Yu et al. |
| 2003/0138948 A1 | 7/2003 | Fisk et al. |
| 2004/0047837 A1 | 3/2004 | Fong et al. |
| 2004/0121460 A1 | 6/2004 | Lumelsky et al. |
| 2004/0191901 A1 | 9/2004 | Assady et al. |
| 2004/0259244 A1 | 12/2004 | Scharp et al. |
| 2005/0053588 A1 | 3/2005 | Yin |
| 2006/0040385 A1 | 2/2006 | Itskovitz-Eldor et al. |
| 2006/0040387 A1 | 2/2006 | Fisk et al. |
| 2006/0194321 A1 | 8/2006 | Colman et al. |
| 2007/0142376 A1 | 6/2007 | Fleenor et al. |
| 2008/0145889 A1 | 6/2008 | Fisk et al. |
| 2008/0299582 A1 | 12/2008 | Mandalam et al. |
| 2009/0047263 A1 | 2/2009 | Yamanaka et al. |
| 2009/0068742 A1 | 3/2009 | Yamanaka |
| 2009/0170198 A1 | 7/2009 | Rezania |
| 2009/0186076 A1 | 7/2009 | Kataoka et al. |
| 2009/0191159 A1 | 7/2009 | Sakurada et al. |
| 2009/0227032 A1 | 9/2009 | Yamanaka et al. |
| 2009/0246875 A1 | 10/2009 | Yamanaka et al. |
| 2009/0263896 A1 | 10/2009 | Kelly et al. |
| 2009/0298178 A1 | 12/2009 | Kevin |
| 2009/0304646 A1 | 12/2009 | Sakurada et al. |
| 2009/0325180 A1 | 12/2009 | Fisk et al. |
| 2010/0015100 A1 | 1/2010 | Xu |
| 2010/0015711 A1 | 1/2010 | Davis et al. |
| 2010/0112693 A1 | 5/2010 | Rezania et al. |
| 2010/0144033 A1 | 6/2010 | Mandalam et al. |
| 2010/0240130 A1 | 9/2010 | Majumdar et al. |
| 2010/0255580 A1 | 10/2010 | Rezania |
| 2010/0260728 A1 | 10/2010 | Martinson et al. |
| 2010/0267731 A1 | 10/2010 | Nakamura |
| 2010/0311166 A1 | 12/2010 | Florio et al. |
| 2011/0008819 A1 | 1/2011 | Chipperfield et al. |
| 2011/0014702 A1 | 1/2011 | Xu |
| 2011/0053930 A1 | 3/2011 | Yu et al. |
| 2011/0151560 A1 | 6/2011 | Xu |
| 2011/0280842 A1 | 11/2011 | Melton et al. |
| 2011/0281355 A1 | 11/2011 | Xu |
| 2011/0305672 A1 | 12/2011 | Dalton et al. |
| 2012/0009675 A1 | 1/2012 | Martinson et al. |
| 2012/0021519 A1 | 1/2012 | Ichida et al. |
| 2012/0052571 A1 | 3/2012 | Fryer |
| 2012/0052575 A1 | 3/2012 | Rezania |
| 2012/0052576 A1 | 3/2012 | Rezania |
| 2012/0135015 A1 | 5/2012 | Noguchi et al. |
| 2012/0141436 A1 | 6/2012 | Bonner-Weir et al. |
| 2013/0034526 A1 | 2/2013 | Itskovitz-Eldor et al. |
| 2013/0071931 A1 | 3/2013 | Ishikawa |
| 2013/0189777 A1 | 7/2013 | Rezania |
| 2013/0316357 A1 | 11/2013 | Kevin |
| 2013/0330823 A1 | 12/2013 | Rezania |
| 2013/0337564 A1 | 12/2013 | Davis et al. |
| 2014/0029704 A1 | 1/2014 | Becker |
| 2014/0080210 A1 | 3/2014 | Davis et al. |
| 2014/0134726 A1 | 5/2014 | Kevin |
| 2014/0154801 A1 | 6/2014 | Kevin |
| 2014/0154802 A1 | 6/2014 | Robins et al. |
| 2014/0162359 A1 | 6/2014 | Rezania |
| 2014/0186305 A1 | 7/2014 | Rezina |
| 2014/0186948 A1 | 7/2014 | Schulz et al. |
| 2014/0186953 A1 | 7/2014 | Rezania |
| 2014/0193902 A1 | 7/2014 | Kevin |
| 2014/0193904 A1 | 7/2014 | Kevin |
| 2014/0242693 A1 | 8/2014 | Fryer et al. |
| 2014/0271566 A1 | 9/2014 | Agulnick |
| 2014/0287944 A1 | 9/2014 | Hrvatin et al. |
| 2014/0329704 A1 | 11/2014 | Melton et al. |
| 2014/0335611 A1 | 11/2014 | Chen et al. |
| 2015/0017135 A1 | 1/2015 | Agulnick |
| 2015/0104430 A1 | 4/2015 | Keller et al. |
| 2015/0218522 A1 | 8/2015 | Peterson et al. |
| 2015/0240212 A1 | 8/2015 | Peterson et al. |
| 2015/0247123 A1 | 9/2015 | Ekberg et al. |
| 2015/0329828 A1 | 11/2015 | Rezania |
| 2015/0376574 A1 | 12/2015 | Talavera-Adame et al. |
| 2016/0022742 A1 | 1/2016 | Zender et al. |
| 2016/0040130 A1 | 2/2016 | Rezania |
| 2016/0115167 A1 | 4/2016 | Yu et al. |
| 2016/0175363 A1* | 6/2016 | Melton ............... A61K 38/28 435/1.1 |
| 2016/0177267 A1 | 6/2016 | Melton et al. |
| 2016/0177268 A1 | 6/2016 | Melton et al. |
| 2016/0177269 A1 | 6/2016 | Melton et al. |
| 2016/0186143 A1 | 6/2016 | Melton et al. |
| 2016/0208215 A1 | 7/2016 | Doehn et al. |
| 2016/0326495 A1 | 11/2016 | Ekberg et al. |
| 2016/0369239 A1 | 12/2016 | Agulnick et al. |
| 2017/0029778 A1 | 2/2017 | Peterson et al. |
| 2017/0233700 A1 | 8/2017 | Kunisada |
| 2017/0240866 A1 | 8/2017 | Wells et al. |
| 2017/0349884 A1 | 12/2017 | Karp et al. |
| 2017/0362572 A1 | 12/2017 | Rieck et al. |
| 2018/0153941 A1 | 6/2018 | Melton et al. |
| 2018/0179593 A1 | 6/2018 | Melton et al. |
| 2019/0017031 A1 | 1/2019 | Peterson et al. |
| 2019/0085295 A1 | 3/2019 | Christophersen et al. |
| 2019/0119649 A1 | 4/2019 | Melton et al. |
| 2019/0185817 A1 | 6/2019 | Melton et al. |
| 2019/0338250 A1 | 11/2019 | Melton et al. |
| 2020/0199539 A1 | 6/2020 | Melton et al. |
| 2020/0332262 A1 | 10/2020 | Poh et al. |
| 2020/0347355 A1 | 11/2020 | Melton et al. |
| 2020/0347356 A1 | 11/2020 | Melton et al. |
| 2020/0347357 A1 | 11/2020 | Melton et al. |
| 2020/0347358 A1 | 11/2020 | Peterson et al. |
| 2020/0385681 A1 | 12/2020 | Peterson et al. |
| 2021/0198632 A1 | 7/2021 | Pagliuca et al. |
| 2021/0198633 A1 | 7/2021 | Nostro et al. |
| 2021/0238553 A1 | 8/2021 | Pagliuca et al. |
| 2021/0403875 A1 | 12/2021 | Pagliuca et al. |
| 2021/0403876 A1 | 12/2021 | Pagliuca et al. |

FOREIGN PATENT DOCUMENTS

| | | |
|---|---|---|
| EP | 1456356 A2 | 9/2004 |
| EP | 1676574 A2 | 7/2006 |
| EP | 2267116 A1 | 12/2010 |
| EP | 2292734 A1 | 3/2011 |
| EP | 2341147 A2 | 7/2011 |
| EP | 2377922 A2 | 10/2011 |
| EP | 2569419 A2 | 3/2013 |
| EP | 2283117 B1 | 10/2013 |
| EP | 2650359 A1 | 10/2013 |
| EP | 2650360 A2 | 10/2013 |
| EP | 2664669 A1 | 11/2013 |
| EP | 2674485 A1 | 12/2013 |
| EP | 2970899 A1 | 1/2016 |
| JP | H11505411 A | 5/1999 |
| JP | 2006506047 A | 2/2006 |
| JP | 2016503654 A | 2/2016 |
| JP | 2016506246 A | 3/2016 |
| RU | 2011121843 A | 12/2012 |
| WO | 1996031242 A1 | 10/1996 |
| WO | 9920741 A1 | 4/1999 |
| WO | 1999020740 A2 | 4/1999 |
| WO | 2001051616 A2 | 7/2001 |
| WO | 2001088104 A2 | 11/2001 |

(56) References Cited

FOREIGN PATENT DOCUMENTS

| | | | |
|---|---|---|---|
| WO | 2002042445 A2 | 5/2002 | |
| WO | 03020920 A1 | 3/2003 | |
| WO | 2003050249 A2 | 6/2003 | |
| WO | 2003100026 A2 | 12/2003 | |
| WO | 2004058764 A1 | 7/2004 | |
| WO | 2007002136 A2 | 1/2007 | |
| WO | 2007075807 A2 | 7/2007 | |
| WO | 2007103282 A2 | 9/2007 | |
| WO | 2007127927 A2 | 11/2007 | |
| WO | 2008083331 A2 | 7/2008 | |
| WO | 2008102000 A1 | 8/2008 | |
| WO | 2009012428 A2 | 1/2009 | |
| WO | 2009018453 A1 | 2/2009 | |
| WO | 2009070592 A2 | 6/2009 | |
| WO | 2010057039 A2 | 5/2010 | |
| WO | 2010059778 A1 | 5/2010 | |
| WO | 2011059725 A2 | 5/2011 | |
| WO | 2011079017 A2 | 6/2011 | |
| WO | 2011109279 A2 | 9/2011 | |
| WO | 2011123572 A1 | 10/2011 | |
| WO | 2011139628 A1 | 11/2011 | |
| WO | 2011143299 A1 | 11/2011 | |
| WO | 2012020845 A1 | 2/2012 | |
| WO | 2012021698 A2 | 2/2012 | |
| WO | 2012025725 A1 | 3/2012 | |
| WO | 2012030540 A2 | 3/2012 | |
| WO | 2012168930 A2 | 12/2012 | |
| WO | 2013057164 A1 | 4/2013 | |
| WO | 2013095953 A1 | 6/2013 | |
| WO | 2014033322 A1 | 3/2014 | |
| WO | 2014062138 A1 | 4/2014 | |
| WO | 2014105543 A1 | 7/2014 | |
| WO | 2014105546 A1 | 7/2014 | |
| WO | 2014106141 A1 | 7/2014 | |
| WO | WO-2014/106141 | 7/2014 | |
| WO | 2014151871 A2 | 9/2014 | |
| WO | 2014160413 A1 | 10/2014 | |
| WO | 2014201167 A1 | 12/2014 | |
| WO | 2015002724 A2 | 1/2015 | |
| WO | 2015028614 A1 | 3/2015 | |
| WO | 2015173576 A1 | 11/2015 | |
| WO | 2015175307 A1 | 11/2015 | |
| WO | 2016100035 A1 | 6/2016 | |
| WO | 2016100898 A1 | 6/2016 | |
| WO | 2016100909 A1 | 6/2016 | |
| WO | 2016100921 A1 | 6/2016 | |
| WO | 2016100925 A1 | 6/2016 | |
| WO | 2016100930 A1 | 6/2016 | |
| WO | 2016172564 A1 | 10/2016 | |
| WO | 2017019702 A1 | 2/2017 | |
| WO | 2017091943 A1 | 6/2017 | |
| WO | 2017144695 A1 | 8/2017 | |
| WO | 2017177163 A1 | 10/2017 | |
| WO | 2017222879 A1 | 12/2017 | |
| WO | 2018159805 A1 | 9/2018 | |
| WO | 2019018818 A1 | 1/2019 | |
| WO | 2019099725 A1 | 5/2019 | |
| WO | 2019169351 A1 | 9/2019 | |
| WO | 2020033879 A1 | 2/2020 | |
| WO | 2020264072 A1 | 12/2020 | |

OTHER PUBLICATIONS

Rezania, et al. Maturation of human embryonic stem cell-deprived pancreatic progenitors into functional islets capable of treating pre-existing diabetes in mice. Diabetes 61 (2012): 2016-2029.
Rezania, et al. Production of functional glucagon-secreting a-cells from human embryonic stem cells. Diabetes, 60 (Jan. 2011): 239-247.
Rezania, et al. Reversal of diabetes with insulin-producing cells derived in vitro from human pluripotent stem cells. Nat Biotechnol. Nov. 2014;32(11 ): 1121-33. doi: 10.1038/nbt.3033. Epub Sep. 11, 2014.
Roche. Protocols to differentiate embryonic stem cells into insulin producing cells. Av. Diabetol. 24.2 (2008): 128-137.
Rovira, et al., Chemical Screen Identifies FDA-Approved Drugs and Target Pathways That Induce Precocious Pancreatic Endocrine Differentiation, Proc Natl Acad Sci USA. 108.48 (2011): 19264-19269.
Sander, et al. Homeobox gene Nkx6.1 lies downstream of Nkx2.2 in the major pathway of 13-cell formation in the pancreas. Development 127 (2000): 5533-5540.
Sander, et al. The !3-cell transcription factors and development of the pancreas. J Mol Med, 75 (1997): 327-340.
Schuldiner, et al., Effects of eight growth factors on the differentiation of cells derive from human embryonic stem cells, Proc. Nat. Acad. Sci., 97:11307-12 (2000).
Schulz, et al., A scalabe system for production of functional pancreatic progenitors from human embryonic stem cells, PLoS One, 7.5 (May 2012): 1-17.
Schumacher et al.: Staurosporine is a Potent Activator of Neuronal, Glial, and "CNS Stem Cell-Like" Neurosphere Differentiation in Murine Embryonic Stem Cells. Molecular and Cellular Neuroscience 23(4): 669-680 (2003).
Segrev, et al., Differentiation of Human Embryonic Stem Cells into Insulin-Producing Clusters, Stem Cells, 2004, 22:265-274.
Shaer, et al. Differentiation of human-induced pluripotent stem cells into insulin-producing clusters. Exp Clin Transplant. Feb. 2015;13(1):68-75. doi: 10.6002/ect.2013.0131. Epub Jan. 13, 2014.
Shahjalal, et al., Generation of insulin-producing B-like cells from human iPS cells in a defined and completely xeno-free culture system. Journal of Molecular cell biology, Jun. 2014; 6(5):394-408.
Shapiro et al.: International trial of the Edmonton protocol for islet transplantation. N Engl J Med. 355(13): 1318-1330 (2006).
Shi, et al. Inducing Embryonic Stem Cells to Differentiate into Pancreatic !3-cells by a Novel Three-Step Approach with Activin A and All-Trans Retinoic Acid. Stem Cells 23 ( 2005): 656-662.
Shim, et al., Directed differentiation of human embryonic stem cells towards a pancreatic cell fate, Diabetologia, 50 (2007): 1128-1138.
Sneddon, et al. Self-renewal of embryonic-stem-cell-derived progenitors by organ-matched mesenchyme. Nature. Nov. 29, 2012;491 (7426):765-8. doi: 10.1038/nature11463. Epub Oct. 7, 2012.
Sorelle, et al., Beta Cell Replacement Therapy, Type 1 Diabetes-Pathogenesis, Genetics and Immunothera 22 (2011 ): 503-526.
Soria, et al., In-Vitro Differentiation of Pancreatic Beta-Cells, Differentiation, 68(4-5):205-19 (Oct. 2001).
Spence, et al. Sox17 regulates organ lineage segregation of ventral foregut progenitor cells. Dev Cell. Jul. 2009;17(1):62-74. doi: 10.1016/j.devcel.2009.05.012.
Sui et al.: Stem Cell Therapy for Diabetes: A Call for Efficient Differentiation of Pancreatic Progenitors. J. Regen. Med. 2(1):1-4 (2013).
Taylor, et al. NKX6.1 Is Essential for Maintaining the Functional State of Pancreatic Beta Cells. Cell Rep 4 (2013): 1262-275.
Thatava, et al., Indolactam V/GLP-1-mediated Differentiation of Human iPS Cells into Glucose-Responsive Insulin-Secreting Progeny, 18.3 (2011): 283-293.
Thermo Fisher Scientific, B-27 Serum-Free Supplement (SOX) liquid, ThermoFisher Scientific Website, Retrieved from the Internet: URL:https://www.thermofisher.com/nl/en/home/technicalresources/mediaformulation.250.html, on Jun. 13, 2016.
Thowfeequ, et al., Betacellulin inhibits amylase and glucagon production and promotes beta cell differentiation in mouse embryonic pancreas, Diabetologia, 50 (2007): 1688-1697.
Treff, et al., Differentiation of Embryonic Stem Cells Conditionally Expressing Neurogenin 3, Stem Cells, 24.11 (1999): 2529-37.
Trott et al. "Long-Term Culture of Self-renewing Pancreatic Progenitors Derived from Human Pluripotent Stem Cells," Stem Cell Reports, Jun. 6, 2017 (Jun. 6, 2017), vol. 8, No. 6, pp. 1675-1688. entire document.
Tsaniras, et al., "Generating Pancreatic Beta-Cells from Embryonic Stem Cells by Manipulating Signaling Pathways," Journal of Endocrinology, 206:13-26, (2010).
Tsuchida, et al., Activin signaling as an emerging target for therapeutic interventions, Cell Communication & Signaling, 7.15 (2009): 1-11.

(56) References Cited

OTHER PUBLICATIONS

Wachs, et al., High Efficacy of Clonal Growth and Expansion of Adult Neural Stem Cells, LaboratoryInvestigation, 83.7 (Jul. 2003): 949-962.
Xie, et al. Dynamic chromatin remodeling mediated by polycomb proteins orchestrates pancreatic differentiation of human embryonic stem cells. Cell Stem Cell 12 (2013): 224-237.
Zanin, et al., The development of encapsulated cell technologies as therapies for neurological and sensor diseases, Journal of Controlled Release 160 (2012): 3-13.
Zhu, et al., Generation of Pancreatic Insulin-Producing Cells from Rhesus Monkey Induced Pluripotent Stem Cells, Diabetologia, 54 (2011): 2325-2336.
Zhu et al.: Preventive effect of Notch signaling inhibition by a gamma-secretase inhibitor on peritoneal dialysis fluid-induced peritoneal fibrosis in rats. Am J Pathol. 176(2): 650-659 (2010).
Zulewski, Stem Cells with potential to generate insulin-producing cells in man, Swiss Med. Wkly, 136 (2006): 647-654.
Zweigerdt, et al., Scalable expansion of human pluripotent stem cells in suspension culture, Nature Protocols, 6.5 (2011): 689-700.
Mihara, Yuichiro; et al; "Production of pancreatic progenitor cells from human induced pluripotent stem cells using a three-dimensional suspension bioreactor system" Journal of Tissue Engineering and Regenerative Medicine, 11, 3193-3201, 2017 (Year: 2017).
Abraham et al.: Glucagon action in the brain. Diabetologia 59(7):1367-1371 doi:10.1007/s00125-016-3950-3 (2016).
Bi Ress I et al.: The homeobox gene Arx is a novel positive regulator of embryonic myogenesis. Cell Death Differentiation 15(1) :94-104 doi: 10.1038/sj .cdd .4402230 (2008).
Cai et al.: Isl1 identifies a cardiac progenitor population that proliferates prior to differentiation and contributes a majority of cells to the heart. Dev. Cell 2003 5(6):877-889 doi:10.1016/s1534-5807(03)00363-0 (2003).
Eisenberg et al.: Establishment of the mesodermal cell line QCE-6. A model system for cardiac cell differentiation. Circ Res. 78(2):205-216 (1996).
Hamamoto et al.: Lack of evidence for recipient precursor cells replenishing !3-cells in transplanted islets. Cell Transplant 19(12):1563-1572 doi:10.3727/096368910X515881 (2010).
Kieffer et al.: Beta-cell replacement strategies for diabetes. J Diabetes Investig. 9(3):457-463 doi: 10.1111 / jdi. 12758 (2017).
Kim et al.: Functional Diversification of Motor Neuron-specific Isl1 Enhancers during Evolution. PLoS Genetics 11(10): e1005560, pp. 1-27 doi:10.1371/journal.pgen.1005560 (2015).
Korytnikov: Role of Tankyrase Inhibitors in the Generation of NKX6-1 + Endoderm. Dissertation, University of Toronto, pp. 1-84 URL: https://hdl.handle.net/1807/92864 (2016).
Lopez et al.: Staurosporine-derived inhibitors broaden the scope of analog-sensitive kinase technology. J Am Chem Soc. 135(48):18153-18159 doi:10.1021/ja408704u (2013).
Moore et al.: Noninvasive in vivo measurement of beta-cell mass in mouse model of diabetes. Diabetes 50 (10):2231-2236 doi:10.2337/diabetes.50.10.2231 (2001).
Papas et al.: Islet assessment for transplantation. Curr Opin Organ Transplant 14(6) :67 4-682 doi:10.1097/MOT.0b013e328332a489 (2009).
Prakash et al.: Nkx6-1 controls the identity and fate of red nucleus and oculomotor neurons in the mouse midbrain. Development 136(15):2545-2555 doi:10.1242/dev.031781 (2009).
Reyes et al.: (Retracted)Purification and ex vivo expansion of postnatal human marrow mesodermal progenitor cells. Blood 98:2615-2625 [1-1] (2001).
Takahashi et. al: Induction of pluripotent stem cells from fibroblast cultures. Nat Protoc. 2(12):3081-3089 (2007).
U.S. Appl. No. 17/472,220 Non-Final Office Action dated Jan. 6, 2022.
U.S. Appl. No. 17/472,263 Non-Final Office Action dated Jan. 6, 2022.
Vertex Press Release, "Vertex to Acquire ViaCyte, With the Goal of Accelerating its Potentially Curative VX-880 Programs in Type 1 Diabetes", {Jul. 11, 2022).
Wimalasena: Vesicular monoamine transporters: structure-function, pharmacology, and medicinal chemistry. Med. Res. Rev.31 (4):483-519 doi:10.1002/med.20187 (2011).
DW Engers, et al., Synthesis and structure-activity relationships of a novel and selective bone morphogenetic protein receptor (BMP) inhibitor derived from the pyrazolo[1.5-a]pyrimidine scaffold of dorsomorphin: the discovery of ML347 as an ALK2 versus ALK3 selective MLPCN probe. Bioorg. Med. Chem. Lett. 2013, 23, 3248-3252.
EP18879005.9 Extended European Search Report dated Jul. 13, 2021.
Extended European search Report for corresponding EP Application No. 18836082.0 dated Feb. 24, 2021.
Gotoh et al., Gamma-Irradiation as a Tool to Reduce Immunogenicity of Islet Allo-and-Xeonograpfs, Horm Metab Res Suppl., Jan. 1, 1990, vol. 25, pp. 89-96. Abstract only.
Hao, et al., In Vivo Structure Activity Relationship Study of Dorsomorphin Analogs Identifies Selective VEGF and BMP Inhibitors, ACS Chem Biol., Feb. 19, 2010, vol. 5, No. 2, pp. 245-253.
Hess et al., Bone Marrow-Derived Stem Cells Initiate Pancreatic Regeneration, Nature Biotechnology, Jun. 22, 2003, vol. 21, Issue 7, pp. 763-770.
International Search Report and Written Opinion for PCT/US2018/043179 dated Oct. 16, 2018.
Koshimizu et al.: Functional requirement of gp130-mediated signaling for growth and survival of mouse primordial germ cells in vitro and derivation of embryonic germ (EG) cells. Development 122(4):1235-1242 (1996).
Lee et al., Differentiation into Endoderm Lineage: Pancreatic differentiation from Embryonic Stem Cells, International Journal of Stem Cells, Apr. 4, 2011, vol. 4, No. 1, pp. 35-42.
Lima et al., Generation of Functional Beta-Like Cells from Human Exocrine Pancreas, PLoS One, May 31, 2016, vol. 11, No. 5, pp. 1-19.
Massumi et al.: An abbreviated protocol for in vitro generation of functional human embryonic stem cell-derived beta-like cells. PLoS One 11 (1 0):e0164457 DOI:10.1371/journal.pone.0164457 [1-24] (2016).
Matsui, Y., et al., (1992), Derivation of pluripotential embryonic stem cells from murine primordial germ cells in culture, Cell 70:841.
Morrison et al.: Regulatory Mechanisms in Stem Cell Biology. Cell 88(3):287-298 (1997).
Neely et al., DMH1, a Highly Selective Small Molecule BGMP Inhibitor Promotes Neurogenesis of hiPSCs: Comparison of PAX6 and SOX1 Expression During Neural Induction, ACS Chem Neurosci, Mar. 5, 2012, vol. 3, No. 6, pp. 482-491.
PCT/US2018/061364 International Search Report and Written Opinion dated Apr. 29, 2019.
PCT/US2019/020430 International Search Report and Written Opinion dated May 8, 2019.
PCT/US2019/045985 International Search Report and Written Opinion mailed Dec. 17, 2019.
PCT/US2020/039487 International Search Report and Written Opinion dated Sep. 22, 2020.
Russ et al.: Controlled induction of human pancreatic progenitors produces functional beta-like cells in vitro. EMBO J. 34(13):1759-1772 (2015).
Segerstople et al.: Single-cell transcriptome profiling of human pancreatic islets in health and type 2 diabetes. Cell Metab. 24(4):593-607 (2016).
Shamblott, et al. Derivation of pluripotent stem cells from cultured human primordial germ cells, Proc. Natl. Acad. Sci. USA, vol. 95, pp. 13726-13731 (1998).
Takahashi, et al. Induction of pluripotent stem cells from adult human fibroblasts by defined factors. Cell. Nov. 30, 2007;131 (5):861-72.
Thomson et al. Embryonic stem cell lines derived from human blastocysts. Science. Nov. 6, 1998;282(5391 ):1145-7.

(56) References Cited

OTHER PUBLICATIONS

Thomson et al., Pluripotent Cell Lines Derived from Common Marmoset (*Callithrixjacchus*) Blastocysts, (1996) Biol. Reprod. 55:254-259.

Vegas, et al., Long term glycemic control using polymer encapsulated, human stem-cell derived B-cells in immune competent mice, Nat Med. Jan. 25, 2016, vol. 22, No. 3, pp. 306-311.

Yu, et al. Induced pluripotent stem cell lines derived from human somatic cells. Science. Dec. 21, 2007 ;318 (5858):1917-20. Epub Nov. 20, 2007.

Ax xora.com Product Search Results for "AlkS Inhibitor." Retrieved from URL:https://www.axxora.com/product-listing/ on Oct. 21, 2020 [1-2](Year: 2020).

Blazhevich, et al., "Cell Culturing: Lecture Course," 6 pages (1 page of translation of relevance) (2004).

Cai, et al., Generation of Homogeneous PDX1 p Pancreatic Progenitors from Human ES Cellderived Endoderm Cells, Journal of Molecular Cell Biology (2010), 2:50-60.

Hrvatin: Exploring the Use of Human Pluripotent Stem Cells to Create Functional Pancreatic 13 Cells. Harvard University Library, Doctoral Dissertation. [1-165] (2012) https://dash. harvard .edu/ bitstream/hand le/1/104334 70/ Hrvatin_gsas. harvard_0084L_ 10728. pdf ?sequence=3&isAllowed=y.

Okazaki et al.: Staurosporine, a novel protein kinase inhibitor, enhances HL-60-cell differentiation induced by various compounds. Exp. Hemtaol. 16(1):42-48 (1988).

Ropiquet et al.: FGF7/KGF triggers cell transformation and invasion on immortalised human prostatic epithelial PNT1A cells. Int. J. Cancer 82(2):237-243 (1999).

Roskoski: A historical overview of protein kinases and their targeted small molecule inhibitors. Pharmalogical Res. 100:1-23 (2015).

Tian et al.: Protein kinase C and calcium regulation of adenylyl cyclase in isolated rat pancreatic islets. Diabetes 50 (11 ):2505-2513 (2001 ).

Veres et al.: Charting cellular identity during human in vitro 13-cell differentiation. Nature 569(7756):368-373 [1-36] (2019).

Xu et al.: Revealing a core signaling regulatory mechanism for pluripotent stem cell survival and self-renewal by small molecules. PNAS 107(18):8129-8134 (2010).

Zhang et al.: Highly efficient differentiation of human ES cells and iPS cells into mature pancreatic insulin-producing cells. Cell Research 19(4):429-438 (2009).

Zhdanov, et al., "The Secrets of the Third Kingdom," Publishing House "Znanie" Moscow:pp. 124-125, (1975). (2 pages of translation).

Aguayo-Mazzucato, et al., "Mafa Expression Enhances Glucose-Responsive Insulin Secretion in Neonatal Rat Beta Cells," Diabetologia, 54(3):583-593, (Mar. 2011).

Aguayo-Mazzucato, et al., "Thyroid Hormone Promotes Postnatal Rat Pancreatic 13-Cell Development and Glucose-Responsive Insulin Secretion Through MAFA," Diabetes, 62: 1569-1580, (2013).

"Agulnick, et al., "Insulin-Producing Endocrine Cells Differentiated In Vitro From Human Embryonic Stem Cells Function in Macroencapsulation Devices In Vivo" (2015) Cells Translation Medicine 4:1214-1222".

Amariglio, et al., "Donor-Derived Brain Tumor Following Neural Stem Cell Transplantation in an Ataxia Telangiectasia Patient," PLOS Medicine, 6(2):1-3, (2009).

Apelqvist, et al., Notch Signaling Controls Pancreatic Cell Differentiation, Nature 400, (1999): 877-881 .

Ashery-Padan, et al. Conditional inactivation of Pax6 in the pancreas causes early onset of diabetes. Developmental Biology, 269 (2004): 479-488.

Assady, et al. Insulin Production by Human Embryonic Stem Cells. Diabetes, 50 (2001): 1691-1697.

Baetge, E. E., Production of !3-cells from human embryonic stem cells, Diabetes, Obesity and Metabolism 10 (2008): 186-194.

Basford, et al., The Functional and molecular Characterisation of Human Embryonic Stem Cell-Derived Insulin-Positive Cells Compared with Adult Pancreatic Beta Cells, Diabetologia, 55 (2012): 358-371.

Beattie, et al., Sustained proliferation of PDX-1 + cells derived from human islets, Diabetes, 1999, 48:1013-9.

Bellin, et al. Potent induction immunotherapy promotes long-term insulin independence after islet transplantation in type 1 diabetes. Am J Transplant. Jun. 2012;12(6):1576-83. doi: 10.1111/j.1600-6143.2011.03977.x. Epub Apr. 11, 2012.

Bennett, et al. SP600125, An Anthrapyrazolone Inhibitor of Jun N-Terminal Kinase. PNAS, vol. 98, No. 24, 20, 2001, pp. 13681-13686.

Boretti, et al., Induced cell clustering enhances islet beta cell formation from human cultures enriched for pancreatic ductal epithelial cells, 2003 Summer Bioengineering Conference, Jun. 25-29, Sonesta Beach Res ort in Ke Sisca ne, Florida.

Boretti, et al. Induced cell clustering enhances islet beta cells formation from human cultures enriched for pancreatic ductal epithelial cells, Tissue Engg. 12.4 (2006): 939-948.

Bose, et al., Human embryonic stem cell differentiation into insulin secreting beta-cells for diabetes, Cell Bioi Int., 3611 (2012): 1013-1020.

Brolen, et al. Signals From the Embryonic Mouse Pancreas Induce Differentiation of Human Embryonic Stem Cells Into Insulin-Producing r3-cell-like Cells. Diabetes 54 (2005): 2867-2874.

Campbell-Thompson, et al., "Collection Protocol for Human Pancreas," Journal of Visualized Experiments, 63:1-5, (May 2012).

CERF, Transcription factors regulating !3-cell function, European Journal of Endocrinology, 155 (2006): 671-679.

Chakrabarti, et al., Transcription factors direct the development and function of pancreatic beta cells, Trends Endocrinol Metab., 14.2 (Mar. 2003): 78-84.

Chen, et al., Scalable GMP complain suspension culture system for human ES cells, Stem Cell Research 8 (2012): 388-402.

Cheng, et al. Self-renewing endodermal progenitor lines generated from human pluripotent stem cells. Cell Stem Cell 10 (2012): 371-384.

"Chiang, et al., Single-Cell Transcript Analysis of Pancreas Development, Developmental Cell, Mar. 2003, 4:383-393".

Choi, et al. A comparison of genetically matched cell lines reveals the equivalence of human iPSCs and ESCs. Nat Biotechnol. Nov. 2015;33(11):1173-81. doi: 10.1038/nbt.3388. Epub Oct. 26, 2015.

"CMRL-1066 Data Sheet. Retrieved online Sep. 30, 2017. https://www.sigmaaldrich.com/content/dam/sigma aldrich/docs/sigma/datasheet/c0422dat.pdf (1998).".

Cohen, et al., Antibiotics Reduce the Growth Rate and Differentiation of Embryonic Stem Cell Cultures, Tissue Eng., 12.7 (2006): 2025-2030.

Corkey, et al., A Role for Malonyl-CoA in Glucose-Stimulated Insulin Secretion from Clonal Pacreatic 13-Cells, J. Bioi. Chem., 254.36 (Dec. 1989): 21608-21612.

D'Amour, et al., Efficient differentiation of human embryonic stem cells to definitive endoderm, Nat. Biotech., 23(12):1534-41 (2005).

D'Amour, et al. Production of pancreatic hormone-expressing endocrine cells from human embryonic stem cells. Nat Biotechnol. Nov. 2006;24(11):1392-401.

Docherty, "Pancreatic Stellate Cells Can Form New 13-Like Cells," Biochem, J., 421 :e1-e4, (2009).

Dror, et, al., Notch Signaling Suppresses Apoptosis in Adult Human and Mouse Pancreatic Islet Cells, Diabetlogia 50 (2007): 2504-2515.

Eberhardt, et al. Multipotential nestin and Isl-1 positive mesenchymal stem cells isolated from human pancreatic islets. Biochem Biophys Res Commun. Jul. 7, 2006; 345.3, 1167-76. Epub May 11, 2006.

Falzacappa et al., "3,5,3'-Triiodothyronine (T3) is a Survival Factor for Pancreatic Beta-Cells Undergoing Apoptosis," J. Cell Physiol., 206(2):309-321, (Feb. 2006).

Greggio, et al., Artificial Three-Dimensional Niches Deconstruct Pancreas Development in vitro, Development, 140 (2013): 4452-4462.

Habener, et al., Minireview: transcriptional regulation in pancreatic development Endocrinol., 146:1025-34 (2005).

(56) References Cited

OTHER PUBLICATIONS

Hanley, "Closing in on Pancreatic Beta Cells," Nature Biotechnology, 32(11):1100-1102, (Nov. 2014).
Haycock, John W., 3D Cell Culture: A Review of Current Approaches and Techniques, Molecular Biolo 695 (2011): 1-15.
Heremans, et al., Recapitulation of embryonic neuroendocrine differentiation in adult human pancreatic duct cells expressing neurogenin 3, The Journal of Cell Biology, Oct. 28, 2002, 159(2):303-311.
Hernandez, et al., Microcapsules and microcarriers for in situ cell delivery, Advanced Drug Deliver Reviews 62 (2010): 711-730.
"Hilderink, et al., "Controlled aggregation of primary human pancreatic islet cells leads to glucose-responsive pseudoislets comparable to native islets" (2015) J. Cell. Mol. Med., vol. 19, No. 8, pp. 1836-1846".
Hrvatin, et al. Differentiated human stem cells resemble fetal, not adult, !3-cells. PNAS, 111.8, 3038-3043, Year: 2014.
Hur et al.: New method to differentiate human peripheral blood monocytes into insulinproducing cells: Human hematosphere culture. Biochem Biophys Res Commun.418(4): 765-769 (2012).
Huynh, et al., "Screening and Identification of a Novel Class of TGF-13 Type 1 Receptor Kinase Inhibitor," Society for Laboratory Automation and Screening, 16(7):724-733, (2011).
Isayeva, et al. Characterization and performance of membranes designed for macroencapsulation/implantation of pancreatic islet cells. Biomaterials. Sep. 2003;24(20):3483-91.
Jahansouz, et al., Evolution of 13-Cell Replacement Therapy in Diabetes Mellitus: Islet Cell Transplantation, Journal of Transplantation, (2011): 1-21.
Jeon et al.: Differentiation and Transplantation of Functional Pancreatic Beta Cells Generated from Induced Pluripotent Stem Cells Derived from a Type 1 Diabetes Mouse Model. Stem Cells Dev., 21 (14): 2642-2655, (2012).
Jiang, et al. In vitro derivation of functional insulin-producing cells from human embryonic stem cells. Cell Res. Apr. 2007; 17(4):333-44.
Kelly, et al., "Cell-surface markers for the isolation of pancreatic cell types derived from human embryonic stem cells" (2011) Nature Biotechnology, p. 1-19.
Kojima, Nobuhiko "In vitro reconstitution of pancreatic islets" (2014) Organogenesis 10:2, pp. 225-230.
Kozhukharova et al.: Novel Human Embryonic Stem Cell Lines C612 and C910. Cytology, 51 (7): 551-558 (2009).
Kroon, et al., Pancreatic endoderm derived from human embryonic stem cells generates glucose-responsive insulin-secreting cells in vivo, Nat. Biotech, Apr. 2008, 26(4):443-452.
Kumar, et al., Recent Developments in 13-Cell Differentiation of Pluripotent Stem Cells Induced by Small and Large Molecules, Int. J. Mol. Sci., 15.12 (2014): 23418-23447.
Kumar, et al. Signals from lateral plate mesoderm instruct endoderm toward a pancreatic fate. Dev Bioi. 259.1 (2003): 109-22.
Kunisada, et al., Small molecules induce efficient differentiation into insulinproducing cells from human induces pluripotent stem cells, Stem Cell Research, 2012, 8:274-284.
Lee et al.: Al I-Trans-Retinoic Acid as a Novel Therapeutic Strategy for Alzheimer's Disease. Expert Rev. Neurother, 9 (11): 1615-1621 (2009).
Lim et al., Microencapsulated islets as bioartificial endocrine pancreas, Science 210(4472):908-10 (1980).
Lin et al.: Transforming growth factor-beta/Smad3 signaling regulates insulin gene transcription and pancreatic islet beta-cell function. J Biol Chem.284(18): 12246-12257 (2009).
Lumelsky, et al., Differentiation of Embryonic Stem Cells to Insulin-Secreting Structures Similar to Pancreatic Islets, Science, 292:1389-94 (May 2001).
Madsen, et al. Towards cell therapy for diabetes. Nat Biotechnol. 24.12 (2006): 1481-3.
Maehr, et al., Generation of pluripotent stem cells from patients with type 1 diabetes, Proc Natl Acad Sci. 106.37 (2009): 15768-15773.
Manning et al. The Protein Kinase Complement of the Human Genome. Science. 298:1912-1934.2002.
Marzorati, et al., Culture Medium Modulates Proinflammatory Conditions of Human Pancreatic Islets Before Transplantation, Am. J. Transplant, 6.11 (2006): 2791-2795.
Matschinsky, Assessing the potential of glucokinase activators in diabetes therapy, Nature Reviews Drug Discovery, 8 (2009): 399-416.
McLean, et al., Activin a Efficiently Specifies Definitive Endoderm from Human Embryonic Stem Cells Only When Phosphatidylinositol 3-Kinase Signaling Is Suppressed. Stem Cells, 2007, 25: 29-38.
McQuilling et al.: New Alginate Microcapsule System for Angiogenic Protein Delivery and Immunoisolation of Islets for Transplantation in the Rat Omentum Pouch. Transplantation Proceedings, 43(9): 3262-3264 (Nov. 2011).
Smelt, et al., "Pancreatic Beta-Cell Purification by Altering FAD and NAD(P)H Metabolism" (2018) Experimental Diabetes Research vol. 2008, Article ID 165360, pp. 1-11.
Michael, et al., Pancreatic 13-Cells Secrete Insulin in Fast- and Slow-Release Forms, Diabetes, 55 (2006): 600-607.
Moens, et al., Dual glucagon recognition by pancreatic beta-cells via glucagon and glucagonlike peptide 1 receptors, Diabetes, 47 (1998): 66-72.
Mollard, et al. Design, Synthesis and Biological Evaluation of a Series of Novel Axl Kinase Inhibitors. ACS Med Chem Lett. Dec. 8, 2011;2(12):907-912.
Motte, et al. Composition and function of macroencapsulated human embryonic stem cellderived implants: comparison with clinical human islet cell grafts. Am J Physiol Endocrinol Metab. Nov. 1, 2014 ;307(9):E838-46. doi: 10.1152/ajpendo.00219.2014. Epub Sep. 9, 2014.
Mudduluru, et al. Regulation of Axl receptor tyrosine kinase expression by miR-34a and miR-199a/b in solid cancer. Oncogene. Jun. 23, 2011;30(25):2888-99. doi: 10.1038/onc.2011.13.Epub Feb. 14, 2011.
Murua, et al., Cell microencapsulation technology: Towards clinical application, Journal of Controlled Release, 132.2 (2008): 76-83.
Narayanan, et al. Extracellular Matrix-Mediated Differentiation of Human Embryonic Stem Cells: Differentiation to Insulin-Secreting Beta Cells. Tissue Engineering, Part A, 20.1 & 2, 424-433, Year: 2014.
Natalicchio et al.: Exendin-4 Protects Pancreatic Beta Cells from Palmitate-Induced Apoptosis by Interfering with GPR40 and the MKK4/7 Stress Kinase Signaling Pathway. Diabetologia, 56: 2456-2466 (2013).
Nishimura, et al., "A Switch from MafB to MafA Expression Accompanies Differentiation to Pancreatic 13-Cells," Developmental Biology, 293:526-539, (2006).
Nostro, et al., Generation of beta cells from human pluripotent stem cells: Potential for regenerative medicine, Seminars in Cell & Developmental Biology, 23 (2012): 701-710.
O'Brien, et al., Suspended in culture-Human pluripotent cells for scalable technologies, Stem cell Research 9 (2012): 167-170.
Orive, et al., Application of cell encapsulation for controlled delivery of biological therapeutics, Advanced Dru Delive Reviews 1-12 2013.
Pagliuca, et al. Generation of functional human pancreatic 13 cells in vitro. Cell. Oct. 9, 2014;159(2):428-39. doi: 10.1016/j.cell.2014.09.040.
Pagliuca et al.: How to make a functional !3-cell. Development 140, 2472-2483 (2013).
Parsons, et al., Notch-Responsive Cells Initiate the Secondary Transition in Larval Zebrafish Pancreas, Mechanism of Development, 126.10 (2009): 898-912.
Phillips, et al., Directed Differentiation of Human Embryonic Stem Cells into the Pancreatic Endocrine Lineage, Stem Cells and Dev., 16 (2007): 561-578.
Spijker, et al., "Conversion of Masture Human B-Cells Into Glucagon-Producing a-Cells" (2013) Diabetes, vol. 62, p. 2471-2480.
Piran, et al., "Pharmacological Induction of Pancreatic Islet Cell Transdifferentiation; Relevance Type I Diabetes, " Cell Death and Disease, 5(e1357):1-13, (2014).

(56) References Cited

OTHER PUBLICATIONS

Qi et al.: PVA Hydrogel Sheet Macroencapsulation of the Bioartificial Pancreas. Biomaterials, 24(27): 5885-5892 (2004).
Ramachandran, et al., "Assessment of re-aggregated human pancreatic islets for secondary drug screening" British Journal of Pharmacology (2014) 171 3010-3022.
Ratanasavanh, et al. Immunocytochemical evidence for the maintenance of cytochrome PC33 450 isozymes, NADPH cytochrome C reductase, and epoxide hydrolase in pure and mixed primary cultures of adult human hepatocytes. J Histochem Cytochem. 34.4 (1986): 527-33.
Rathaore, et al., Microencapsulation of Microbial cells, Journal of Food Engineering, 116 (2013): 369-381.
Ravassard, et al. A genetically engineered human practical 13 cell line exibiting glucoseinducible insulin secretion. The Journal of clinical investigation 121.9 (2011): 3589-3597.

\* cited by examiner

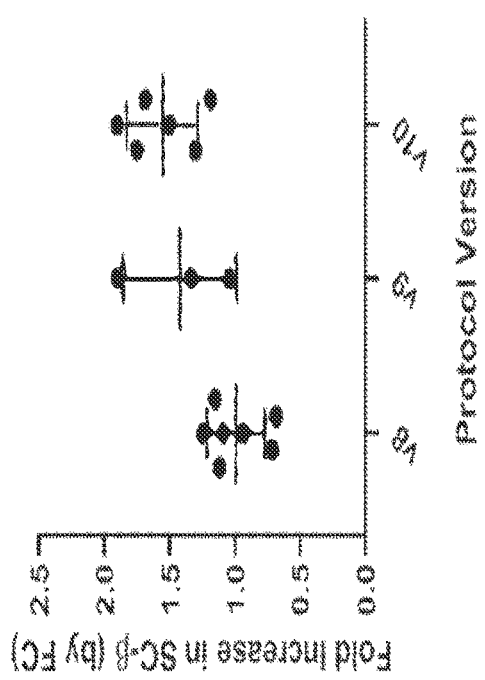
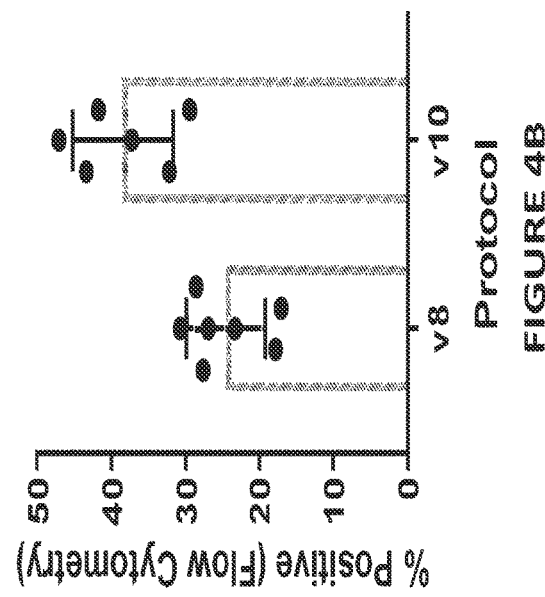
FIGURE 4A
FIGURE 4B

Stem Cell Derived Islet (SC-β)
Natural Pancreas Derived Islet (Organ Donor)
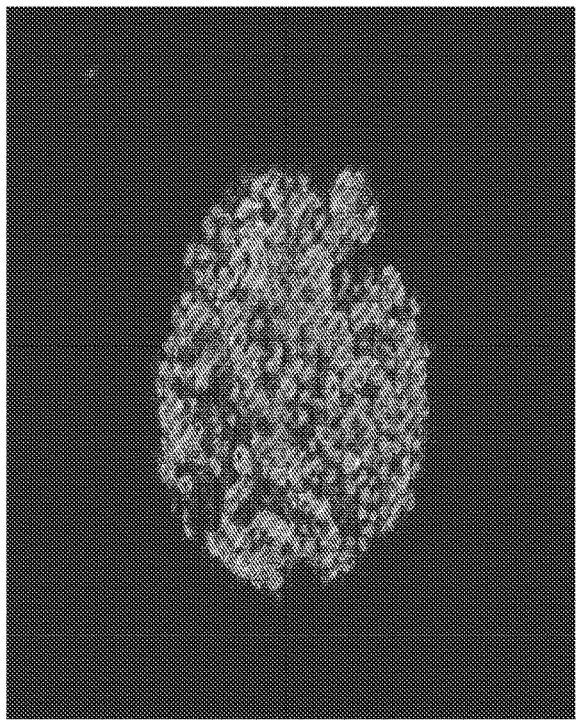
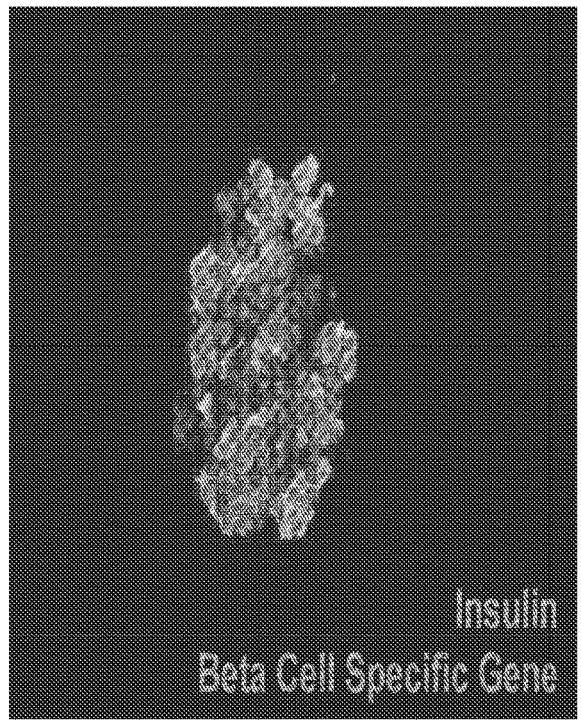
Insulin
Beta Cell Specific Gene
FIGURE 5

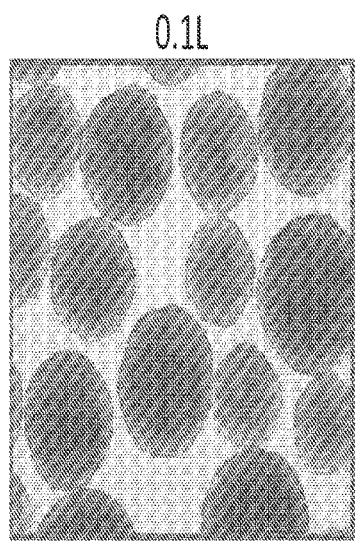
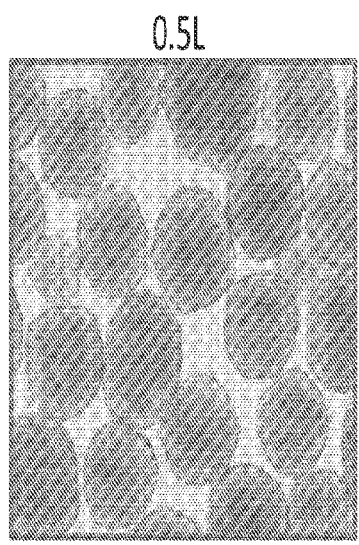
FIGURE 9A     FIGURE 9B     FIGURE 9C
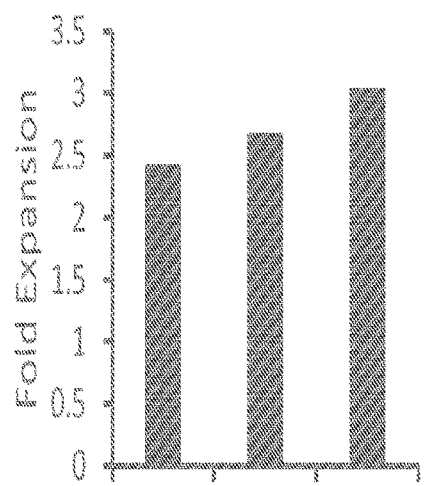
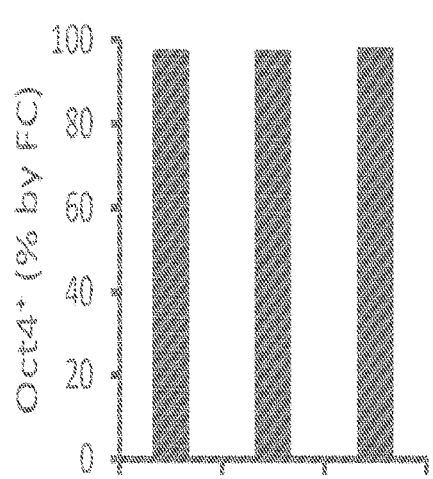
FIGURE 9D     FIGURE 9E

ISLET CELL MANUFACTURING COMPOSITIONS AND METHODS OF USE

CROSS-REFERENCE

This application is a division of U.S. patent application Ser. No. 16/864,886, filed May 1, 2020, which is a continuation of international application No. PCT/US2018/061364, filed on Nov. 15, 2018, which claims the benefit of U.S. Provisional Application No. 62/586,808, filed on Nov. 15, 2017, and U.S. Provisional Application No. 62/669,170, filed on May 9, 2018, each of which is incorporated herein by reference in its entirety.

INCORPORATION BY REFERENCE OF SEQUENCE LISTING

The Sequence Listing in the XML file, named as 41627ZY_SequenceListing of 23 KB, created on Feb. 16, 2024 and submitted to the United States Patent and Trademark Office via Patent Center, is incorporated herein by reference.

BACKGROUND OF THE DISCLOSURE

Diabetes is a major healthcare problem globally. Approximately, more than 400 million people suffer from diabetes and tis complications worldwide as reported by International Diabetes Federation in 2015. Among them, more than 50 million people require insulin injections. Death or dysfunction of pancreatic β cells in pancreatic islets which leads to abnormal insulin secretion can cause diabetes. The generation of stem cell derived 3-cells can provide a potentially useful step toward the generation of islets and pancreatic organs, which can potentially provide therapeutic treatment of diabetes. One of the rapidly growing diseases that may be treatable by stem cell derived tissues is diabetes. Type I diabetes can result from autoimmune destruction of β-cells in the pancreatic islet. Type II diabetes can result from peripheral tissue insulin resistance and β-cell dysfunction. Diabetic patients, particularly those suffering from type I diabetes, can potentially be cured through transplantation of new β-cells. Patients transplanted with cadaveric human islets can be made insulin independent for 5 years or longer via this strategy, but this approach is limited because of the scarcity and quality of donor islets. The generation of an unlimited supply of human β-cells from stem cells can extend this therapy to millions of new patients and can be an important test case for translating stem cell biology into the clinic.

SUMMARY OF THE DISCLOSURE

Disclosed herein, in some aspects, is a method for generating a cell cluster that comprises Pdx1-positive, NKX6.1-positive pancreatic progenitor cells, the method comprising: contacting a population of Pdx1-negative, NKX6.1-negative primitive gut tube cells with a composition comprising a bone morphogenetic protein (BMP) signaling pathway inhibitor and a growth factor from transformation growth factor 3 (TGF-β) superfamily, thereby generating a cell cluster that comprises Pdx1-positive, NKX6.1-positive pancreatic progenitor cells, wherein the cluster comprises at most about 30% CHGA-positive cells and at most about 30% CDX2-positive cells as measured by flow cytometry.

In some embodiments, the method further comprises differentiating the PDX1-positive/NKX6.1-negative pancreatic progenitor cells into pancreatic β cells.

In some embodiments, the method further comprises differentiating the PDX1-positive/NKX6.1-negative pancreatic progenitor cells into PDX1-positive/NKX6.1-positive pancreatic progenitor cells.

In some embodiments, the method further comprises differentiating the NKX6.1-positive pancreatic progenitor cells into insulin-positive endocrine cells.

In some embodiments, the method further comprises differentiating the insulin-positive endocrine cells into pancreatic β cells.

Disclosed herein, in some aspects, is a method comprising: (a) contacting a population of cells comprising a Pdx1-positive, NKX6.1-positive primitive gut tube cell with a composition comprising a BMP signaling pathway inhibitor and a growth factor from TGF-β superfamily, thereby generating a cell cluster comprising a Pdx1-positive, NKX6.1-positive pancreatic progenitor cell; and (b) differentiating the cell cluster comprising the PDX1-positive/NKX6.1-positive pancreatic progenitor cell into a cell cluster comprising non-native pancreatic β cells, wherein the cell cluster comprising non-native pancreatic β cells has a glucose-stimulated insulin secretion (GSIS) stimulation index higher than a comparable cell cluster generated without the contacting with the BMP signaling pathway inhibitor and the growth factor from TGF-β superfamily.

In some embodiments, the GSIS stimulation index of the cell cluster is at least about 1.2 fold, at least about 1.5 fold, at least about 1.8 fold, at least about 2 fold, at least about 2.2 fold, at least about 2.4 fold, at least about 2.8 fold, or at least about 3 fold higher than that of the comparable cell cluster. In some embodiments, the GSIS stimulation index of the cell cluster is at least about 3 fold higher than that of the comparable population. In some embodiments, the GSIS stimulation index is calculated as a ratio of insulin secretion in response to a first glucose concentration to insulin secretion in response to a second glucose concentration. In some embodiments, the first glucose concentration is about 10 to about 50 mM, and the second glucose concentration is about 1 mM to 5 mM. In some embodiments, the first glucose concentration is about 20 mM, and the second glucose concentration is about 2.8 mM. In some embodiments, the cell cluster comprises a higher percentage of the non-native pancreatic β cell than the comparable cell cluster as measured by flow cytometry. In some embodiments, the cell cluster comprises a percentage of the non-native pancreatic β cell at least about 1.1 fold, at least about 1.2 fold, at least about 1.3 fold, at least about 1.4 fold, or at least about 1.5 fold higher than the comparable cell cluster as measured by flow cytometry. In some embodiments, the cell cluster comprises a percentage of the non-native pancreatic β cells about 1.5 fold higher than the comparable cell cluster as measured by flow cytometry.

Disclosed herein, in some aspects, is a method comprising: (a) contacting a population of cells comprising a Pdx1-positive, NKX6.1-positive primitive gut tube cell with a composition comprising a BMP signaling pathway inhibitor and a growth factor from TGF-β superfamily, thereby generating a cell cluster comprising a Pdx1-positive, NKX6.1-positive pancreatic progenitor cell; and (b) differentiating the cell cluster comprising the PDX1-positive/NKX6.1-positive pancreatic progenitor cell into a cell cluster comprising non-native pancreatic β cells, wherein the cell cluster comprising non-native pancreatic β cells comprises a higher percentage of the non-native pancreatic β cell, as measured by flow cytometry, as compared to a comparable cell cluster generated without the contacting with the BMP signaling pathway inhibitor and the growth factor from TGF-β superfamily.

In some embodiments, the cell cluster comprising the non-native pancreatic β cells comprises a percentage of the non-native pancreatic β cells at least about 1.1 fold, at least about 1.2 fold, at least about 1.3 fold, at least about 1.4 fold, or at least about 1.5 fold higher than the comparable cell cluster as measured by flow cytometry. In some embodiments, the cell cluster comprising the non-native pancreatic β cells comprises a percentage of the non-native pancreatic β cells about 1.5 fold higher than the comparable cell cluster as measured by flow cytometry. In some embodiments, the cell cluster comprising the non-native pancreatic β cells exhibits a higher insulin secretion in response to a glucose challenge as compared to the comparable cell cluster. In some embodiments, the cell cluster comprising the non-native pancreatic β cells exhibits at least about 1.2, 1.5, 2, 2.5, 3, 3.5, 4, 4.5, or 5 fold higher an insulin secretion in response to a glucose challenge as compared to the comparable cell cluster. In some embodiments, the cell cluster comprising the non-native pancreatic β cells exhibits a higher GSIS stimulation index as compared to the comparable cell cluster. In some embodiments, the GSIS stimulation index of the cell cluster comprising the non-native pancreatic β cells is at least about 1.2 fold, at least about 1.5 fold, at least about 1.8 fold, at least about 2 fold, at least about 2.2 fold, at least about 2.4 fold, at least about 2.8 fold, or at least about 3 fold higher than that of the comparable cell cluster. In some embodiments, the GSIS stimulation index of the cell cluster comprising the non-native pancreatic β cells is at least about 3 fold higher than that of the comparable cell cluster. In some embodiments, the GSIS stimulation index is calculated as a ratio of insulin secretion in response to a first glucose concentration to insulin secretion in response to a second glucose concentration. In some embodiments, the first glucose concentration is about 10 to about 50 mM, and the second glucose concentration is about 1 mM to 5 mM. In some embodiments, the first glucose concentration is about 20 mM, and the second glucose concentration is about 2.8 mM. In some embodiments, the non-native pancreatic β cells exhibit an in vitro glucose-stimulated insulin secretion response when exposed to a glucose challenge. In some embodiments, the non-native pancreatic β cells exhibit an insulin secretion in response to a first concentration of $K^+$. In some embodiments, the cell cluster comprising the non-native pancreatic β cells exhibits a higher insulin secretion as compared to the comparable cell cluster in response to a first concentration of $K^+$. In some embodiments, the cell cluster comprising the non-native pancreatic β cells exhibits at least about 1.2 fold, at least about 1.5 fold, at least about 1.8 fold, at least about 2 fold, at least about 2.2 fold, at least about 2.4 fold, at least about 2.8 fold, at least about 3 fold, at least about 3.2 fold, at least about 3.4 fold, at least about 3.6 fold, at least about 3.8 fold, at least about 4 fold higher an insulin secretion as compared to the comparable cell cluster in response to a first concentration of $K^+$. In some embodiments, the inhibitor of the BMP signaling pathway comprises DMH-1, a derivative, analogue, or variant thereof. In some embodiments, the composition comprises about 0.01 μM to about 10 μM, about 0.05 μM to about 5 μM, about 0.1 μM to about 1 μM, or about 0.15 μM to about 0.5 μM DMH-1. In some embodiments, the composition comprises about 0.25 μM DMH-1. In some embodiments, the growth factor from TGF-β superfamily comprises Activin A. In some embodiments, the composition comprises about 0.5 ng/mL to about 200 ng/mL, about 1 ng/mL to about 100 ng/mL, about 2 ng/mL to about 50 ng/mL, or about 5 ng/mL to about 30 ng/mL Activin A. In some embodiments, the composition comprises at least about 5 ng/mL or at least about 10 ng/mL Activin A. In some embodiments, the composition comprises about 20 ng/mL Activin A. In some embodiments, the composition further comprises a differentiation factor selected from the group consisting of: a growth factor from FGF family, a SHH pathway inhibitor, a RA signaling pathway activator, a protein kinase C activator, and a ROCK inhibitor.

Disclosed herein, in some aspects, is a method comprising differentiating a population of cells comprising Pdx1-negative, NKX6.1-negative primitive gut tube cell in a culture medium comprising about 0.01% (w/v) to about 0.5% (w/v) human serum albumin (HSA), thereby generating a cell cluster comprising Pdx1-positive, NKX6.1-negative pancreatic progenitor cells.

In some embodiments, at least about 60%, at least about 70%, or at least about 85% of cells in the cell cluster comprising the Pdx1-positive, NKX6.1-negative pancreatic progenitor cells are Pdx1-positive as measured by flow cytometry. In some embodiments, at least about 85% of cells in the cell cluster comprising the Pdx1-positive, NKX6.1-negative pancreatic progenitor cells are Pdx1-positive as measured by flow cytometry. In some embodiments, at most about 40%, at most about 30%, at most about 20%, or at most about 15% of cells in the cell cluster comprising the Pdx1-positive, NKX6.1-negative pancreatic progenitor cells are CDX2-positive cells as measured by flow cytometry. In some embodiments, at most about 15% of cells in the cell cluster comprising the Pdx1-positive, NKX6.1-negative pancreatic progenitor cells are CDX2-positive cells as measured by flow cytometry. In some embodiments, the culture medium further comprises a differentiation factor selected from the group consisting of: a BMP signaling pathway inhibitor, a growth factor from TGF-β superfamily, a growth factor from FGF family, a SHH pathway inhibitor, a RA signaling pathway activator, a protein kinase C activator, and a ROCK inhibitor. In some embodiments, the culture medium further comprises a BMP signaling pathway inhibitor and a growth factor from TGF-β superfamily.

Disclosed herein, in some aspects, is a method comprising: (a) culturing a population of cells comprising a primitive gut tube cell in a culture medium comprising a bone morphogenetic protein (BMP) signaling pathway inhibitor, a growth factor from transformation growth factor β (TGF-β) superfamily, and human serum albumin (HSA), thereby generating a cell cluster comprising a Pdx1-positive, NKX6.1-positive pancreatic progenitor cell; and (b) differentiating the cell cluster comprising the PDX1-positive, NKX6.1-positive pancreatic progenitor cell into a cell cluster comprising a non-native pancreatic β cell.

Disclosed herein, in some aspects, is a cell cluster comprising at least about 50% Pdx1-positive, NKX6.1-positive pancreatic progenitor cells, at most about 30% chromogranin A (CHGA)-positive cells, and at most about 30% CDX2-positive cells as measured by flow cytometry.

In some embodiments, the cell cluster comprises at most about 25% the CDX2-positive, NKX6.1-positive cells as measured by flow cytometry. In some embodiments, the cell cluster comprises at most about 20% the CDX2-positive, NKX6.1-positive cells as measured by flow cytometry. In some embodiments, the cell cluster comprises at most about 25% the CHGA-positive cells as measured by flow cytometry. In some embodiments, the cell cluster comprises at most about 10% the CHGA-positive cells as measured by flow cytometry. In some embodiments, the cell cluster comprises at most about 5% the CHGA-positive cells as measured by flow cytometry. In some embodiments, the cell cluster comprises at least about 60% the Pdx1-positive, NKX6.1-positive pancreatic progenitor cells as measured by flow cytometry. In some embodiments, the cell cluster comprises at least about 65% the Pdx1-positive, NKX6.1-positive pancreatic progenitor cells as measured by flow cytometry.

In some embodiments, further differentiation of the cell cluster results in a first cell cluster comprising non-native pancreatic β cells that has a higher glucose-stimulated insulin secretion (GSIS) stimulation index than a second cell cluster comprising the non-native pancreatic β cells differentiated from a comparable cell cluster comprising at least about 50% the Pdx1-positive, NKX6.1-positive pancreatic progenitor cells, and more than 30% the chromogranin A (CHGA)-positive cells or more than 30% the CDX2-positive cells as measured by flow cytometry.

Disclosed herein, in some aspects, is a composition comprising the cell cluster disclosed herein and a bone morphogenetic protein (BMP) signaling pathway inhibitor and a growth factor from transformation growth factor β (TGF-β) superfamily. In some embodiments, the inhibitor of BMP signaling pathway comprises DMH-1 or derivative thereof. In some embodiments, the composition comprises about 0.01 µM to about 10 µM, about 0.05 µM to about 5 βM, about 0.1 µM to about 1 µM, or about 0.15 µM to about 0.5 µM DMH-1. In some embodiments, the composition comprises about 0.25 µM DMH-1. In some embodiments, the growth factor from TGF-β superfamily comprises Activin A. In some embodiments, the composition comprises about 0.5 ng/mL to about 200 ng/mL, about 1 ng/mL to about 100 ng/mL, about 2 ng/mL to about 50 ng/mL, or about 5 ng/mL to about 30 ng/mL Activin A. In some embodiments, the composition comprises at least about 5 ng/mL or at least about 10 ng/mL Activin A. In some embodiments, the composition comprises about 20 ng/mL Activin A. In some embodiments, the composition further comprises a differentiation factor selected from the group consisting of: a growth factor from fibroblast growth factor (FGF) family, a Sonic Hedgehog (SHH) pathway inhibitor, a retinoic acid (RA) signaling pathway activator, a protein kinase C activator, and a Rho-associated protein kinase (ROCK) inhibitor. In some embodiments, the cell cluster is in a culture medium. In some embodiments, the composition further comprises about 0.01% (w/v) to about 0.5% (w/v) human serum albumin (HSA). In some embodiments, the composition further comprises about 0.05% (w/v) HSA.

Disclosed herein, in some aspects, is a cell cluster comprising at least about 60% Pdx1-positive, NKX6.1-negative pancreatic progenitor cells and at most about 40% CDX2-positive cells as measured by flow cytometry.

In some embodiments, the cell cluster comprises at least about 70% the Pdx1-positive, NKX6.1-negative pancreatic progenitor cells as measured by flow cytometry. In some embodiments, the cell cluster comprises at least about 85% the Pdx1-positive, NKX6.1-negative pancreatic progenitor cells as measured by flow cytometry. In some embodiments, the cell cluster comprises at most about 30% the CDX2-positive cells as measured by flow cytometry. In some embodiments, the cell cluster comprises at most about 20% the CDX2-positive cells as measured by flow cytometry. In some embodiments, the cell cluster comprises at most about 15% the CDX2-positive cells as measured by flow cytometry.

In some embodiments, further differentiation of the cell cluster results in a first cell cluster comprising non-native pancreatic β cells that has a higher glucose-stimulated insulin secretion (GSIS) stimulation index than a second cell cluster comprising the non-native pancreatic β cells differentiated from a comparable cell cluster comprising at least about 60% the Pdx1-positive, NKX6.1-negative pancreatic progenitor cells, and more than 40% the CDX2-positive cells as measured by flow cytometry.

Disclosed herein, in some aspects, is a composition comprising the cell cluster disclosed herein in a culture medium comprising human serum albumin. In some embodiments, the culture medium comprises about 0.01% (w/v) to about 0.5% (w/v) HSA. In some embodiments, the culture medium further comprises a differentiation factor selected from the group consisting of: a BMP signaling pathway inhibitor, a growth factor from TGF-β superfamily, a growth factor from FGF family, a SHH pathway inhibitor, a RA signaling pathway activator, a protein kinase C activator, and a ROCK inhibitor.

Disclosed herein, in some aspects, is a cell cluster comprising non-native pancreatic β cells, wherein the cell cluster is obtained from differentiation of primitive gut tube cells by contacting the primitive gut tube cells with a bone morphogenetic protein (BMP) signaling pathway inhibitor and a growth factor from transformation growth factor 3 (TGF-β) superfamily, and wherein the cell cluster has a higher number of the non-native pancreatic β cells per cubic micrometer as compared to a comparable cell cluster obtained from differentiation of primitive gut tube cells without the contacting.

In some embodiments, the cell cluster has at least about 1.1, 1.2, 1.3, 1.4, 1.5, or 1.6 fold an higher number of the non-native pancreatic β cells per cubic micrometer as compared to the comparable cell cluster.

Disclosed herein, in some aspects, is a cell cluster comprising non-native pancreatic β cells, wherein the cell cluster is obtained from differentiation of primitive gut tube cells by contacting the primitive gut tube cells with a bone morphogenetic protein (BMP) signaling pathway inhibitor and a growth factor from transformation growth factor 3 (TGF-β) superfamily, and wherein the cell cluster exhibits higher insulin secretion in response to glucose challenge as compared to a comparable cell cluster obtained from differentiation of primitive gut tube cells without the contacting.

In some embodiments, the cell cluster exhibits at least about 1.2, 1.5, 2, 2.5, 3, 3.5, 4, 4.5, or 5 fold higher an insulin secretion as compared to the comparable cell cluster. In some embodiments, the cell cluster exhibits a higher GSIS stimulation index as compared to the comparable cell cluster. In some embodiments, the GSIS stimulation index of the cell cluster is at least about 1.2 fold, at least about 1.5 fold, at least about 1.8 fold, at least about 2 fold, at least about 2.2 fold, at least about 2.4 fold, at least about 2.8 fold, or at least about 3 fold higher than that of the comparable cell cluster. In some embodiments, the GSIS stimulation index of the cell cluster comprising the non-native pancreatic β cells is at least about 3 fold higher than that of the comparable cell cluster. In some embodiments, the GSIS stimulation index is calculated as a ratio of insulin secretion in response to a first glucose concentration to insulin secretion in response to a second glucose concentration. In some embodiments, the first glucose concentration is about 10 to about 50 mM, and the second glucose concentration is about 1 mM to 5 mM. In some embodiments, the first glucose concentration is about 20 mM, and the second glucose concentration is about 2.8 mM. In some embodiments, the non-native pancreatic β cells exhibit an in vitro glucose-stimulated insulin secretion response when exposed to a glucose challenge. In some embodiments, the non-native pancreatic β cells exhibit an insulin secretion in response to a first concentration of $K^+$. In some embodiments, the cell cluster exhibits a higher insulin secretion as compared to the comparable cell cluster in response to a first concentration of $K^+$. In some embodiments, the cell cluster exhibits at least about 1.2 fold, at least about 1.5 fold, at least about 1.8 fold, at least about 2 fold, at least about 2.2 fold, at least about 2.4 fold, at least about 2.8 fold, at least about 3 fold, at least about 3.2 fold, at least about 3.4 fold, at least about 3.6 fold, at least about 3.8 fold, at least about 4 fold higher an insulin secretion as compared to the comparable cell cluster in response to a first concentration of $K^+$.

Disclosed herein, in some aspects, is a cell cluster comprising non-native pancreatic R cells produced according to the method disclosed herein.

Disclosed herein, in some aspects, is a pharmaceutical composition comprising a cell cluster comprising non-native pancreatic β cells produced according to the method disclosed herein.

Disclosed herein, in some aspects, is a pharmaceutical composition comprising the cell cluster disclosed herein.

Disclosed herein, in some aspects, is a device comprising the cell cluster disclosed herein or a cell cluster comprising non-native pancreatic β cells produced according to the method disclosed herein, wherein the device is configured to produce and release insulin when implanted into a subject.

In some embodiments, the device further comprises a semipermeable membrane, wherein the semipermeable membrane is configured to retain cells in the device and permit passage of insulin secreted by the cells. In some embodiments, the cells are encapsulated by the semipermeable membrane. In some embodiments, the semipermeable membrane is made of polysaccharide or polycation. In some embodiments, the semipermeable membrane is made of a material selected from the group consisting of: poly(lactide) (PLA), poly(glycolic acid) (PGA), poly(lactide-co-glycolide) (PLGA), other polyhydroxyacids, poly(caprolactone), polycarbonates, polyamides, polyanhydrides, polyphosphazene, polyamino acids, polyortho esters, polyacetals, polycyanoacrylates, polytetrafluoroethylene (PTFE), biodegradable polyurethanes, albumin, collagen, fibrin, polyamino acids, prolamines, alginate, agarose, agarose with gelatin, dextran, polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, polyethylene oxide, and any combinations thereof. In some embodiments, the semipermeable membrane comprises alginate. In some embodiments, the cell cluster is encapsulated in a microcapsule that comprises an alginate core surrounded by the semipermeable membrane.

Disclosed herein, in some aspects, is a method of treating a subject, comprising administering the subject with non-native pancreatic β cells produced according to the method disclosed herein, the cell cluster disclosed herein, the pharmaceutical composition disclosed herein, or the device disclosed herein.

In some embodiments, the subject has, or has an increased risk of developing a metabolic disorder. In some embodiments, the subject has diabetes selected from the group consisting of: Type I diabetes, Type II diabetes, and Type 1.5 diabetes.

Provided herein, in some embodiments, is a composition comprising a population of glucose-responsive insulin secreting cells, wherein the cells secrete a higher amount of insulin upon induction with KCl as compared to the amount of insulin secreted upon induction with glucose. In some embodiments, the population of glucose-responsive insulin secreting cells secrete at least 1.5 times, 2 times, 2.5 times, 3 times higher amount of insulin upon induction with KCl as compared to the amount of insulin secreted upon induction with glucose. In some embodiments, the population of glucose-responsive insulin secreting cells is contacted with an amount of a signaling factor.

In some embodiments, the signaling factor is provided in an amount sufficient to result in an increase in insulin production as compared to a corresponding composition not contacted with the signaling factor. In some embodiments, the increase is a 1.5, 2, 2.5, 3, 3.5, 4, 4.5, 5, 5.5, 6 or 7 fold increase.

Also provided herein, in some embodiments, is a composition comprising a population of glucose-responsive insulin secreting cells, wherein the cells secrete a higher amount of insulin upon induction with KCl and/or glucose, in the presence of a signaling factor as compared to comparable cells in the absence of the signaling factor. In some embodiments, the cells secrete higher amount of insulin in the presence of high glucose, but not in the presence of low glucose.

Also provided herein, in some embodiments, is a population of differentiated pancreatic progenitor cells, wherein the population comprises at least 60% pancreatic β cells as determined by flow cytometry. In some embodiments, the population comprises at least 65%, 70%, 75%, 80%, 85%, or 90% pancreatic β cells.

In some embodiments, the population comprises a higher percentage of pancreatic β cells upon being contacted with a predetermined basal medium component as compared to a comparable population not contacted with the basal medium component.

Also provided herein, in some embodiments, is a method comprising implanting in a subject a device comprising insulin producing cells, wherein the device releases insulin in an amount sufficient for a reduction of blood glucose levels in the subject. In some embodiments, the insulin producing cells are glucose responsive insulin producing cells. In some embodiments, the reduction of blood glucose levels in the subject results in an amount of glucose which is lower than the diabetes threshold. In some embodiments, the subject is a mammalian subject. In some embodiments, the mammalian subject is human. In some embodiments, the amount of glucose is reduced to lower than the diabetes threshold in 1, 2, 3, 4, 5, 6, 7, 8, 9, or 10 days after the implanting.

Also provided herein, in some embodiments, is a method of differentiating a population of progenitor cells into a population of pancreatic β cells in vitro comprising culturing the population of progenitor cells in suspension in a culture medium comprising a basal medium component wherein a percentage of the population of pancreatic β cells after differentiation is at least 60%, at least 70%, at least 80%, at least 90%, at least 95%, or at least 99%. In some embodiments, the population of progenitor cells is a population of embryonic stem cells. In some embodiments, the population of progenitor cells comprises a subpopulation of Oct4 expressing cells. In some embodiments, a percentage of the subpopulation of Oct4 expressing cells is at least 90%. In some embodiments, the population of pancreatic β cells is a population of stem cell-derived β cells. In some embodiments, the culture medium comprises 0.1 L, 0.5 L, or 3 L of medium. In some embodiments, the population of pancreatic β cells after differentiation has a stimulation index of at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 or greater. In some embodiments, the stimulation index is determined in a condition comprising a signaling factor.

Provided herein, in some embodiments, is a composition of isolated pancreatic β cells produced according to the disclosed methods. Provided herein is a pharmaceutical composition of isolated pancreatic β cells produced according to the disclosed methods. Provided herein is a method of treating a subject, comprising administering the subject with isolated pancreatic R cells produced according to the disclosed methods.

Also disclosed herein, in some embodiments, is a composition comprising a population of cells or cell cluster that comprises at least about 20%, 30%, 40%, or 50% NKX6.1$^+$/C-peptide$^+$ cells. In some embodiments, the population of cells or cell cluster comprises at least about 40%, 50%, 60%, 70%, 80%, or 85% NKX6.1$^+$ cells. In some embodiments, the population of cells or cell cluster comprises at least about 30%, 40%, 50%, or 55% C-peptide+ cells. In some embodiments, the population of cells or cell cluster comprises at least about 40%, 50%, 60%, 70%, 80%, 85%, 90%, or 95% CHGA$^+$ cells.

In some aspects, the disclosure relates to compositions and methods to scale up islet cell production. In some embodiments, the culture of stem cell can be scaled to up to 0.1 L, up to 0.2 L, up to 0.5 L, up to 1 L, up to 1.5 L, up to 2 L, up to 2.5 L, up to 3 L, up to 3.5 L, up to 4 L, up to 4.5 L, or up to 5 L. In some embodiments, the culture of stem cell can be scaled to up to 6 L, 7 L, 8 L, 9 L, or 10 L.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 4A and 4B depict a comparison of exemplary stem cell-derived β (SC-β) cells produced using 3 different protocols.

FIG. 5 depicts images of exemplary SC-β cells and natural pancreatic islet cells.

FIG. 9A depicts a cell image of an exemplary 0.1 L culture of SC-β cells.

FIG. 9B depicts a cell image of an exemplary 0.5 L culture of SC-β cells.

FIG. 9C depicts a cell image of an exemplary 3.0 L culture of SC-β cells.

FIG. 9D depicts fold expansion of exemplary 0.1 L, 0.5 L, and 3 L cultures of SC-β cells.

FIG. 9E depicts percentage of Oct4 expressing cells in the example 0.1 L, 0.5 L, and 3 L cultures of SC-β cells.

DETAILED DESCRIPTION

Figure 1:
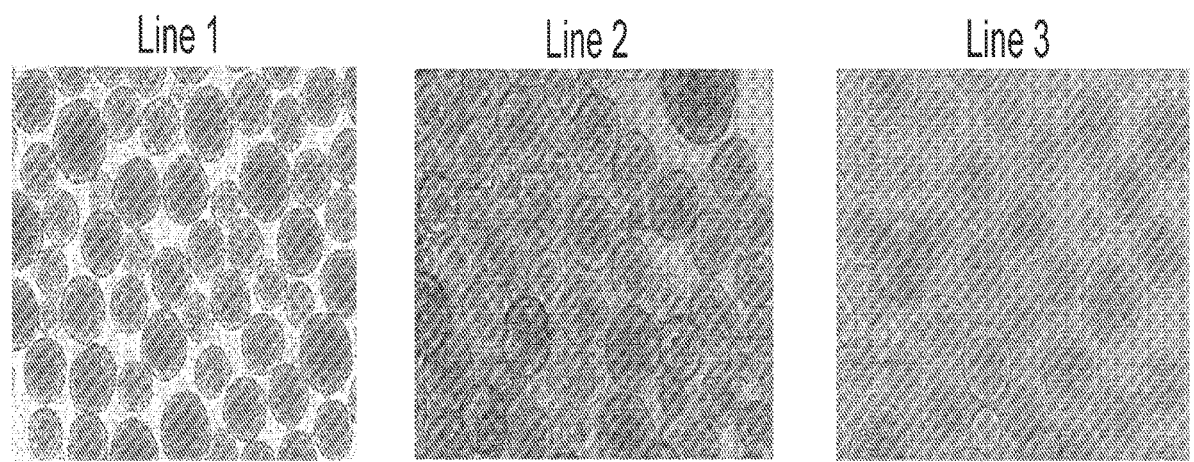
FIG. 1 depicts three exemplary candidate cell lines for islet cell production.

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the present disclosure can also be implemented in a single embodiment.

Definitions

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an," and "the" include plural referents unless the context clearly dictates otherwise.

Use of the term "including" as well as other forms, such as "include," "includes," and "included," is not limiting.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "diabetes" and its grammatical equivalents as used herein can refer to is a disease characterized by high blood sugar levels over a prolonged period. For example, the term "diabetes" and its grammatical equivalents as used herein can refer to all or any type of diabetes, including, but not limited to, type 1, type 2, cystic fibrosis-related, surgical, gestational diabetes, and mitochondrial diabetes. In some cases, diabetes can be a form of hereditary diabetes.

The term "endocrine cell(s)," if not particularly specified, can refer to hormone-producing cells present in the pancreas of an organism, such as "islet," "islet cells," "islet equivalent," "islet-like cells," "pancreatic islets" and their grammatical equivalents. In an embodiment, the endocrine cells can be differentiated from pancreatic progenitor cells or precursors. Islet cells can comprise different types of cells, including, but not limited to, pancreatic α cells, pancreatic β cells, pancreatic δ cells, pancreatic F cells, and/or pancreatic F cells. Islet cells can also refer to a group of cells, cell clusters, or the like.

The terms "progenitor" and "precursor" cell are used interchangeably herein and can refer to cells that have a cellular phenotype that is more primitive (e.g., is at an earlier step along a developmental pathway or progression than is a fully differentiated cell) relative to a cell which it can give rise to by differentiation. Often, progenitor cells can also have significant or very high proliferative potential. Progenitor cells can give rise to multiple distinct differentiated cell types or to a single differentiated cell type, depending on the developmental pathway and on the environment in which the cells develop and differentiate.

A "precursor thereof" as the term related to an insulin-positive endocrine cell can refer to any cell that is capable of differentiating into an insulin-positive endocrine cell, including for example, a pluripotent stem cell, a definitive endoderm cell, a primitive gut tube cell, a pancreatic progenitor cell, or endocrine progenitor cell, when cultured under conditions suitable for differentiating the precursor cell into the insulin-positive endocrine cell.

The terms "stem cell-derived β cell," "SC-β cell," "functional β cell," "functional pancreatic β cell," "mature SC-β cell," and their grammatical equivalents can refer to cells (e.g., non-native pancreatic β cells) that display at least one marker indicative of a pancreatic β cell (e.g., PDX-1 or NKX6.1), expresses insulin, and display a glucose stimulated insulin secretion (GSIS) response characteristic of an endogenous mature β cell. In some embodiments, the terms "SC-β cell" and "non-native β cell" as used herein are interchangeable. In some embodiments, the "SC-β cell" comprises a mature pancreatic cell. It is to be understood that the SC-β cells need not be derived (e.g., directly) from stem cells, as the methods of the disclosure are capable of deriving SC-β cells from any insulin-positive endocrine cell or precursor thereof using any cell as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc, as the invention is not intended to be limited in this manner). In some embodiments, the SC-β cells exhibit a response to multiple glucose challenges (e.g., at least one, at least two, or at least three or more sequential glucose challenges). In some embodiments, the response resembles the response of endogenous islets (e.g., human islets) to multiple glucose challenges. In some embodiments, the morphology of the SC-β cell resembles the morphology of an endogenous β cell. In some embodiments, the SC-β cell exhibits an in vitro GSIS response that resembles the GSIS response of an endogenous β cell. In some embodiments, the SC-β cell exhibits an in vivo GSIS response that resembles the GSIS response of an endogenous β cell. In some embodiments, the SC-β cell exhibits both an in vitro and in vivo GSIS response that resembles the GSIS response of an endogenous β cell. The GSIS response of the SC-β cell can be observed within two weeks of transplantation of the SC-β cell into a host (e.g., a human or animal). In some embodiments, the SC-β cells package insulin into secretory granules. In some embodiments, the SC-β cells exhibit encapsulated crystalline insulin granules. In some embodiments, the SC-β cells exhibit a stimulation index of greater than 1. In some embodiments, the SC-β cells exhibit a stimulation index of greater than 1.1. In some embodiments, the SC-β cells exhibit a stimulation index of greater than 2. In some embodiments, the SC-β cells exhibit cytokine-induced apoptosis in response to cytokines. In some embodiments, insulin secretion from the SC-β cells is enhanced in response to known antidiabetic drugs (e.g., secretagogues). In some embodiments, the SC-β cells are monohormonal. In some embodiments, the SC-β cells do not abnormally co-express other hormones, such as glucagon, somatostatin or pancreatic polypeptide. In some embodiments, the SC-β cells exhibit a low rate of replication. In some embodiments, the SC-β cells increase intracellular Ca2+ in response to glucose.

As used herein, the term "insulin producing cell" and its grammatical equivalent can refer to a cell differentiated from a pancreatic progenitor, or precursor thereof, which secretes insulin. An insulin-producing cell can include pancreatic β cell as that term is described herein, as well as pancreatic j-like cells (e.g., insulin-positive endocrine cells) that synthesize (e.g., transcribe the insulin gene, translate the pro-insulin mRNA, and modify the proinsulin mRNA into the insulin protein), express (e.g., manifest the phenotypic trait carried by the insulin gene), or secrete (release insulin into the extracellular space) insulin in a constitutive or inducible manner. A population of insulin producing cells, e.g., produced by differentiating insulin-positive, endocrine cells or a precursor thereof into SC-β cells according to the methods of the present disclosure can be pancreatic β cell or (β-like cells (e.g., cells that have at least one, or at least two least two) characteristic of an endogenous β cell and exhibit a glucose stimulated insulin secretion (GSIS) response that resembles an endogenous adult β cell. The population of insulin-producing cells, e.g., produced by the methods as disclosed herein can comprise mature pancreatic β cell or SC-β cells, and can also contain non-insulin-producing cells (e.g. cells of cell like phenotype with the exception they do not produce or secrete insulin).

The terms "insulin-positive j-like cell," "insulin-positive endocrine cell," and their grammatical equivalents can refer to cells (e.g., pancreatic endocrine cells) that displays at least one marker indicative of a pancreatic β cell and also expresses insulin but lack a glucose stimulated insulin secretion (GSIS) response characteristic of an endogenous β cell.

The term "β cell marker" refers to, without limitation, proteins, peptides, nucleic acids, polymorphism of proteins and nucleic acids, splice variants, fragments of proteins or nucleic acids, elements, and other analyte which are specifically expressed or present in pancreatic β cells. Exemplary β cell markers include, but are not limited to, pancreatic and duodenal homeobox 1 (Pdx1) polypeptide, insulin, c-peptide, amylin, E-cadherin, Hnf3β, PCI/3, B2, Nkx2.2, GLUT2, PC2, ZnT-8, Isl1, Pax6, Pax4, NeuroD, 1 Inflb, Hnf-6, Hnf-3beta, and MafA, and those described in Zhang et al., Diabetes. 50(10):2231-6 (2001).

The term "pancreatic endocrine marker" can refer to without limitation, proteins, peptides, nucleic acids, poly- morphism of proteins and nucleic acids, splice variants, fragments of proteins or nucleic acids, elements, and other analyte which are specifically expressed or present in pancreatic endocrine cells. Exemplary pancreatic endocrine cell markers include, but are not limited to, Ngn-3, NeuroD, and Islet-1.

The term "pancreatic progenitor," "pancreatic endocrine progenitor," "pancreatic precursor," "pancreatic endocrine precursor" and their grammatical equivalents are used interchangeably herein and can refer to a stem cell which is capable of becoming a pancreatic hormone expressing cell capable of forming pancreatic endocrine cells, pancreatic exocrine cells or pancreatic duct cells. These cells are committed to differentiating towards at least one type of pancreatic cell, e.g. β cells that produce insulin; a cells that produce glucagon; δ cells (or D cells) that produce somatostatin; and/or F cells that produce pancreatic polypeptide. Such cells can express at least one of the following markers: NGN3, NKX2.2, NeuroD, ISL-1, Pax4, Pax6, or ARX.

The term "Pdx1-positive pancreatic progenitor" as used herein can refer to a cell which is a pancreatic endoderm (PE) cell which has the capacity to differentiate into SC-β cells, such as pancreatic β cells. A Pdx1-positive pancreatic progenitor expresses the marker Pdx1. Other markers include, but are not limited to Cdcp1, or Ptf1a, or HNF6 or NRx2.2. The expression of Pdx1 may be assessed by any method known by the skilled person such as immunochemistry using an anti-Pdx1 antibody or quantitative RT-PCR. In some cases, a Pdx1-positive pancreatic progenitor cell lacks expression of NKX6.1. In some cases, a Pdx1-positive pancreatic progenitor cell can also be referred to as Pdx1-positive, NKX6.1-negative pancreatic progenitor cell due to its lack of expression of NKX6.1.

The term "Pdx1-positive, NKX6.1-positive pancreatic progenitor" as used herein can refer to a cell which is a pancreatic endoderm (PE) cell which has the capacity to differentiate into insulin-producing cells, such as pancreatic β cells. A Pdx1-positive, NKX6.1-positive pancreatic progenitor expresses the markers Pdx1 and NKX6.1. Other markers include, but are not limited to Cdcp1, or Ptf1a, or HNF6 or NRx2.2. The expression of NKX6.1 may be assessed by any method known by the skilled person such as immunochemistry using an anti-NKX6.1 antibody or quantitative RT-PCR. In some cases, NKX6.1 protein or gene can also be referred to as "NKX6-1" protein or gene.

The term "Ngn3-positive endocrine progenitor" as used herein can refer to precursors of pancreatic endocrine cells expressing the transcription factor Neurogenin-3 (Ngn3). Progenitor cells are more differentiated than multipotent stem cells and can differentiate into only few cell types. In particular, Ngn3-positive endocrine progenitor cells have the ability to differentiate into the five pancreatic endocrine cell types (a, f, 6, F and PP). The expression of Ngn3 may be assessed by any method known by the skilled person such as immunochemistry using an anti-Ngn3 antibody or quantitative RT-PCR.

The terms "NeuroD" and "NeuroD1" are used interchangeably and identify a protein expressed in pancreatic endocrine progenitor cells and the gene encoding it.

The term "differentiated cell" or its grammatical equivalents is meant any primary cell that is not, in its native form, pluripotent as that term is defined herein. Stated another way, the term "differentiated cell" can refer to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell leads to the pancreatic pathway, where ~98% of the cells become exocrine, ductular, or matrix cells, and ~2% become endocrine cells. Early endocrine cells are islet progenitors, which can then differentiate further into insulin-producing cells (e.g. functional endocrine cells) which secrete insulin, glucagon, somatostatin, or pancreatic polypeptide. Endoderm cells can also be differentiate into other cells of endodermal origin, e.g. lung, liver, intestine, thymus etc.

As used herein, the term "somatic cell" can refer to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro. Unless otherwise indicated the methods for converting at least one insulin-positive endocrine cell or precursor thereof to an insulin-producing, glucose responsive cell can be performed both in vivo and in vitro (where in vivo is practiced when at least one insulin-positive endocrine cell or precursor thereof are present within a subject, and where in vitro is practiced using an isolated at least one insulin-positive endocrine cell or precursor thereof maintained in culture).

As used herein, the term "adult cell" can refer to a cell found throughout the body after embryonic development.

The term "endoderm cell" as used herein can refer to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of the respiratory and digestive tracts (e.g. the intestine), the liver and the pancreas.

The term "a cell of endoderm origin" as used herein can refer to any cell which has developed or differentiated from an endoderm cell. For example, a cell of endoderm origin includes cells of the liver, lung, pancreas, thymus, intestine, stomach and thyroid. Without wishing to be bound by theory, liver and pancreas progenitors (also referred to as pancreatic progenitors) are develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein can refer to a cell differentiated from an endoderm cell and which can be differentiated into a SC-β cell (e.g., a pancreatic β cell). A definitive endoderm cell expresses the marker Sox17. Other markers characteristic of definitive endoderm cells include, but are not limited to MIXL2, GATA4, HNF3b, GSC, FGF17, VWF, CALCR, FOXQ1, CXCR4, Cerberus, OTX2, goosecoid, C-Kit, CD99, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker Pdx1 (e.g. they are Pdx1-negative). Definitive endoderm cells have the capacity to differentiate into cells including those of the liver, lung, pancreas, thymus, intestine, stomach and thyroid. The expression of Sox17 and other markers of definitive endoderm may be assessed by any method known by the skilled person such as immunochemistry, e.g., using an anti-Sox17 antibody, or quantitative RT-PCR.

The term "pancreatic endoderm" can refer to a cell of endoderm origin which is capable of differentiating into multiple pancreatic lineages, including pancreatic β cells, but no longer has the capacity to differentiate into non-pancreatic lineages.

The term "primitive gut tube cell" or "gut tube cell" as used herein can refer to a cell differentiated from an endoderm cell and which can be differentiated into a SC-β cell (e.g., a pancreatic β cell). A primitive gut tube cell expresses at least one of the following markers: HNP1-β, HNF3-β or HNF4-α. Primitive gut tube cells have the capacity to differentiate into cells including those of the lung, liver, pancreas, stomach, and intestine. The expression of HNF1-β and other markers of primitive gut tube may be assessed by any method known by the skilled person such as immunochemistry, e.g., using an anti-HNF1-β antibody.

The term "stem cell" as used herein, can refer to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" can refer to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retro-differentiation" by persons of ordinary skill in the art. As used herein, the term "pluripotent stem cell" includes embryonic stem cells, induced pluripotent stem cells, placental stem cells, etc.

The term "pluripotent" as used herein can refer to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g., iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and can refer to a pluripotent stem cell artificially derived (e.g., induced or by complete reversal) from a non-pluripotent cell, typically an adult somatic cell, for example, by inducing a forced expression of one or more genes.

The term "phenotype" can refer to one or a number of total biological characteristics that define the cell or organism under a particular set of environmental conditions and factors, regardless of the actual genotype.

The terms "subject," "patient," or "individual" are used interchangeably herein, and can refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject can refer to that specific animal. The "non-human animals" and "non-human mammals" as used interchangeably herein, includes mammals such as rats, mice, rabbits, sheep, cats, dogs, cows, pigs, and non-human primates.

The term "subject" also encompasses any vertebrate including but not limited to mammals, reptiles, amphibians and fish. However, advantageously, the subject is a mammal such as a human, or other mammals such as a domesticated mammal, e.g., dog, cat, horse, and the like, or production mammal, e.g. cow, sheep, pig, and the like. "Patient in need thereof" or "subject in need thereof" is referred to herein as a patient diagnosed with or suspected of having a disease or disorder, for instance, but not restricted to diabetes.

"Administering" used herein can refer to providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise the cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The terms "treat," "treating," "treatment," and their grammatical equivalents, as applied to an isolated cell, include subjecting the cell to any kind of process or condition or performing any kind of manipulation or procedure on the cell. As applied to a subject, the terms can refer to providing medical or surgical attention, care, or management to an individual. The individual is usually ill or injured, or at increased risk of becoming ill relative to an average member of the population and in need of such attention, care, or management.

As used herein, the term "treating" and "treatment" can refer to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

The term "therapeutically effective amount," therapeutic amount", or its grammatical equivalents can refer to an amount effective, at dosages and for periods of time necessary, to achieve a desired therapeutic result. The therapeutically effective amount can vary according to factors such as the disease state, age, sex, and weight of the individual and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," e.g., the effect completely or partially prevents a disease or symptom thereof. A "prophylactically effective amount" can refer to an amount effective, at dosages and for periods of time necessary, to achieve a desired prophylactic result (e.g., prevention of disease onset).

Some numerical values disclosed throughout are referred to as, for example, "X is at least or at least about 100; or 200 [or any numerical number]." This numerical value includes the number itself and all of the following:
 i) X is at least 100;
 ii) X is at least 200;
 iii) X is at least about 100; and
 iv) X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, "X is administered on or on about day 1 to 2; or 2 to 3 [or any numerical range]." This range includes the numbers themselves (e.g., the endpoints of the range) and all of the following:
 i) X being administered on between day 1 and day 2;
 ii) X being administered on between day 2 and day 3;
 iii) X being administered on between about day 1 and day 2;
 iv) X being administered on between about day 2 and day 3;
 v) X being administered on between day 1 and about day 2;
 vi) X being administered on between day 2 and about day 3;
 vii) X being administered on between about day 1 and about day 2; and
 viii) X being administered on between about day 2 and about day 3.

I. Overview

Implantation of islet cells can replace dead or dysfunctional β cells in diabetes patients and potentially cure diabetes. Provided herein are compositions and methods to produce stem-cell-derived β cells to be used for implantation.

Aspects of the present disclosure relates to methods of differentiating a primitive gut tube cell into a Pdx1-positive pancreatic β cell. In some cases, the method comprises contacting the primitive gut tube cell with a composition comprising a bone morphogenetic protein (BMP) signaling pathway inhibitor and a growth factor from transformation growth factor β (TGF-β) superfamily. In some cases, the composition further comprises one or more additional differentiation factors, which include, but not limited to, a growth factor from fibroblast growth factor (FGF) family, a Sonic Hedgehog (SHH) pathway inhibitor, a retinoic acid (RA) signaling pathway activator, a protein kinase C (PKC) activator, and a Rho-associated protein kinase (ROCK) inhibitor.

In some cases, a method provided herein comprises generating a population of cells or cell cluster that comprises a Pdx1-positive pancreatic progenitor cell by contacting a population of cells comprising a primitive gut tube cell with a first composition comprising a BMP signaling pathway inhibitor and a growth factor from TGF-β superfamily, wherein the primitive gut tube cell is differentiated in the Pdx1-positive, NKX6.1-positive pancreatic progenitor cell. In some cases, the contacting takes place for about 1 day, 2 days, or 3 days. In some cases, the contacting takes place about 1 day. In some cases, the primitive gut tube cell is differentiated into a Pdx1-positive, NKX6.1-negative pancreatic progenitor cell by contacting with a composition comprising BMP signaling pathway inhibitor and a growth factor from TGF-β superfamily. In some cases, the generating step further comprises differentiating the Pdx1-positive, NKX6.1-negative pancreatic progenitor cell into a Pdx1-positive, NKX6.1-positive pancreatic progenitor cell by contacting the Pdx1-positive, NKX6.1-negative pancreatic progenitor cell with a second composition comprising one or more differentiation factors, which include, but not limited to, a growth factor from TGF-β superfamily, a growth factor from FGF family, a SHH pathway inhibitor, a RA signaling pathway activator, and a ROCK inhibitor. In some cases, the second composition does not comprise BMP signaling pathway inhibitor.

In some cases, the method provided herein can obtain a population of cells or cell cluster that comprises at most about 30%, at most about 25%, at most about 20%, at most about 15%, at most about 10%, at most about 5%, at most about 4%, at most about 3%, at most about 2%, or at most about 1% CHGA-positive cells by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about at most about 25%, at most about 20%, at most about 15%, or at most about 10% CDX2-positive cells as measured by flow cytometry by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about 30% CHGA-positive cells and at most about 30% CDX2-positive cells by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about 20% CHGA-positive cells and at most about 5% CDX2-positive cells by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about 15% CHGA-positive cells and at most about 3% CDX2-positive cells by differentiating a population of cells comprising primitive gut tube cells into a population of cells or cell cluster comprising Pdx1-positive, NKX6.1-positive pancreatic progenitor cells.

In some cases, the BMP signaling pathway inhibitor provided herein comprises DMH-1, derivative, analogue, or variant thereof. In some embodiments, the BMP signaling pathway provided herein comprises DMH-1. In some embodiments, the method comprises contacting primitive gut tube cell with about 0.01 µM to about 10 µM, about 0.05 µM to about 5 µM, about 0.1 µM to about 1 µM, or about 0.15 µM to about 0.5 µM DMH-1. In some embodiments, the method comprises contacting primitive gut tube cell with about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.4, 0.42, 0.45, 0.48, 0.50, 0.55, 0.60, 0.65, 0.70, 0.75, 0.80, 0.85, 0.90, 0.95, 1, 1.2, 1.4, 1.5, 1.6, 1.7, 1.8, 2.0, 4.0, 6.0, 8.0, or 10 µM. In some embodiments, the method comprises contacting primitive gut tube cell with about 0.25 βM. In some cases, the BMP signaling pathway inhibitor as used in differentiating the primitive gut tube cell does not comprise LDN193189.

In some cases, the methods provided herein comprise generating a population of cells or cell cluster that comprise a Pdx1-positive, NKX6.1-positive pancreatic progenitor cell by contacting a population of cells comprising a primitive gut tube cell with DMH-1, or derivative, analogue, or variant thereof.

Figure 15:
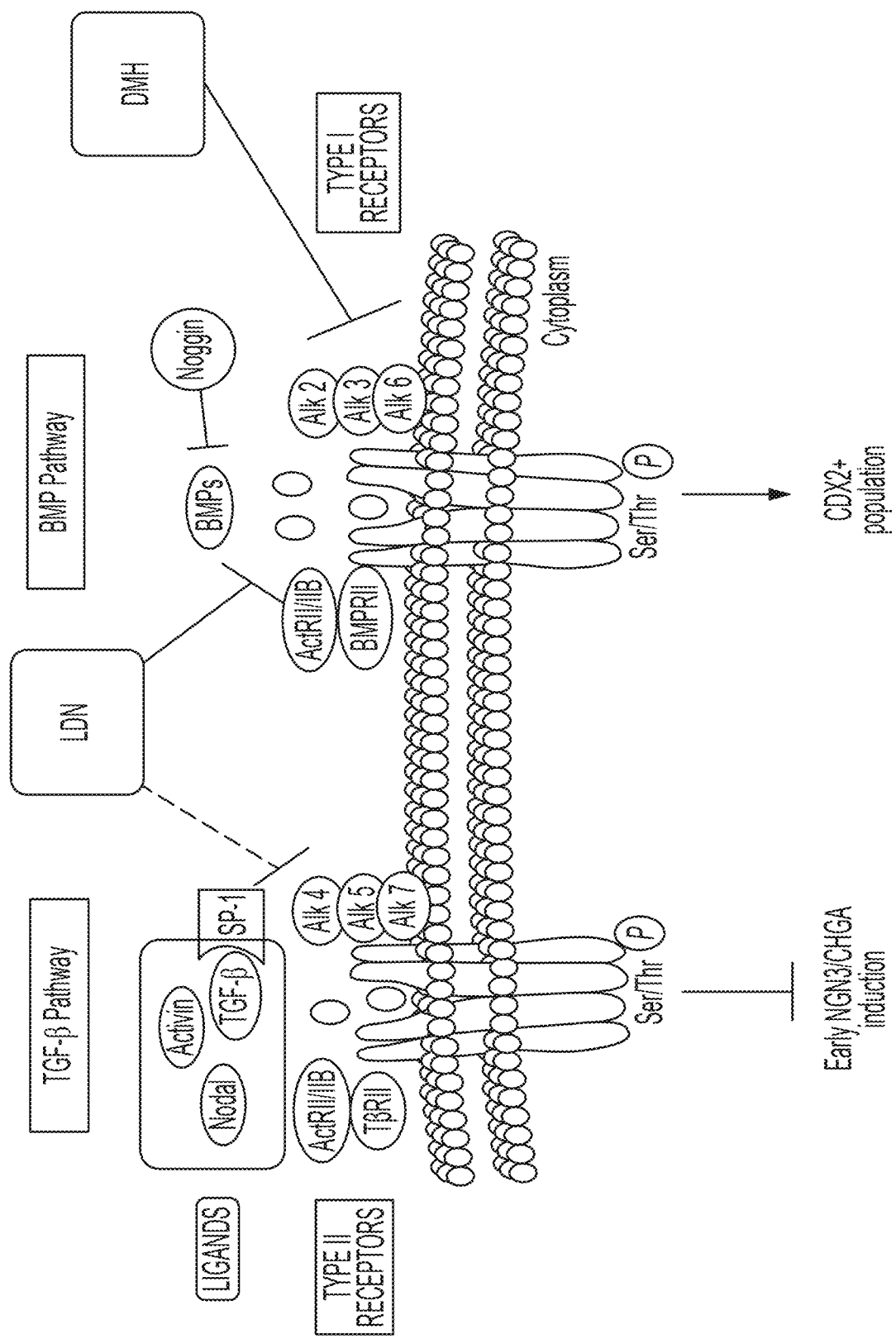
FIG. 15 is a schematic illustrating one example of the effects of exemplary BMP signaling pathway inhibitors LDN193189 ("LDN" in the figure) and DMH-1.

Without wishing to be bound to a particular theory, in some embodiments of the methods disclosed herein, during differentiation of a primitive gut tube cell to a Pdx1-positive pancreatic progenitor cell, inhibition of BMP signaling pathway can contribute to reduction in generation of off-target cells, for instance, cells of intestine lineage or cells positive for CDX2 gene expression. On the other hand, in some cases, during differentiation of a primitive gut tube cell to a Pdx1-positive pancreatic progenitor cell or Pdx1-positive, NKX6.1-positive pancreatic progenitor cell, activation of Type II receptor-mediated TGF-β signaling pathway can contribute to reduction of early induction of neurogenin 3 (Ngn3) or chromogranin A (CHGA), which can, in some cases, lead to generation of polyhormonal cells rather than mature SC-β cells, which, in some cases, are monohormonal, e.g., secreting only insulin, but not other pancreatic hormones like somatostatin or glucagon. There can be cross-talk between BMP signaling pathway and TGF-β signaling pathway. In some cases, an inhibitor of BMP signaling pathway can have side effect, for instance, blockage of, among others, Type II receptor-mediated TGF-β signaling pathway. The inhibition of Type II receptor-mediated TGF-β signaling pathway, as illustrated in FIG. 15, for instance by a relatively less selective BMP signaling pathway inhibitor, LDN193189, can lead to early NGN3/CHGA induction, thereby generation of polyhormonal cells. Without wishing to be bound by a certain theory, in some cases, use of a highly selective BMP signaling pathway inhibitor, for instance, DMH-1 or its derivate, analogue, or variant, can have less inhibitory effect on Type II receptor-mediated TGF-β signaling pathway. In some other cases, without wishing to be bound to a particular theory, co-incubation with a growth factor from TGF-β superfamily together with a BMP signaling pathway inhibitor can result in selective inhibition of BMP signaling pathway, while maintaining relatively high activation level of Type II receptor-mediated TGF-β signaling pathway. In some cases, co-incubation with a growth factor from TGF-β superfamily together with a BMP signaling pathway inhibitor result in reduced generation of off-target cells, e.g., CDX2-positive cells, as well as reduced generation of polyhormonal cells, for instance, as a result of early induction of NGN3 or CHGA in the cells differentiated from the primitive gut tube cells.

Aspects of the present disclosure relates to a method of generating pancreatic β cells, e.g., SC-β cells, which comprises differentiating progenitor cells (e.g., stem cells like iPSC cells, definitive endoderm cells, primitive gut tube cells, Pdx1-positive pancreatic progenitor cells, NKX6.1-positive pancreatic progenitor cells, or insulin-positive endocrine cells) in a xeno-free culture medium. A xeno-free medium for culturing cells and/or cell clusters of originated from an animal can have no product from other animals. In some cases, a xeno-free medium for culturing human cells and/or cell clusters can have no products from any non-human animals. For example, a xeno-free medium for culturing human cells and/or cell clusters can comprise human serum albumin (HSA) or human platelet lysate (PLT) instead of fetal bovine serum (FBS) or bovine serum albumin (BSA).

In some embodiments, a method provided herein comprises generating pancreatic β cells, e.g., SC-β cells, by differentiating progenitor cells (e.g., stem cells like iPSC cells, definitive endoderm cells, primitive gut tube cells, Pdx1-positive pancreatic progenitor cells, NKX6.1-positive pancreatic progenitor cells, or insulin-positive endocrine cells) in a culture medium lacking serum albumin. In some cases, a population of cells or cell cluster comprising pancreatic β cells generated by a method provided herein that does not use serum albumin or uses HSA in the culture medium can have significant improvement as compared to a population of cells or cell cluster comprising pancreatic β cells generated by an otherwise identical method but using BSA instead. The improvement can include higher percentage of pancreatic β cells in the final cell population obtained, higher GSIS responses (e.g., more insulin release in response to glucose challenge), higher GSIS stimulation index, more homogeneity of distribution of pancreatic β cells in the cell cluster generated, or any combination thereof.

In some embodiments, a method provided herein comprises differentiating a population of cells comprising a stem cell, e.g., a hES cell or iPS cell, in a culture medium comprising human serum albumin (HSA). In some cases, the stem cell is differentiated into a definitive endoderm cell. In some embodiments, a method provided herein comprises differentiating a population of cells comprising a definitive endoderm cell in a culture medium comprising human serum albumin (HSA). In some cases, the definitive endoderm cell is differentiated into a primitive gut tube cell. In some embodiments, a method provided herein comprises differentiating a population of cells comprising a primitive gut tube cell in a culture medium comprising human serum albumin (HSA). In some cases, the primitive gut tube cell is differentiated into a Pdx1-positive pancreatic progenitor cell (e.g., Pdx1-positive, NKX6.1-negative pancreatic progenitor cell or Pdx1-positive, NKX6.1-positive pancreatic progenitor cell). In some embodiments, a method provided herein comprises differentiating a population of cells comprising a Pdx1-positive, NKX6.1-negative pancreatic progenitor cell in a culture medium comprising human serum albumin (HSA). In some case, the Pdx1-positive, NKX6.1-negative pancreatic progenitor cell is differentiated into a Pdx1-positive, NKX6.1-positive pancreatic progenitor cell. In some embodiments, a method provided herein comprises differentiating a population of cells comprising a Pdx1-positive, NKX6.1-positive pancreatic progenitor cell in a culture medium comprising human serum albumin (HSA).

In some cases, the Pdx1-positive, NKX6.1-positive pancreatic progenitor cell is differentiated into an insulin-positive endocrine cell. In some embodiments, a method provided herein comprises differentiating a population of cells comprising an insulin-positive endocrine cell in a culture medium comprising human serum albumin (HSA). In some cases, the insulin-positive endocrine cell is differentiated into a pancreatic β cell, e.g., SC-β cell.

In some embodiments, the methods provided herein comprise use of culture medium comprising about 0.001% (w/v) to about 5% (w/v), about 0.005% (w/v) to about 4% (w/v), about 0.01% (w/v) to about 3% (w/v), about 0.02% (w/v) to about 2.5% (w/v), about 0.03% (w/v) to about 2% (w/v), about 0.04% (w/v) to about 1% (w/v), about 0.045% (w/v) to about 0.5% (w/v), or about 0.05% (w/v) to about 0.1% (w/v) HSA. In some embodiments, the methods provided herein comprise use of culture medium comprising about 0.001%, 0.002%, 0.0025%, 0.005%, 0.0075%, 0.01%, 0.0125%, 0.015%, 0.0175%, 0.02%, 0.0225%, 0.025%, 0.0275%, 0.03%, 0.0325%, 0.035%, 0.0375%, 0.04%, 0.0425%, 0.045%, 0.0475%, 0.05%, 0.0525%, 0.055%, 0.575%, 0.06%, 0.0625%, 0.065%, 0.0675%, 0.07%, 0.0725%, 0.075%, 0.0775%, 0.08%, 0.085%, 0.09%, 0.1%, 0.12%, 0.15%, 0.2%, 0.25%, 0.3%, 0.4%, 0.5%, 0.6%, 0.7%, 0.8%, 0.9%, 1%, 1.5%, 2%, 2.5%, 3%, or 4%, 5% (w/v) HSA. The term "w/v" is short for percentage of weight/volume or weight per volume. For instance, 1 mg HSA in 100 mL culture medium has a concentration of 1% (w/v).

In some cases, the method provided herein can obtain a population of cells or cell cluster that comprises at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, or at least about 95% Pdx1-positive cells by differentiating a population of cells comprising primitive gut tube cells into a population of cells or cell cluster comprising Pdx1-positive, NKX6.1-negative pancreatic progenitor cells. In some cases, the method provided herein can obtain a population of cells or cell cluster that comprises at most about 60%, at most about 50%, at most about 40%, at most about 35%, at most about 30%, at most about 25%, at most about 22%, at most about 20%, at most about 18%, at most about 15%, at most about 14%, at most about 13%, at most about 11%, at most about 12%, at most about 10%, or at most about 5% CDX2-positive cells by differentiating a population of cells comprising primitive gut tube cells into a population of cells or cell cluster comprising Pdx1-positive, NKX6.1-negative pancreatic progenitor cells.

Aspects of the disclosure relate to compositions and methods for generating stem cell-derived β (SC-β) cells (e.g., mature pancreatic β cells) from at least one insulin-positive endocrine cell or a precursor thereof (e.g., iPS cells, hESCs, definitive endoderm cells, primitive gut tube cells, PDX1-positive pancreatic progenitor cells, PDX1-positive, NKX6.1-positive pancreatic progenitor cells, Ngn3-positive endocrine progenitor cells, etc.), and SC-β cells produced by those compositions and methods for use in cell therapies, assays (e.g., drug screening), and various methods of treatment.

In some aspects, the disclosure provides methods and criteria to select stem cells for producing SC-β cells. In some embodiments, the stem cell is embryonic stem cell (ESC). In some embodiments, the stem cell is a cell expressing Oct4. In some embodiments, the starting stem cell culture comprises a percentage of Oct4 expressing cells of at least 80%, at least 85%, at least 90%, at least 95%, or 100%.

In some aspects, the disclosure relates to methods of identification of the SC-β cells that are detectable based on morphological criteria, without the need to employ a selectable marker, as well as functional characteristics, such as ability to express insulin, secrete insulin in response to one or more glucose challenges, exhibit a mature GSIS response, and organize in islets in pancreas in vivo, and typically have small spindle like cells of about 9-15 nm diameter.

In some aspects, the disclosure relates to methods of identifying basal medium components for stem cell differentiation. In some embodiments, the basal medium components can increase differentiation efficiency. In some embodiments, the basal medium components can increase the percentage of on-target progenitor cell population (e.g., SC-β cell population). In some embodiments, the percentage of on-target progenitor cell population produced by the disclosed methods is from 60% to 70%, from 70% to 80%, from 80% to 90%, or from to 100%. In some embodiments, the percentage of SC-β cell population produced by the disclosed methods is from 60% to 70%, from 70% to 80%, from 80% to 90%, or from to 100%. In some embodiments, the percentage of SC-β cell population produced by the disclosed methods is c In some aspects, the disclosure relates to compositions and methods of producing SC-β cells, resulting in 1.2 to 3 fold increase of percentage of SC-β cells compared with standard methods known in the art. In some embodiments, the fold increase is from 1.2 to 1.5, from 1.5 to 2, or from 2 to 2.5. The produced SC-β cells can exhibit activity comparable to endogenous (e.g. natural) β cells and exhibit stability after cryopreservation.

In some aspects, the disclosure relates to methods of identifying signaling factor that can improve SC-β cell activity (e.g. the ability to sense glucose and secrete insulin). Screening of candidate small molecules can be performed to identify useful signaling factors.

One example assay can be used to test signaling factors is the GSIS assay. In some embodiments, the SC-β cell exhibits a stimulation index of at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 or greater in the presence of a signaling factor.

II. SC-β Cells

The SC-β cells of the disclosure share many characteristic features of β cells which are important for normal β cell function. In some embodiments, the SC-β cell exhibits a glucose stimulated insulin secretion (GSIS) response in vitro. In some embodiments, the SC-β cell exhibits a GSIS response in vivo. In some embodiments, the SC-β cell exhibits in vitro and in vivo GSIS responses. In some embodiments, the GSIS responses resemble the GSIS responses of an endogenous mature pancreatic β cell. In some embodiments, the SC-β cell exhibits a GSIS response to at least one glucose challenge. In some embodiments, the SC-β cell exhibits a GSIS response to at least two sequential glucose challenges. In some embodiments, the SC-β cell exhibits a GSIS response to at least three sequential glucose challenges. In some embodiments, the GSIS responses resemble the GSIS response of endogenous human islets to multiple glucose challenges. In some embodiments, the GSIS response is observed immediately upon transplanting the cell into a human or animal. In some embodiments, the GSIS response is observed within approximately 24 hours of transplanting the cell into a human or animal. In some embodiments, the GSIS response is observed within approximately one week of transplanting the cell into a human or animal. In some embodiments, the GSIS response is observed within approximately two weeks of transplanting the cell into a human or animal. In some embodiments, the stimulation index of the cell as characterized by the ratio of insulin secreted in response to high glucose concentrations compared to low glucose concentrations is similar to the stimulation index of an endogenous mature pancreatic β cell. In some embodiments, the SC-β cell exhibits a stimulation index of greater than 1. In some embodiments, the SC-β cell exhibits a stimulation index of greater than or equal to 1. In some embodiments, the SC-β cell exhibits a stimulation index of greater than 1.1. In some embodiments, the SC-β cell exhibits a stimulation index of greater than or equal to 1.1. In some embodiments, the SC-β cell exhibits a stimulation index of greater than 2. In some embodiments, the SC-β cell exhibits a stimulation index of greater than or equal to 1. In some embodiments, the SC-β cell exhibits a stimulation index of at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 or greater.

Some embodiments of the present disclosure relate to cell compositions, such as cell cultures or cell populations, comprising SC-β cells, wherein the SC-β cells have been derived from at least one insulin-positive endocrine cell or a precursor thereof. In some embodiments, the cell compositions comprise insulin-positive endocrine cells. In some embodiments, the cell compositions comprise NKX6.1-pancreatic progenitor cells. In some embodiments, the cell compositions comprise PDX1-pancreatic progenitor cells. In some embodiments, the cell compositions comprise primitive gut tube cells. In some embodiments, the cell compositions comprise definitive endoderm cells.

In accordance with certain embodiments, the chemically induced SC-β cells are mammalian cells, and in a preferred embodiment, such SC-β cells are puma SC-β cells. In some embodiments, the insulin-positive endocrine cells have been derived from definitive endoderm cells e.g. human definitive endoderm stem cells. In accordance with certain embodiments, the chemically induced PDX1-positive pancreatic progenitors are mammalian cells, and in a preferred embodiment, such PDX1-positive pancreatic progenitors are human PDX1-positive pancreatic progenitors.

Other embodiments of the present disclosure relate to compositions, such as an isolated cell population or cell culture, comprising SC-β cells produced by the methods as disclosed herein. In some embodiments of the present disclosure relate to compositions, such as isolated cell populations or cell cultures, comprising chemically-induced SC-β cells produced by the methods as disclosed herein. In such embodiments, the SC-β cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the SC-β cells population. In some embodiments, the composition comprises a population of SC-β cells which make up more than about 90% of the total cells in the cell population, for example about at least 95%, or at least 96%, or at least 97%, or at least 98% or at least about 99%, or about at least 100% of the total cells in the cell population are SC-β cells.

Certain other embodiments of the present disclosure relate to compositions, such as an isolated cell population or cell cultures, comprise a combination of SC-β cells and insulin-positive endocrine cells or precursors thereof from which the SC-β cells were derived. In some embodiments, the insulin-positive endocrine cells from which the SC-β cells are derived comprise less than about 25%, less than about 20%, less than about 15%, less than about 10%, less than about 5%, less than about 4%, less than about 3%, less than about 2% or less than about 1% of the total cells in the isolated cell population or culture.

Additional embodiments of the present disclosure relate to compositions, such as isolated cell populations or cell cultures, produced by the processes described herein and which comprise chemically induced SC-β cells as the majority cell type. In some embodiments, the methods and processes described herein produces an isolated cell culture and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% SC-β cells.

In another embodiment, isolated cell populations or compositions of cells (or cell cultures) comprise human SC-β cells. In other embodiments, the methods and processes as described herein can produce isolated cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% SC-β cells. In preferred embodiments, isolated cell populations can comprise human SC-β cells. In some embodiments, the percentage of SC-β cells in the cell cultures or populations is calculated without regard to the feeder cells remaining in the culture.

Yet another aspect of the present disclosure relates to cell populations or compositions of cells (or cell cultures) that comprise at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% NKX6.1+/C-peptide+ cells. In some embodiments, the cell population or composition of cells as provided herein comprises at least about 20% NKX6.1+/C-peptide+ cells. In some embodiments, the cell population or composition of cells as provided herein comprises at least about 40% NKX6.1+/C-peptide+ cells. In some embodiments, the cell population or composition of cells as provided herein comprises at least about 50% NKX6.1+/C-peptide+ cells. In some embodiments, the cell population or composition of cells as provided herein comprises about 17.9% NKX6.1+/C-peptide+ cells. In some embodiments, the cell population or composition of cells as provided herein comprises about 41.5% NKX6.1+/C-peptide+ cells. In some embodiments, the cell population or composition of cells as provided herein comprises about 50.6% NKX6.1+/C-peptide+ cells.

In some embodiments, the cell population or composition of cells as provided herein comprises at least about 90%, at least about 89%, at least about 88%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% NKX6.1+ cells. In some embodiments, the cell population or composition of cells as provided herein comprises at least about 40% NKX6.1+ cells. In some embodiments, the cell population or composition of cells as provided herein comprises at least about 60% NKX6.1+ cells. In some embodiments, the cell population or composition of cells as provided herein comprises at least about 85% NKX6.1+ cells. In some embodiments, the cell population or composition of cells as provided herein comprises about 36.9% NKX6.1+ cells. In some embodiments, the cell population or composition of cells as provided herein comprises about 63.4% NKX6.1+ cells. In some embodiments, the cell population or composition of cells as provided herein comprises about 89.5% NKX6.1+ cells.

In some embodiments, the cell population or composition of cells as provided herein comprises at least about 55%, at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% C-peptide+ cells. In some embodiments, the cell population or composition of cells as provided herein comprises at least about 30% C-peptide+ cells. In some embodiments, the cell population or composition of cells as provided herein comprises at least about 55% C-peptide+ cells. In some embodiments, the cell population or composition of cells as provided herein comprises about 26.8% C-peptide+ cells. In some embodiments, the cell population or composition of cells as provided herein comprises about 57.7% C-peptide+ cells. In some embodiments, the cell population or composition of cells as provided herein comprises about 55.2% C-peptide+ cells.

In some embodiments, the cell population or composition of cells as provided herein comprises at least about 99%, at least about 98%, at least about 95%, at least about 90%, at least about 89%, at least about 88%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% Chromogranin A (CHGA)+ cells. In some embodiments, the cell population or composition of cells as provided herein comprises at least about 40% CHGA+ cells. In some embodiments, the cell population or composition of cells as provided herein comprises at least about 85% CHGA+ cells. In some embodiments, the cell population or composition of cells as provided herein comprises at least about 95% CHGA+ cells. In some embodiments, the cell population or composition of cells as provided herein comprises about 37.7% CHGA+ cells. In some embodiments, the cell population or composition of cells as provided herein comprises about 87.5% CHGA+ cells. In some embodiments, the cell population or composition of cells as provided herein comprises about 96.4% CHGA+ cells.

Still other embodiments of the present disclosure relate to compositions, such as isolated cell populations or cell cultures, comprising mixtures of SC-β cells and insulin-positive endocrine cells or precursors thereof from which they were differentiated from. For example, cell cultures or cell populations comprising at least about 5 SC-β cells for about every 95 insulin-positive endocrine cells or precursors thereof can be produced. In other embodiments, cell cultures or cell populations comprising at least about 95 SC-β cells for about every 5 insulin-positive endocrine cells or precursors thereof can be produced. Additionally, cell cultures or cell populations comprising other ratios of SC-β cells to insulin-positive endocrine cells or precursors thereof are contemplated. For example, compositions comprising at least about 1 SC-β cell for about every 1,000,000, or at least 100,000 cells, or at least 10,000 cells, or at least 1000 cells or 500, or at least 250 or at least 100 or at least 10 insulin-positive endocrine cells or precursors thereof can be produced.

In some aspects, the present disclosure provides a cell cluster comprising at least about 50% Pdx1-positive, NKX6.1-positive pancreatic progenitor cells, at most about 30%, 28%, 26%, 25%, 24%, 22%, 20%, 18%, 16%, 14%, 12%, 10%, 9%, 8%, 7%, 6%, 5%, 4%, 3%, or 2% chromogranin A (CHGA)-positive cells, and at most about 30%, 28%, 26%, 25%, 24%, 22%, 20%, 18%, 16%, or 15% CDX2-positive cells. In some cases, the cell cluster comprises at most about 20% the CDX2-positive, NKX6.1-positive cells. In some cases, the cell cluster comprises at most about 5% the CHGA-positive cells. In some embodiments, the cell cluster comprises at most about 20% the CDX2-positive, NKX6.1-positive cells and at most about 5% the CHGA-positive cells. In some embodiments, the cell cluster comprises at least about 60%, 62%, 64%, 65%, 68%, 70%, 72%, 74%, 76%, 78%, 80%, 82%, 84%, 86%, 88%, 90%, 92%, or 95% the Pdx1-positive, NKX6.1-positive pancreatic progenitor cells. In some embodiments, the cell cluster comprises at least about 65% the Pdx1-positive, NKX6.1-positive pancreatic progenitor cells.

In some embodiments, the cell cluster comprising at least about 50% Pdx1-positive, NKX6.1-positive pancreatic progenitor cells, at most about 30% chromogranin A (CHGA)-positive cells, and at most about 30% CDX2-positive cells can have particular functional features as compared to a comparable cell cluster having more than about 30% chromogranin A (CHGA)-positive cells or more than about 30% CDX2-positive cells. For instance, in some cases, further differentiation of the cell cluster comprising at least about 50% Pdx1-positive, NKX6.1-positive pancreatic progenitor cells, at most about 30% chromogranin A (CHGA)-positive cells, and at most about 30% CDX2-positive cells results in a first cell cluster comprising non-native pancreatic β cells that has a higher glucose-stimulated insulin secretion (GSIS) stimulation index than a second cell cluster comprising the non-native pancreatic β cells differentiated from a comparable cell cluster comprising at least about 50% the Pdx1-positive, NKX6.1-positive pancreatic progenitor cells, and more than 30% the chromogranin A (CHGA)-positive cells or more than 30% the CDX2-positive cells as measured by flow cytometry.

In some aspects, the present disclosure provides a cell cluster comprising at least about 60%, 62%, 64%, 65%, 68%, 70%, 72%, 74%, 76%, 78%, 80%, 82%, 84%, 86%, 88%, or 90% Pdx1-positive, NKX6.1-negative pancreatic progenitor cells and at most about 40%, 38%, 36%, 34%, 32%, 30%, 28%, 26%, 25%, 24%, 22%, 20%, 18%, 16%, 15%, 14%, 12%, or 10% CDX2-positive cells. In some embodiments, the cell cluster comprises at least about 85% the Pdx1-positive, NKX6.1-negative pancreatic progenitor cells. In some embodiments, the cell cluster comprises at most about 15% the CDX2-positive cells. In some cases, the cell cluster comprises at least about 85% the Pdx1-positive, NKX6.1-negative pancreatic progenitor cells and at most about 15% the CDX2-positive cells.

In some embodiments, the cell cluster comprising at least about 60% Pdx1-positive, NKX6.1-negative pancreatic progenitor cells and at most about 40% CDX2-positive cells can have particular functional features as compared to a comparable cell cluster having more than about 40% CDX2-positive cells. For instance, in some cases, further differentiation of the cell cluster comprising at least about 60% Pdx1-positive, NKX6.1-negative pancreatic progenitor cells and at most about 40% CDX2-positive cells results in a first cell cluster comprising non-native pancreatic β cells that has a higher glucose-stimulated insulin secretion (GSIS) stimulation index than a second cell cluster comprising the non-native pancreatic β cells differentiated from a comparable cell cluster comprising at least about 60% Pdx1-positive, NKX6.1-negative pancreatic progenitor cells and more than 40% the CDX2-positive cells as measured by flow cytometry.

In some aspects, the present disclosure provides a cell cluster comprising non-native pancreatic β cells. In some embodiments, the cell cluster disclosed herein is obtained from differentiation of primitive gut tube cells by contacting the primitive gut tube cells with a bone morphogenetic protein (BMP) signaling pathway inhibitor and a growth factor from transformation growth factor β (TGF-β) superfamily. In some embodiments, the cell cluster has a higher number of the non-native pancreatic β cells per cubic micrometer as compared to a comparable second cell cluster obtained from differentiation of primitive gut tube cells without the contacting. In some embodiments, cell cluster has an at least about 1.1, 1.2, 1.3, 1.4, 1.5, or 1.6 fold higher number of the non-native pancreatic β cells per cubic micrometer as compared to the comparable second cell cluster.

In some cases, the cell cluster comprising non-native pancreatic β cells disclosed herein exhibits higher insulin secretion in response to glucose challenge as compared to a comparable cell cluster obtained from differentiation of primitive gut tube cells without contacting with BMP signaling pathway inhibitor or growth factor from TGF-β family. In some embodiments, the cell cluster exhibits at least about 1.2, 1.5, 2, 2.5, 3, 3.5, 4, 4.5, or 5 fold higher an insulin secretion as compared to the comparable second cell cluster. In some embodiments, the cell cluster exhibits a higher GSIS stimulation index as compared to the comparable second cell cluster. In some embodiments, the GSIS stimulation index of the cell cluster is at least about 1.2 fold, at least about 1.5 fold, at least about 1.8 fold, at least about 2 fold, at least about 2.2 fold, at least about 2.4 fold, at least about 2.8 fold, or at least about 3 fold higher than that of the second cell cluster. In some embodiments, GSIS stimulation index of the cell cluster is at least about 3 fold higher than that of the second population. In some embodiments, GSIS stimulation index is calculated as a ratio of insulin secretion in response to 20 mM glucose challenge to insulin secretion in response to 2 mM glucose challenge. In some embodiments, the non-native pancreatic β cells exhibit an in vitro glucose-stimulated insulin secretion response when exposed to a glucose challenge. In some cases, non-native pancreatic β cells exhibit an insulin secretion in response to a first concentration of $K^+$. In some embodiments, the cell cluster exhibits a higher insulin secretion as compared to the comparable second cell cluster in response to a first concentration of $K^+$. In some embodiments, cell cluster exhibits at least about 1.2 fold, at least about 1.5 fold, at least about 1.8 fold, at least about 2 fold, at least about 2.2 fold, at least about 2.4 fold, at least about 2.8 fold, at least about 3 fold, at least about 3.2 fold, at least about 3.4 fold, at least about 3.6 fold, at least about 3.8 fold, at least about 4 fold higher an insulin secretion as compared to the comparable second cell cluster in response to a first concentration of $K^+$.

In some cases, cell populations or cell clusters disclosed herein are unsorted, e.g., isolated cell populations or cell clusters that have not been through cell sorting process. In some embodiments, the cell cluster disclosed herein can refer to a cell cluster formed by self-aggregation of cells cultured in a given environment, for instance, in a 3D suspension culture. In some embodiments, cell clusters disclosed herein are intermediate cell clusters formed during the differentiation process as described herein. In some cases, the intermediate cell clusters, e.g., cell clusters comprising Pdx1-positive, NKX6.1-negative pancreatic progenitor cells (e.g., Stage β cell clusters) or cell clusters comprising Pdx1-positive, NKX6.1-positive pancreatic progenitor cells (e.g., Stage 4 cell clusters), are not subjected to cell sorting. In some case, cell populations going through cell sorting may not be able to form the intermediate cell clusters disclosed herein. For instance, Pdx1-positive pancreatic progenitor cells, after going through cell sorting, may not be able to form a cell cluster as disclosed herein.

Cell sorting as described herein can refer to a process of isolating a group of cells from a plurality of cells by relying on differences in cell size, shape (morphology), surface protein expression, endogenous signal protein expression, or any combination thereof. In some cases, cell sorting comprises subjecting the cells to flow cytometry. Flow cytometry can be a laser- or impedance-based, biophysical technology. During flow cytometry, one can suspend cells in a stream of fluid and pass them through an electronic detection apparatus. In one type of flow cytometry, fluorescent-activated cell sorting (FACS), based on one or more parameters of the cells' optical properties (e.g., emission wave length upon laser excitation), one can physically separate and thereby purify cells of interest using flow cytometry. As described herein, an unsorted cell cluster can be cell cluster that formed by a plurality of cells that have not been subject to an active cell sorting process, e.g., flow cytometry. In some cases, flow cytometry as discussed herein can be based on one or more signal peptides expressed in the cells. For example, a cell cluster can comprise cells that express a signal peptide (e.g., a fluorescent protein, e.g., green fluorescent protein (GFP) or tdTomato). In some cases, the signal peptide is expressed as an indicator of insulin expression in the cells. For instance, a cell cluster can comprise cell harboring an exogenous nucleic acid sequence coding for GFP under the control of an insulin promoter. The insulin promoter can be an endogenous or exogenous promoter. In some cases, the expression of GFP in these cells can be indicative of insulin expression in the cells. The GFP signal can thus be a marker of a pancreatic β cell. In some cases, cell sorting as described herein can comprise magnetic-activated flow cytometry, where magnetic antibody or other ligand is used to label cells of different types, and the differences in magnetic properties can be used for cell sorting.

The percentage of cells expressing one or more particular markers, like Pdx1, NKX6.1, insulin, NGN3, or CHGA, described herein can be the percentage value detected using techniques like flow cytometry assay. In some cases, during a flow cytometry assay, cell population or cell cluster discussed herein are dispersed into single-cell suspension by incubation in digesting enzyme like trypsin or TrypLE™ Express. Dispersed cell can be washed in suitable buffer like PBS, centrifuged and then re-suspended in fixation buffer like 4% PFA. Incubation with primary antibodies against the cell markers of interest can then be conducted, which can be followed by incubation with the secondary antibodies. After antibody incubation, the cells can be washed and the subject to segregation by flow cytometry. Techniques other than flow cytometry can also be used to characterize the cells described herein, e.g., determine the cell percentages. Non-limiting examples of cell characterization methods include gene sequencing, microscopic techniques (fluorescence microscopy, atomic force microscopy), karyotyping, isoenzyme analysis, DNA properties, viral susceptibility.

In some aspects, the disclosure relates to a composition comprising a population of glucose-responsive insulin secreting cells, wherein the cells secrete a higher amount of insulin upon induction with KCl (e.g., about 20 to about 50 mM, e.g., about 30 mM) as compared to the amount of insulin secreted upon induction with glucose. In some embodiments, the population of glucose-responsive insulin secreting cells secrete at least 1.5 times, 2 times, 2.5 times, 3 times higher amount of insulin upon induction with KCl as compared to the amount of insulin secreted upon induction with glucose.

In some aspects, the disclosure relates to a composition comprising a population of glucose-responsive insulin secreting cells, wherein the cells secrete a higher amount of insulin upon induction with KCl and/or glucose, in the presence of a signaling factor as compared to comparable cells in the absence of the signaling factor. In some embodiments, the cells secrete higher amount of insulin in the presence of high glucose, but not in the presence of low glucose. In some embodiments, the high glucose concentration is about 10-20 mM. In some embodiments, the low glucose concentration is about 2-5 mM.

In some aspects, the disclosure relates to a composition comprising a population of differentiated pancreatic progenitor cells, wherein the population comprises at least 60% pancreatic β cells as determined by flow cytometry. In some embodiments, the population comprises at least 65%, 70%, 75%, 80%, 85%, or 90% pancreatic β cells. In some embodiments, the population comprises a higher percentage of pancreatic β cells upon being contacted with a predetermined basal medium component as compared to a comparable population not contacted with the basal medium component.

The in vitro-matured, SC-β cell (e.g., pancreatic β cells) generated according to the disclosed methods described herein demonstrate many advantages, for example, they perform glucose stimulated insulin secretion in vitro, resemble human islet β cells by gene expression and ultrastructure, secrete human insulin and ameliorate hyperglycemia when transplanted into mice, provide a new platform for cell therapy (e.g., transplantation into a subject in need of additional and/or functional β cells), drug screening (e.g., for insulin production/secretion, survival, dedifferentiation, etc.), research (e.g., determining the differences in function between normal and diabetic β cell), and tissue engineering (e.g., using the SC-β cells as the first cell type in reconstructing an islet).

III. Stem Cells and Reprogramming

Provided herein is use of stem cells for producing SC-β cells (e.g., mature pancreatic β cells or β-like cells) or precursors thereof. In an embodiment, germ cells may be used in place of, or with, the stem cells to provide at least one SC-β cell, using similar protocols as described in U.S. Patent Application Publication No. US20150240212 and US20150218522, each of which is herein incorporated by reference in its entirety. Suitable germ cells can be prepared, for example, from primordial germ cells present in human fetal material taken about 8-11 weeks after the last menstrual period. Illustrative germ cell preparation methods are described, for example, in Shamblott et al., Proc. Natl. Acad. Sci. USA 95:13726, 1998 and U.S. Pat. No. 6,090,622.

Provided herein are compositions and methods of generating SC-β cells (e.g., pancreatic β cells). Generally, the at least one SC-β cell or precursor thereof, e.g., pancreatic progenitors produced according to the methods disclosed herein can comprise a mixture or combination of different cells, e.g., for example a mixture of cells such as primitive gut tube cells, Pdx1-positive pancreatic progenitors, Pdx1-positive, NKX6-1-positive pancreatic progenitors, Ngn3-positive endocrine progenitor cells, insulin-positive endocrine cell (e.g., (β-like cells), and/or other pluripotent or stem cells.

The at least one SC-β cell or precursor thereof can be produced according to any suitable culturing protocol to differentiate a stem cell or pluripotent cell to a desired stage of differentiation. In some embodiments, the at least one SC-β cell or the precursor thereof are produced by culturing at least one pluripotent cell for a period of time and under conditions suitable for the at least one pluripotent cell to differentiate into the at least one SC-β cell or the precursor thereof.

In some embodiments, the at least one SC-β cell or precursor thereof is a substantially pure population of SC-β cells or precursors thereof. In some embodiments, a population of SC-β cells or precursors thereof comprises a mixture of pluripotent cells or differentiated cells. In some embodiments, a population SC-β cells or precursors thereof are substantially free or devoid of embryonic stem cells or pluripotent cells or iPS cells.

In some embodiments, a somatic cell, e.g., fibroblast can be isolated from a subject, for example as a tissue biopsy, such as, for example, a skin biopsy, and reprogrammed into an induced pluripotent stem cell for further differentiation to produce the at least one SC-β cell or precursor thereof for use in the compositions and methods described herein. In some embodiments, a somatic cell, e.g., fibroblast is maintained in culture by methods known by one of ordinary skill in the art, and in some embodiments, propagated prior to being converted into SC-β cells by the methods as disclosed herein.

In some embodiments, the at least one SC-β cell or precursor thereof are maintained in culture by methods known by one of ordinary skills in the art, and in some embodiments, propagated prior to being converted into SC-β cells by the methods as disclosed herein.

Further, at least one SC-β cell or precursor thereof, e.g., pancreatic progenitor can be from any mammalian species, with non-limiting examples including a murine, bovine, simian, porcine, equine, ovine, or human cell. For clarity and simplicity, the description of the methods herein refers to a mammalian at least one SC-β cell or precursor thereof but it should be understood that all of the methods described herein can be readily applied to other cell types of at least one SC-β cell or precursor thereof. In some embodiments, the at least one SC-β cell or precursor thereof is derived from a human individual.

Stem Cells

Embodiments of the present disclosure can related to use of stem cells for generation of pancreatic β cells or precursors thereof. The term "stem cell" as used herein can refer to a cell (e.g., plant stem cell, vertebrate stem cell) that has the ability both to self-renew and to generate a differentiated cell type (Morrison et al., (1997) Cell 88:287-298). In the context of cell ontogeny, the adjective "differentiated", or "differentiating" is a relative term. A "differentiated cell" can be a cell that has progressed further down the developmental pathway than the cell it is being compared with. Thus, pluripotent stem cells can differentiate into lineage-restricted progenitor cells (e.g., mesodermal stem cells), which in turn can differentiate into cells that are further restricted (e.g., neuron progenitors), which can differentiate into end-stage cells (e.g., terminally differentiated cells, e.g., neurons, cardiomyocytes, etc.), which play a characteristic role in a certain tissue type, and can or cannot retain the capacity to proliferate further. Stem cells can be characterized by both the presence of specific markers (e.g., proteins, RNAs, etc.) and the absence of specific markers. Stem cells can also be identified by functional assays both in vitro and in vivo, particularly assays relating to the ability of stem cells to give rise to multiple differentiated progeny. In an embodiment, the host cell is an adult stem cell, a somatic stem cell, a non-embryonic stem cell, an embryonic stem cell, hematopoietic stem cell, an include pluripotent stem cells, and a trophoblast stem cell.

Stem cells that can be used in the method provided herein can include pluripotent stem cells (PSCs). The term "pluripotent stem cell" or "PSC" as used herein can refer to a stem cell capable of producing all cell types of the organism. Therefore, a PSC can give rise to cells of all germ layers of the organism (e.g., the endoderm, mesoderm, and ectoderm of a vertebrate). Pluripotent cells can be capable of forming teratomas and of contributing to ectoderm, mesoderm, or endoderm tissues in a living organism. Pluripotent stem cells of plants can be capable of giving rise to all cell types of the plant (e.g., cells of the root, stem, leaves, etc.).

Embodiments of the present disclosure can related to use of PSCs for generation of pancreatic β cells or precursors thereof. PSCs of animals can be derived in a number of different ways. For example, embryonic stem cells (ESCs) can be derived from the inner cell mass of an embryo (Thomson et. al, Science. 1998 Nov. 6; 282(5391):1145-7) whereas induced pluripotent stem cells (iPSCs) can be derived from somatic cells (Takahashi et. al, Cell. 2007 Nov. 30; 131(5):861-72; Takahashi et. al, Nat Protoc. 2007; 2(12):3081-9; Yu et. al, Science. 2007 Dec. 21; 318(5858): 1917-20. Epub 2007 Nov. 20). Because the term PSC can refer to pluripotent stem cells regardless of their derivation, the term PSC can encompass the terms ESC and iPSC, as well as the term embryonic germ stem cells (EGSC), which are another example of a PSC. PSCs can be in the form of an established cell line, they can be obtained directly from primary embryonic tissue, or they can be derived from a somatic cell.

Embodiments of the present disclosure can related to use of ESCs for generation of pancreatic β cells or precursors thereof. By "embryonic stem cell" (ESC) can be meant a PSC that is isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells can be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs can grow as flat colonies with large nucleo-cytoplasmic ratios, defined borders and prominent nucleoli. In addition, ESCs can express SSEA-3, SSEA-4, TRA-1-60, TRA-1-81, and Alkaline Phosphatase, but not SSEA-1. Examples of methods of generating and characterizing ESCs can be found in, for example, U.S. Pat. Nos. 7,029,913, 5,843,780, and 6,200, 806, each of which is incorporated herein by its entirety. Methods for proliferating hESCs in the undifferentiated form are described in WO 99/20741, WO 01/51616, and WO 03/020920, each of which is incorporated herein by its entirety.

By "embryonic germ stem cell" (EGSC) or "embryonic germ cell" or "EG cell", it can be meant a PSC that is derived from germ cells and/or germ cell progenitors, e.g. primordial germ cells, e.g. those that can become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, each of which are incorporated herein by its entirety.

Embodiments of the present disclosure can related to use of iPSCs for generation of pancreatic β cells or precursors thereof. By "induced pluripotent stem cell" or "iPSC", it can be meant a PSC that is derived from a cell that is not a PSC (e.g., from a cell this is differentiated relative to a PSC). iPSCs can be derived from multiple different cell types, including terminally differentiated cells. iPSCs can have an ES cell-like morphology, growing as flat colonies with large nucleo-cytoplasmic ratios, defined borders and prominent nuclei. In addition, iPSCs can express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs can be found in, for example, U.S. Patent Publication Nos. US20090047263, US20090068742, US20090191159, US20090227032, US20090246875, and US20090304646, each of which are incorporated herein by its entirety. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

Embodiments of the present disclosure can related to use of somatic cells for generation of pancreatic β cells or precursors thereof. By "somatic cell", it can be meant any cell in an organism that, in the absence of experimental manipulation, does not ordinarily give rise to all types of cells in an organism. In other words, somatic cells can be cells that have differentiated sufficiently that they may not naturally generate cells of all three germ layers of the body, e.g. ectoderm, mesoderm and endoderm. For example, somatic cells can include both neurons and neural progenitors, the latter of which is able to naturally give rise to all or some cell types of the central nervous system but cannot give rise to cells of the mesoderm or endoderm lineages In certain examples, the stem cells can be undifferentiated (e.g. a cell not committed to a specific lineage) prior to exposure to at least one differentiation factor or composition according to the methods as disclosed herein, whereas in other examples it can be desirable to differentiate the stem cells to one or more intermediate cell types prior to exposure of the at least one differentiation factor or composition described herein. In certain examples, the stem cells can be cultured in the presence of) suitable nutrients and optionally other cells such that the stem cells can grow and optionally differentiate. For example, embryonic fibroblasts or fibroblast-like cells can be present in the culture to assist in the growth of the stem cells. The fibroblast can be present during one stage of stem cell growth but not necessarily at all stages. For example, the fibroblast can be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells can have the characteristic of being capable under appropriate conditions of producing progeny of different cell types, e.g. derivatives of all of at least one of the 3 germinal layers (endoderm, mesoderm, and ectoderm). These cell types can be provided in the form of an established cell line, or they can be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, FISF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into mature, insulin positive cells did not involve destroying a human embryo. In some embodiments, the source of human stem cells or pluripotent stem cells used for chemically-induced differentiation into mature, insulin positive cells do not involve destroying a human embryo.

In another example, the stem cells can be isolated from tissue including solid tissue. In some embodiments, the tissue is skin, fat tissue (e.g. adipose tissue), muscle tissue, heart or cardiac tissue. In other embodiments, the tissue is for example but not limited to, umbilical cord blood, placenta, bone marrow, or chondral.

Stem cells that can be used in the methods provided herein can also include embryonic cells of various types, exemplified by human embryonic stem (hES) cells, as described by Thomson et al, (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also applicable to the methods provided herein can be lineage committed stem cells, such as mesodermal stem cells and other early cardiogenic cells (see Reyes et al, (2001) Blood 98:2615-2625; Eisenberg & Bader (1996) Circ Res. 78(2):205-16; etc.) The stem cells can be obtained from any mammalian species, e.g. human, equine, bovine, porcine, canine, feline, rodent, e.g. mice, rats, hamster, primate, etc. In some embodiments, a human embryo was not destroyed for the source of pluripotent cell used on the methods and compositions as disclosed herein. In some embodiments, a human embryo is not destroyed for the source of pluripotent cell used on the methods and compositions as disclosed herein.

A mixture of cells from a suitable source of endothelial, muscle, and/or neural stem cells can be harvested from a mammalian donor for the purpose of the present disclosure. A suitable source is the hematopoietic microenvironment. For example, circulating peripheral blood, preferably mobilized (e.g., recruited), may be removed from a subject. In an embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

In some embodiments, the pancreatic β cell as described herein can be derived from one or more of trichocytes, keratinocytes, gonadotropes, corticotropes, thyrotropes, somatotropes, lactotrophs, chromaffin cells, parafollicular cells, glomus cells melanocytes, nevus cells, Merkel cells, odontoblasts, cementoblasts corneal keratocytes, retina Muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells (e.g., PP cells), pancreatic F cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, splenocytes (e.g., T lymphocytes, B lymphocytes, dendritic cells, microphages, leukocytes), trophoblast stem cells, or any combination thereof.

Reprogramming

The term "reprogramming" as used herein can refer to the process that alters or reverses the differentiation state of a somatic cell. The cell can either be partially or terminally differentiated prior to the reprogramming. Reprogramming can encompass complete reversion of the differentiation state of a somatic cell to a pluripotent cell. Such complete reversal of differentiation can produce an induced pluripotent (iPS) cell. Reprogramming as used herein can also encompass partial reversion of a cells differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming can involve alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

As used herein, the term "reprogramming factor" can refer to a molecule that is associated with cell "reprogramming," that is, differentiation, and/or de-differentiation, and/or transdifferentiation, such that a cell converts to a different cell type or phenotype. Reprogramming factors generally affect expression of genes associated with cell differentiation, de-differentiation and/or transdifferentiation. Transcription factors are examples of reprogramming factors.

The term "differentiation" and their grammatical equivalents as used herein can refer to the process by which a less specialized cell (e.g., a more naive cell with a higher cell potency) becomes a more specialized cell type (e.g., a less naive cell with a lower cell potency); and that the term "de-differentiation" can refer to the process by which a more specialized cell becomes a less specialized cell type (e.g., a more naive cell with a higher cell potency).

In some embodiments of the present disclosure, the method excludes the use of reprogramming factor(s) that are not small molecules. However, it will be appreciated that the method can utilize "routine" tissue culture components such as culture media, serum, serum substitutes, supplements, antibiotics, etc, such as RPMI, Renal Epithelial Basal Medium (REBM), Dulbecco's Modified Eagle Medium (DMEM), MCDB131 medium, CMRL 1066 medium, F12, foetal calf serum (FCS), foetal bovine serum (FBS), bovine serum albumin (BSA), D-glucose, L-glutamine, GlutaMAX®-1 (dipeptide, L-alanine-L-glutamine), B27, heparin, progesterone, putrescine, laminin, nicotinamide, insulin, transferrin, sodium selenite, selenium, ethanolamine, human epidermal growth factor (hEGF), basic fibroblast growth factor (bFGF), hydrocortisone, epinephrine, normacin, penicillin, streptomycin, gentamicin and amphotericin, etc. It is to be understood that these typical tissue culture components (and other similar tissue culture components that are routinely used in tissue culture) are not small molecule reprogramming molecules for the purposes of the present disclosure. These components are either not small molecules as defined herein and/or are not reprogramming factors as defined herein.

Accordingly, in an embodiment, the present disclosure does not involve a culturing step of the cell(s) with one or more exogenous polynucleotide or polypeptide reprogramming factor(s). Accordingly, in an embodiment, the method of the present disclosure does not involve the introduction of one or more exogenous polynucleotide or polypeptide reprogramming factor(s), e.g., by introducing transposons, viral transgenic vectors (such as retroviral vectors), plasmids, mRNA, miRNA, peptides, or fragments of any of these molecules, that are involved in producing induced β cells or, otherwise, inducing cells of the present disclosure to differentiate, de-differentiation and/or transdifferentiate.

That is, in an embodiment, the method occurs in the absence of one or more exogenous polynucleotide or polypeptide reprogramming factor(s). Accordingly, it is to be understood that in an embodiment, the method of the present disclosure utilizes small molecules (e.g., HDAC inhibitors) to reprogram cells, without the addition of polypeptide transcription factors; other polypeptide factors specifically associated with inducing differentiation, de-differentiation, and/or transdifferentiation; polynucleotide sequences encoding polypeptide transcription factors, polynucleotide sequences encoding other polypeptide factors specifically associated with inducing differentiation, de-differentiation, and/or transdifferentiation; mRNA; interference RNA; microRNA and fragments thereof.

IV Method of Generating Pancreatic β Cells

In some cases, the pancreatic β cells (e.g., non-native pancreatic β cells or SC-β cells) or the cell clusters comprising pancreatic β cells as described herein are generated from any starting cell population in vitro. For example, the starting cell can include, without limitation, insulin-positive endocrine cells (e.g., Ngn3-positive endocrine cells) or any precursor thereof, such as a Nkx6.1-positive pancreatic progenitor cell, a Pdx1-positive pancreatic progenitor cell, a primitive gut tub cell, a definitive endoderm cell, a pluripotent stem cell, an embryonic stem cell, and an induced pluripotent stem cell. In some cases, the method includes differentiation of a reprogrammed cell, a partially reprogrammed cell (e.g., a somatic cell, e.g., a fibroblast which has been partially reprogrammed such that it exists in an intermediate state between an induced pluripotency cell and the somatic cell from which it has been derived), a transdifferentiated cell. In some cases, the pancreatic β cell or the cell cluster comprising the pancreatic β cell disclosed herein can be differentiated in vitro from an insulin-positive endocrine cell or a precursor thereof. In some cases, the pancreatic β cell or the cell cluster comprising the pancreatic β cell is differentiated in vitro from a NKX6.1-positive pancreatic progenitor cell. In some cases, the pancreatic β cell or the cell cluster comprising the pancreatic β cell is differentiated in vitro from a Pdx1-positive pancreatic progenitor cell. In some cases, the pancreatic β cell or the cell cluster comprising the pancreatic β cell is differentiated in vitro from a primitive gut tube cell. In some cases, the pancreatic β cell or the cell cluster comprising the pancreatic β cell is differentiated in vitro from a definitive endoderm cell. In some cases, the pancreatic β cell or the cell cluster comprising the pancreatic β cell is differentiated in vitro from a pluripotent stem cell. In some cases, the pluripotent stem cell is selected from the group consisting of an embryonic stem cell and induced pluripotent stem cell. As discussed above, the non-native pancreatic β cells can also be referred to as stem cell-derived β cells (SC-β cells) as they can be derived from stem cells in vitro. In some cases, the SC-β cell or the pluripotent stem cell from which the SC-β cell is derived is human. In some cases, the SC-β cell is human.

One aspect of the present disclosure relates to a method of propagating stem cells, e.g., ES cells or pluripotent stem cells, e.g., iPS cells. In some cases, the stem cells can be cultured and propagated in a suitable culture medium, such as, RPMI, Renal Epithelial Basal Medium (REBM), Dulbecco's Modified Eagle Medium (DMEM), MCDB131 medium, or CMRL 1066 medium.

Some aspects of the present disclosure provide a method of generating pancreatic β cells, e.g., non-native pancreatic β cells, or cell cluster comprising pancreatic β cells. In some cases, the method can be any currently available protocol, such as those described in U.S. patent application Ser. Nos. 14/684,129 and 14/684,101, each of which is incorporated herein by its entirety.

Aspects of the disclosure involve definitive endoderm cells. Definitive endoderm cells of use herein can be derived from any source or generated in accordance with any suitable protocol. In some aspects, pluripotent stem cells, e.g., iPSCs or hESCs, are differentiated to endoderm cells. In some aspects, the endoderm cells (stage 1) are further differentiated, e.g., to primitive gut tube cells (stage 2), Pdx1-positive pancreatic progenitor cells (stage 3), NKX6.1-positive pancreatic progenitor cells (stage 4), or Ngn3-positive endocrine progenitor cells or insulin-positive endocrine cells (stage 5), followed by induction or maturation to SC-β cells (stage 6).

In some cases, definitive endoderm cells can be obtained by differentiating at least some pluripotent cells in a population into definitive endoderm cells, e.g., by contacting a population of pluripotent cells with i) at least one growth factor from the TGF-β superfamily, and ii) a WNT signaling pathway activator, to induce the differentiation of at least some of the pluripotent cells into definitive endoderm cells, wherein the definitive endoderm cells express at least one marker characteristic of definitive endoderm.

Any growth factor from the TGF-β superfamily capable of inducing the pluripotent stem cells to differentiate into definitive endoderm cells (e.g., alone, or in combination with a WNT signaling pathway activator) can be used in the method provided herein. In some cases, the growth factor from the TGF-β superfamily comprises Activin A. In some cases, the growth factor from the TGF-β superfamily comprises growth differentiating factor 8 (GDF8). Any WNT signaling pathway activator capable of inducing the pluripotent stem cells to differentiate into definitive endoderm cells (e.g., alone, or in combination with a growth factor from the TGF-β superfamily) can be used in the method provided herein. In some cases, the WNT signaling pathway activator comprises CHIR99Q21. In some cases, the WNT signaling pathway activator comprises Wnt3a recombinant protein.

In some cases, differentiating at least some pluripotent cells in a population into definitive endoderm cells is achieved by a process of contacting a population of pluripotent cells with i) Activin A, and ii) CHIR99021 for a suitable period of time, e.g., about 2 days, about 3 days, about 4 days, or about 5 days to induce the differentiation of at least some of the pluripotent cells in the population into definitive endoderm cells, wherein the definitive endoderm cells express at least one marker characteristic of definitive endoderm.

In some examples, the method comprises differentiating pluripotent cells into definitive endoderm cells by contacting a population of pluripotent cells with a suitable concentration of the growth factor from the TGF-β superfamily (e.g., Activin A), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some cases, the method comprises use of about 100 ng/mL Activin A for differentiation of pluripotent cells into definitive endoderm cells. In some cases, the method comprises use of about 200 ng/mL Activin A for differentiation of pluripotent cells into definitive endoderm cells.

In some examples, the method comprises differentiating pluripotent cells into definitive endoderm cells by contacting a population of pluripotent cells with a suitable concentration of the WNT signaling pathway activator (e.g., CHIR99021), such as, about 0.01 µM, about 0.05 µM, about 0.1 µM, about 0.2 µM, about 0.5 µM, about 0.8 µM, about 1 µM, about 1.5 µM, about 2 µM, about 2.5 µM, about 3 µM, about 3.5 µM, about 4 µM, about 5 µM, about 8 µM, about 10 µM, about 12 µM, about 15 µM, about 20 µM, about 30 βM, about 50 µM, about 100 µM, or about 200 µM. In some cases, the method comprises use of about 2 µM CHIR99021 for differentiation of pluripotent cells into definitive endoderm cells. In some cases, the method comprises use of about 5 µM CHIR99021 for differentiation of pluripotent cells into definitive endoderm cells.

In some cases, a definitive endoderm cell produced by the methods as disclosed herein expresses at least one marker selected from the group consisting of: Nodal, Tmprss2, Tmem30b, St14, Spink3, Sh3g12, Ripk4, Rab1S, Npnt, Clic6, Cldn5, Cacna1b, Bnip1, Anxa4, Emb, FoxA1, Sox17, and Rbm35a, wherein the expression of at least one marker is upregulated to by a statistically significant amount in the definitive endoderm cell relative to the pluripotent stem cell from which it was derived. In some cases, a definitive endoderm cell produced by the methods as disclosed herein does not express by a statistically significant amount at least one marker selected the group consisting of: Gata4, SPARC, AFP and Dab2 relative to the pluripotent stem cell from which it was derived. In some cases, a definitive endoderm cell produced by the methods as disclosed herein does not express by a statistically significant amount at least one marker selected the group consisting of: Zic1, Pax6, Flk1 and CD31 relative to the pluripotent stem cell from which it was derived. In some cases, a definitive endoderm cell produced by the methods as disclosed herein has a higher level of phosphorylation of Smad2 by a statistically significant amount relative to the pluripotent stem cell from which it was derived. In some cases, a definitive endoderm cell produced by the methods as disclosed herein has the capacity to form gut tube in vivo. In some cases, a definitive endoderm cell produced by the methods as disclosed herein can differentiate into a cell with morphology characteristic of a gut cell, and wherein a cell with morphology characteristic of a gut cell expresses FoxA2 and/or Claudin6, In some cases, a definitive endoderm cell produced by the methods as disclosed herein can be further differentiated into a cell of endoderm origin.

In some cases, a population of pluripotent stem cells are cultured in the presence of at least one β cell differentiation factor prior to any differentiation or during the first stage of differentiation. One can use any pluripotent stem cell, such as a human pluripotent stem cell, or a human iPS cell or any of pluripotent stem cell as discussed herein or other suitable pluripotent stem cells. In some cases, a β cell differentiation factor as described herein can be present in the culture medium of a population of pluripotent stem cells or may be added in bolus or periodically during growth (e.g. replication or propagation) of the population of pluripotent stem cells. In certain examples, a population of pluripotent stem cells can be exposed to at least one R cell differentiation factor prior to any differentiation. In other examples, a population of pluripotent stem cells may be exposed to at least one β cell differentiation factor during the first stage of differentiation.

Aspects of the disclosure involve primitive gut tube cells. Primitive gut tube cells of use herein can be derived from any source or generated in accordance with any suitable protocol. In some aspects, definitive endoderm cells are differentiated to primitive gut tube cells. In some aspects, the primitive gut tube cells are further differentiated, e.g., to Pdx1-positive pancreatic progenitor cells, NKX6.1-positive pancreatic progenitor cells, Ngn3-positive endocrine progenitor cells, insulin-positive endocrine cells, followed by induction or maturation to SC-β cells.

In some cases, primitive gut tube cells can be obtained by differentiating at least some definitive endoderm cells in a population into primitive gut tube cells, e.g., by contacting definitive endoderm cells with at least one growth factor from the fibroblast growth factor (FGF) family, to induce the differentiation of at least some of the definitive endoderm cells into primitive gut tube cells, wherein the primitive gut tube cells express at least one marker characteristic of primitive gut tube cells.

Any growth factor from the FGF family capable of inducing definitive endoderm cells to differentiate into primitive gut tube cells (e.g., alone, or in combination with other factors) can be used in the method provided herein. In some cases, the at least one growth factor from the FGF family comprises keratinocyte growth factor (KGF). In some cases, the at least one growth factor from the FGF family comprises FGF2. In some cases, the at least one growth factor from the FGF family comprises FGF8B. In some cases, the at least one growth factor from the FGF family comprises FGF 10. In some cases, the at least one growth factor from the FGF family comprises FGF21.

In some cases, primitive gut tube cells can be obtained by differentiating at least some definitive endoderm cells in a population into primitive gut tube cells, e.g., by contacting definitive endoderm cells with KGF for a certain period of time, e.g., about 1 day, about 2 days, about 3 days, or about 4 days, to induce the differentiation of at least some of the definitive endoderm cells into primitive gut tube cells.

In some cases, the method comprises differentiating definitive endoderm cells into primitive gut tube cells by contacting definitive endoderm cells with a suitable concentration of the growth factor from the FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some cases, the method comprises use of about 50 ng/mL KGF for differentiation of definitive endoderm cells into primitive gut tube cells. In some cases, the method comprises use of about 100 ng/mL KGF for differentiation of definitive endoderm cells into primitive gut tube cells.

Aspects of the disclosure involve Pdx1-positive pancreatic progenitor cells. Pdx1-positive pancreatic progenitor cells of use herein can be derived from any source or generated in accordance with any suitable protocol. In some aspects, primitive gut tube cells are differentiated to Pdx1-positive pancreatic progenitor cells. In some aspects, the Pdx1-positive pancreatic progenitor cells are further differentiated, e.g., NKX6.1-positive pancreatic progenitor cells, Ngn3-positive endocrine progenitor cells, insulin-positive endocrine cells, followed by induction or maturation to SC-β cells, In some aspects, Pdx1-positive pancreatic progenitor cells can be obtained by differentiating at least some primitive gut tube cells in a population into Pdx1-positive pancreatic progenitor cells, e.g., by contacting primitive gut tube cells with i) at least one BMP signaling pathway inhibitor, ii) a growth factor from TGF-β superfamily, iii) at least one growth factor from the FGF family, iv) at least one SHH pathway inhibitor, v) at least one retinoic acid (RA) signaling pathway activator; vi) at least one protein kinase C activator, and vii) ROCK inhibitor to induce the differentiation of at least some of the primitive gut tube cells into Pdx1-positive pancreatic progenitor cells, wherein the Pdx1-positive pancreatic progenitor cells express Pdx1.

In some aspects, Pdx1-positive pancreatic progenitor cells can be obtained by differentiating at least some primitive gut tube cells in a population into Pdx1-positive pancreatic progenitor cells, e.g., by contacting primitive gut tube cells with i) at least one BMP signaling pathway inhibitor, ii) a growth factor from TGF-β superfamily, iii) at least one growth factor from the FGF family, iv) at least one SHH pathway inhibitor, v) at least one retinoic acid (RA) signaling pathway activator; and vi) at least one protein kinase C activator, to induce the differentiation of at least some of the primitive gut tube cells into Pdx1-positive pancreatic progenitor cells, wherein the Pdx1-positive pancreatic progenitor cells express Pdx1.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with i) at least one BMP signaling pathway inhibitor, ii) at least one growth factor from the FGF family, iii) at least one SHH pathway inhibitor, iv) at least one retinoic acid (RA) signaling pathway activator; and v) at least one protein kinase C activator, to induce the differentiation of at least some of the primitive gut tube cells into Pdx1-positive pancreatic progenitor cells, wherein the Pdx1-positive pancreatic progenitor cells express Pdx1.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with i) at least one SHH pathway inhibitor, ii) at least one retinoic acid (RA) signaling pathway activator; and iii) at least one protein kinase C activator, wherein the Pdx1-positive pancreatic progenitor cells express Pdx1.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with i) at least one growth factor from the FGF family, and ii) at least one retinoic acid (RA) signaling pathway activator, to induce the differentiation of at least some of the primitive gut tube cells into Pdx1-positive pancreatic progenitor cells, wherein the Pdx1-positive pancreatic progenitor cells express Pdx1.

Any BMP signaling pathway inhibitor capable of inducing primitive gut tube cells to differentiate into Pdx1-positive pancreatic progenitor cells (e.g., alone, or with any combination of a growth factor from TGF-β superfamily, at least one growth factor from the FGF family, at least one SHH pathway inhibitor, at least one retinoic acid signaling pathway activator, at least one protein kinase C activator, and ROCK inhibitor) can be used in the method provided herein. In some cases, the BMP signaling pathway inhibitor comprises LDN193189 or DMH-1. In some examples, the method comprises contacting primitive gut tube cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 µM. In some examples, the method comprises contacting primitive gut tube cells with a concentration of BMP signaling pathway inhibitor (e.g., DMH-1), such as, about 0.01 µM, about 0.02 µM, about 0.05 µM, about 0.1 µM, about 0.2 µM, about 0.5 µM, about 0.8 µM, about 1 µM, about 1.2 µM, about 1.5 µM, about 1.75 µM, about 2 µM, about 2.2 µM, about 2.5 µM, about 2.75 µM, about 3 µM, about 3.25 µM, about 3.5 µM, about 3.75 µM, about 4 µM, about 4.5 µM, about 5 µM, about 8 µM, about 10 µM, about 15 µM, about 20 µM, about 30 µM, about 40 µM, about 50 µM, or about 100 µM.

Any growth factor from the TGF-β superfamily capable of inducing primitive gut tube cells to differentiate into Pdx1-positive pancreatic progenitor cells (e.g., alone, or with any combination of at least one BMP signaling pathway inhibitor, a growth factor from the FGF family, at least one SHH pathway inhibitor, at least one retinoic acid signaling pathway activator, at least one protein kinase C activator, and ROCK inhibitor) can be used. In some cases, the growth factor from TGF-β family comprises Activin A. In some cases, the growth factor from TGF-β family comprises Activin A or GDF8. In some examples, the method comprises contacting primitive gut tube cells with a concentration of a growth factor from TGF-β superfamily (e.g., Activin A), such as, about 5 ng/mL, about 7.5 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 21 ng/mL, about 22 ng/mL, about 23 ng/mL, about 24 ng/mL, about 25 ng/mL, about 26 ng/mL, about 27 ng/mL, about 28 ng/mL, about 29 ng/mL, about 30 ng/mL, about 35 ng/mL, about 40 ng/mL, about 50 ng/mL, or about 100 ng/mL.

Any growth factor from the FGF family capable of inducing primitive gut tube cells to differentiate into Pdx1-positive pancreatic progenitor cells (e.g., alone, or with any combination of at least one BMP signaling pathway inhibitor, a growth factor from TGF-β superfamily, at least one SHH pathway inhibitor, at least one retinoic acid signaling pathway activator, at least one protein kinase C activator, and ROCK inhibitor) can be used. In some cases, the at least one growth factor from the FGF family comprises keratinocyte growth factor (KGF). In some cases, the at least one growth factor from the FGF family is selected from the group consisting of FGF2, FGF8B, FGF 10, and FGF21. In some examples, the method comprises contacting primitive gut tube cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL.

Any SHH pathway inhibitor capable of inducing primitive gut tube cells to differentiate into Pdx1-positive pancreatic progenitor cells (e.g., alone, or with any combination of at least one BMP signaling pathway inhibitor, at least one growth factor from the FGF family, a growth factor from TGF-β superfamily, at least one retinoic acid signaling pathway activator, at least one protein kinase C activator, and ROCK inhibitor) can be used. In some cases, the SHH pathway inhibitor comprises Sant1. In some examples, the method comprises contacting primitive gut tube cells with a concentration of a SHH pathway inhibitor (e.g., Sant1), such as, about 0.001 µM, about 0.002 µM, about 0.005 µM, about 0.01 µM, about 0.02 µM, about 0.03 µM, about 0.05 µM, about 0.08 µM, about 0.1 µM, about 0.12 βM, about 0.13 βM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 βM, about 0.25 βM, about 0.26 µM, about 0.27 µM, about 0.28 µM, about 0.29 µM, about 0.3 βM, about 0.31 βM, about 0.32 µM, about 0.33 µM, about 0.34 µM, about 0.35 µM, about 0.4 βM, about 0.45 βM, about 0.5 µM, about 0.6 µM, about 0.8 µM, about 1 µM, about 2 µM, or about 5 βM.

Any RA signaling pathway activator capable of inducing primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, at least one protein kinase C activator, and ROCK inhibitor) can be used. In some cases, the RA signaling pathway activator comprises retinoic acid. In some examples, the method comprises contacting primitive gut tube cells with a concentration of an RA signaling pathway activator (e.g., retinoic acid), such as, about 0.02 µM, about 0.1 µM, about 0.2 µM, about 0.25 µM, about 0.3 µM, about 0.4 µM, about 0.45 βM, about 0.5 µM, about 0.55 µM, about 0.6 µM, about 0.65 µM, about 0.7 µM, about 0.75 βM, about 0.8 µM, about 0.85 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM.

Any PKC activator capable of inducing primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, at least one RA signaling pathway activator, and ROCK inhibitor) can be used. In some cases, the PKC activator comprises PdBU. In some cases, the PKC activator comprises TPB. In some examples, the method comprises contacting primitive gut tube cells with a concentration of a PKC activator (e.g., PdBU), such as, about 10 βM, about 20 µM, about 50 µM, about 75 µM, about 80 µM, about 100 µM, about 120 µM, about 140 βM, about 150 µM, about 175 µM, about 180 µM, about 200 µM, about 210 µM, about 220 βM, about 240 µM, about 250 µM, about 260 µM, about 280 µM, about 300 µM, about 320 βM, about 340 µM, about 360 µM, about 380 µM, about 400 µM, about 420 µM, about 440 βM, about 460 µM, about 480 µM, about 500 µM, about 520 µM, about 540 µM, about 560 βM, about 580 µM, about 600 µM, about 620 µM, about 640 µM, about 660 µM, about 680 βM, about 700 µM, about 750 µM, about 800 µM, about 850 µM, about 900 µM, about 1 mM, about 2 mM, about 3 mM, about 4 mM, or about 5 mM.

Any ROCK inhibitor capable of inducing primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, PKC activator, and at least one RA signaling pathway activator) can be used. In some cases, the ROCK inhibitor comprises Y-27632, Fasudil/HA1077, or H-1152. In some cases, the ROCK inhibitor comprises Y-27632. In some examples, the method comprises contacting primitive gut tube cells with a concentration of a ROCK inhibitor (e.g., Y-27632), such as, about 0.2 µM, about 0.5 µM, about 0.75 µM, about 1 µM, about 2 βM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 µM.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with retinoic acid, KGF, Sant1, LDN193189, PdBU, Y-27632, and Activin A, for a suitable period of time, e.g., about 1 day, about 2 days, about 3 days, or about 4 days. In some cases, Pdx1-positive pancreatic progenitor cells can be obtained by differentiating at least some primitive gut tube cells in a population into Pdx1-positive pancreatic progenitor cells, e.g., by contacting primitive gut tube cells with retinoic acid, KGF, Sant1, LDN193189, PdBU, Y-27632, and Activin A, for about 2 days. In some cases, Pdx1-positive pancreatic progenitor cells can be obtained by differentiating at least some primitive gut tube cells in S3 medium.

Aspects of the disclosure involve NKX6.1-positive pancreatic progenitor cells. NKX6.1-positive pancreatic progenitor cells of use herein can be derived from any source or generated in accordance with any suitable protocol. In some aspects, Pdx1-positive pancreatic progenitor cells are differentiated to NKX6.1-positive pancreatic progenitor cells. In some aspects, the NKX6.1-positive pancreatic progenitor cells are further differentiated, e.g., to Ngn3-positive endocrine progenitor cells, or insulin-positive endocrine cells, followed by induction or maturation to SC-β cells.

In some aspects, a method of producing a NKX6.1-positive pancreatic progenitor cell from a Pdx1-positive pancreatic progenitor cell comprises contacting a population of cells (e.g., under conditions that promote cell clustering and/or promoting cell survival) comprising Pdx1-positive pancreatic progenitor cells with at least two β cell-differentiation factors comprising a) at least one growth factor from the fibroblast growth factor (FGF) family, b) a sonic hedgehog pathway inhibitor, and optionally c) a low concentration of a retinoic acid (RA) signaling pathway activator, to induce the differentiation of at least one Pdx1-positive pancreatic progenitor cell in the population into NKX6.1-positive pancreatic progenitor cells, wherein the NKX6.1-positive pancreatic progenitor cells expresses NKX6.1.

In some cases, the Pdx1-positive, NKX6.1-positive pancreatic progenitor cells are obtained by contacting Pdx1-positive pancreatic progenitor cells with i) at least one growth factor from the FGF family, ii) at least one SHH pathway inhibitor, and optionally iii) a low concentration of a RA signaling pathway activator, to induce the differentiation of at least some of the Pdx1-positive pancreatic progenitor cells into Pdx1-positive, NKX6.1-positive pancreatic progenitor cells, wherein the Pdx1-positive, NKX6.1-positive pancreatic progenitor cells expresses Pdx1 and NKX6.1.

In some cases, the Pdx1-positive, NKX6.1-positive pancreatic progenitor cells are obtained by contacting Pdx1-positive pancreatic progenitor cells with i) at least one growth factor from the FGF family, ii) at least one SHH pathway inhibitor, and optionally iii) a low concentration of a RA signaling pathway activator, iv) ROCK inhibitor, and v) at least one growth factor from the TGF-β superfamily, to induce the differentiation of at least some of the Pdx1-positive pancreatic progenitor cells into Pdx1-positive, NKX6.1-positive pancreatic progenitor cells. In some cases, the Pdx1-positive, NKX6.1-positive pancreatic progenitor cells are obtained by contacting Pdx1-positive pancreatic progenitor cells under conditions that promote cell clustering with at least one growth factor from the FGF family.

In some cases, the Pdx1-positive pancreatic progenitor cells are produced from a population of pluripotent cells. In some cases, the Pdx1-positive pancreatic progenitor cells are produced from a population of iPS cells. In some cases, the Pdx1-positive pancreatic progenitor cells are produced from a population of ESC cells. In some cases, the Pdx1-positive pancreatic progenitor cells are produced from a population of definitive endoderm cells. In some cases, the Pdx1-positive pancreatic progenitor cells are produced from a population of primitive gut tube cells.

Any growth factor from the FGF family capable of inducing Pdx1-positive pancreatic-progenitor cells to differentiate into NKX6.1-positive pancreatic progenitor cells (e.g., alone, or with any combination of at least one SHH pathway inhibitor, a ROCK inhibitor, a growth factor from the TGF-β superfamily, and at least one retinoic acid signaling pathway activator) can be used in the method provided herein. In some cases, the at least one growth factor from the FGF family comprises keratinocyte growth factor (KGF). In some cases, the at least one growth factor from the FGF family is selected from the group consisting of FGF2, FGF8B, FGF 10, and FGF21. In some examples, the method comprises contacting Pdx1-positive pancreatic progenitor cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL.

Any SHH pathway inhibitor capable of inducing Pdx1-positive pancreatic progenitor cells to differentiate into NKX6.1-positive pancreatic progenitor cells (e.g., alone, or with any combination of at least one growth factor from the FGF family, at least one retinoic acid signaling pathway activator, ROCK inhibitor, and at least one growth factor from the TGF-β superfamily) can be used in the method provided herein. In some cases, the SHH pathway inhibitor comprises Sant1. In some examples, the method comprises contacting Pdx1-positive pancreatic progenitor cells with a concentration of a SHH pathway inhibitor (e.g., Sant1), such as, about 0.001 µM, about 0.002 µM, about 0.005 µM, about 0.01 µM, about 0.02 µM, about 0.03 µM, about 0.05 µM, about 0.08 µM, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM.

Any RA signaling pathway activator capable of inducing Pdx1-positive pancreatic progenitor cells to differentiate into NKX6.1-positive pancreatic progenitor cells (e.g., alone, or with any combination of at least one growth factor from the FGF family, at least one SHH pathway inhibitor, ROCK inhibitor, and at least one growth factor from the TGF-β superfamily) can be used. In some cases, the RA signaling pathway activator comprises retinoic acid. In some examples, the method comprises contacting Pdx1-positive pancreatic progenitor cells with a concentration of an RA signaling pathway activator (e.g., retinoic acid), such as, about 0.02 µM, about 0.1 µM, about 0.2 µM, about 0.25 µM, about 0.3 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM.

Any ROCK inhibitor capable of inducing Pdx1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and at least one growth factor from the TGF-β superfamily) can be used. In some cases, the ROCK inhibitor comprises Thiazovivin, Y-27632, Fasudil/HA1077, or 14-1152. In some examples, the method comprises contacting Pdx1-positive pancreatic progenitor cells with a concentration of a ROCK inhibitor (e.g., Y-27632), such as, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 βM.

Any activator from the TGF-β superfamily capable of inducing Pdx1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and ROCK inhibitor) can be used. In some cases, the activator from the TGF-β superfamily comprises Activin A or GDF8. In some examples, the method comprises contacting Pdx1-positive pancreatic progenitor cells with a concentration of a growth factor from TGF-β superfamily (e.g., Activin A), such as, about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 1 ng/mL, about 1.2 ng/mL, about 1.4 ng/mL, about 1.6 ng/mL, about 1.8 ng/mL, about 2 ng/mL, about 2.2 ng/mL, about 2.4 ng/mL, about 2.6 ng/mL, about 2.8 ng/mL, about 3 ng/mL, about 3.2 ng/mL, about 3.4 ng/mL, about 3.6 ng/mL, about 3.8 ng/mL, about 4 ng/mL, about 4.2 ng/mL, about 4.4 ng/mL, about 4.6 ng/mL, about 4.8 ng/mL, about 5 ng/mL, about 5.2 ng/mL, about 5.4 ng/mL, about 5.6 ng/mL, about 5.8 ng/mL, about 6 ng/mL, about 6.2 ng/mL, about 6.4 ng/mL, about 6.6 ng/mL, about 6.8 ng/mL, about 7 ng/mL, about 8 ng/mL, about 9 ng/mL, about 10 ng/mL, about 20 ng/mL, about 30 ng/mL, or about 50 ng/mL. In some examples, the method comprises contacting Pdx1-positive pancreatic progenitor cells with a concentration of a growth factor from TGF-β superfamily (e.g., Activin A), such as, about 5 ng/mL.

In some cases, the Pdx1-positive, NKX6.1-positive pancreatic progenitor cells are obtained by contacting Pdx1-positive pancreatic progenitor cells under conditions that promote cell clustering with KGF, Sant1, and RA, for a period of 5 days. In some cases, the Pdx1-positive, NKX6.1-positive pancreatic progenitor cells are obtained by contacting Pdx1-positive pancreatic progenitor cells under conditions that promote cell clustering with KGF, Sant1, RA, Y27632, and Activin A, for a period of 5 days. In some cases, the Pdx1-positive, NKX6.1-positive pancreatic progenitor cells are obtained by contacting Pdx1-positive pancreatic progenitor cells under conditions that promote cell clustering with KGF for a period of 5 days. In some cases, the Pdx1-positive, NKX6.1-positive pancreatic progenitor cells are obtained by contacting Pdx1-positive pancreatic progenitor cells in a S3 medium.

Aspects of the disclosure involve insulin-positive endocrine cells. Insulin-positive endocrine cells of use herein can be derived from any source or generated in accordance with any suitable protocol, In some aspects, NKX6.1-positive pancreatic progenitor cells are differentiated to insulin-positive endocrine cells, In some aspects, the insulin-positive endocrine cells are further differentiated, e.g., by induction or maturation to SC-β cells.

In some aspects, a method of producing an insulin-positive endocrine cell from an NKX6.1-positive pancreatic progenitor cell comprises contacting a population of cells (e.g., under conditions that promote cell clustering) comprising NKX6.1-positive pancreatic progenitor cells with a) a TGF-β signaling pathway inhibitor, and b) a thyroid hormone signaling pathway activator, to induce the differentiation of at least one NKX6.1-positive pancreatic progenitor cell in the population into an insulin-positive endocrine cell, wherein the insulin-positive endocrine cell expresses insulin. In some cases, insulin-positive endocrine cells express Pdx1, NKX6.1, NKX2.2, Mafb, glis3, Surn, Kir6.2, Znt8, SLC2A1, SLC2A3 and/or insulin.

Any TGF-β signaling pathway inhibitor capable of inducing the differentiation of NKX6.1-positive pancreatic progenitor cells to differentiate into insulin-positive endocrine cells (e.g., alone, or in combination with other β cell-differentiation factors, e.g., a thyroid hormone signaling pathway activator) can be used. In some cases, the TGF-β signaling pathway comprises TGF-β receptor type I kinase signaling. In some cases, the TGF-β signaling pathway inhibitor comprises Alk5 inhibitor II.

Any thyroid hormone signaling pathway activator capable of inducing the differentiation of NKX6.1-positive pancreatic progenitor cells to differentiate into insulin-positive endocrine cells (e.g., alone, or in combination with other β cell-differentiation factors, e.g., a TGF-β signaling pathway inhibitor) can be used. In some cases, the thyroid hormone signaling pathway activator comprises triiodothyronine (T3).

In some cases, the method comprises contacting the population of cells (e.g., NKX6.1-positive pancreatic progenitor cells) with at least one additional factor. In some cases, the method comprises contacting the Pdx1-positive NKX6.1-positive pancreatic progenitor cells with at least one of i) a SHH pathway inhibitor, ii) a RA signaling pathway activator, iii) a 7-secretase inhibitor, iv) at least one growth factor from the epidermal growth factor (EGF) family, and optionally v) a protein kinase inhibitor.

In some cases, the method comprises contacting the population of cells (e.g., NKX6.1-positive pancreatic progenitor cells) with at least one additional factor. In some cases, the method comprises contacting the Pdx1-positive NKX6.1-positive pancreatic progenitor cells with at least one of i) a SHH pathway inhibitor, ii) a RA signaling pathway activator, iii) a 7-secretase inhibitor, iv) at least one growth factor from the epidermal growth factor (EGF) family, and v) at least one bone morphogenetic protein (BMP) signaling pathway inhibitor.

Any γ-secretase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator). In some cases, the γ-secretase inhibitor comprises XXI. In some cases, the γ-secretase inhibitor comprises DAPT. In some examples, the method comprises contacting NKX6.1-positive pancreatic progenitor cells with a concentration of a 7-secretase inhibitor (e.g., XXI), such as, about 0.01 µM, about 0.02 µM, about 0.05 µM, about 0.075 µM, about 0.1 µM, about 0.2 µM, about 0.3 µM, about 0.4 µM, about 0.5 µM, about 0.6 µM, about 0.7 µM, about 0.8 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 2.9 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.2 µM, about 5.4 µM, about 5.6 µM, about 5.8 µM, about 6 µM, about 6.2 µM, about 6.4 µM, about 6.6 µM, about 6.8 µM, about 7 µM, about 8 µM, about 9 µM, about 10 µM, about 20 µM, about 30 µM, or about 50 µM.

Any growth factor from the EGF family capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some cases, the at least one growth factor from the EGF family comprises betacellulin. In some cases, at least one growth factor from the EGF family comprises EGF. In some examples, the method comprises contacting NKX6.1-positive pancreatic progenitor cells with a concentration of a growth factor from EGF family (e.g., betacellulin), such as, about 1 ng/mL, about 2 ng/mL, about 4 ng/mL, about 6 ng/mL, about 8 ng/mL, about 10 ng/mL, about 12 ng/mL, about 14 ng/mL, about 16 ng/mL, about 18 ng/mL, about 20 ng/mL, about 22 ng/mL, about 24 ng/mL, about 26 ng/mL, about 28 ng/mL, about 30 ng/mL, about 40 ng/mL, about 50 ng/mL, about 75 ng/mL, about 80 ng/mL, about 90 ng/mL, about 95 ng/mL, about 100 ng/mL, about 150 ng/mL, about 200 ng/mL, about 250 ng/mL, or about 300 ng/mL.

Any RA signaling pathway activator capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some cases, the RA signaling pathway activator comprises RA. In some examples, the method comprises contacting NKX6.1-positive pancreatic progenitor cells with a concentration of an RA signaling pathway activator (e.g., retinoic acid), such as, about 0.02 µM, about 0.1 µM, about 0.2 µM, about 0.25 µM, about 0.3 µM, about 0.4 µM, about 0.45 µM, about 0.5 µM, about 0.55 µM, about 0.6 βM, about 0.65 µM, about 0.7 µM, about 0.75 µM, about 0.8 µM, about 0.85 µM, about 0.9 βM, about 1 βM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM.

Any SHH pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used in the method provided herein. In some cases, the SHH pathway inhibitor comprises Sant1. In some examples, the method comprises contacting NKX6.1-positive pancreatic progenitor cells with a concentration of a SHH pathway inhibitor (e.g., Sant1), such as, about 0.001 µM, about 0.002 βM, about 0.005 βM, about 0.01 µM, about 0.02 µM, about 0.03 µM, about 0.05 µM, about 0.08 µM, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM.

Any BMP signaling pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some cases, the BMP signaling pathway inhibitor comprises LDN193189 or DMH-1. In some examples, the method comprises contacting NKX6.1-positive pancreatic progenitor cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 μM.

In some cases, the population of cells is optionally contacted with a protein kinase inhibitor. In some cases, the population of cells is not contacted with the protein kinase inhibitor. In some cases, the population of cells is contacted with the protein kinase inhibitor. Any protein kinase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator). In some cases, the protein kinase inhibitor comprises staurosporine.

In some cases, the method comprises contacting the population of cells (e.g., NKX6.1-positive pancreatic progenitor cells) with XXI, Alk5i, T3, RA, Santi, and betacellulin for a period of 7 days, to induce the differentiation of at least one NKX6.1-positive pancreatic progenitor cell in the population into an insulin-positive endocrine cell, wherein the insulin-positive endocrine cell expresses insulin. In some cases, the method comprises contacting the population of cells (e.g., NKX6.1-positive pancreatic progenitor cells) with XXI, Alk5i, T3, RA, Santi, betacellulin, and LDN193189 for a period of 7 days, to induce the differentiation of at least one NKX6.1-positive pancreatic progenitor cell in the population into an insulin-positive endocrine cell, wherein the insulin-positive endocrine ceil expresses insulin. In some embodiments, one or more differentiation factors are added in a portion of the Stage 5, for instance, only the first 1, 2, 3, 4, 5, or 6 days of the period of time for Stage 5, or the last 1, 2, 3, 4, 5, or 6 days of the period of time for Stage 5. In one example, the cells are contacted with SHH signaling pathway inhibitor for only the first 2, 3, 4, or 5 days during Stage 5, after which the SHH signaling pathway inhibitor is removed from the culture medium. In another example, the cells are contacted with BMP signaling pathway inhibitor for only the first 1, 2, or 3 days during Stage 5, after which the BMP signaling pathway inhibitor is removed from the culture medium.

In some cases, the method comprises culturing the population of cells (e.g., NKX6.1-positive pancreatic progenitor cells) in a BE5 medium, to induce the differentiation of at least one NKX6.1-positive pancreatic progenitor cell in the population into an insulin-positive endocrine cell, wherein the insulin-positive endocrine cell expresses insulin.

Aspects of the disclosure involve generating pancreatic β cells (e.g., non-native pancreatic β cells). Non-native pancreatic β cells, in some cases, resemble endogenous mature 3 cells in form and function, but nevertheless are distinct from native β cells.

In some cases, the insulin-positive pancreatic endocrine cells generated using the method provided herein can form a cell cluster, alone or together with other types of cells, e.g., precursors thereof, e.g., stem cell, definitive endoderm cells, primitive gut tube cell, Pdx1-positive pancreatic progenitor cells, or NKX6.1-positive pancreatic progenitor cells.

In some cases, the cell population comprising the insulin-positive endocrine cells can be directly induced to mature into SC-β cells without addition of any exogenous differentiation factors (such as inhibitor of TGF-β signaling pathway, thyroid hormone signaling pathway activator, PKC activator, growth factors from TGF-β superfamily, FGF family, or EGF family, SHH signaling pathway inhibitor, γ-secretase inhibitor, ROCK inhibitor, or BMP signaling pathway inhibitor).

In some cases, the cell population comprising the insulin-positive endocrine cells can be directly induced to mature into SC-β cells by contacting the insulin-positive endocrine cells with differentiation factors. The differentiation factors can comprise at least one inhibitor of TGF-β signaling pathway and thyroid hormone signaling pathway activator as described herein. In some cases, SC-β cells can be obtained by contacting a population of cells comprising insulin-positive endocrine cells with Alk5i and T3.

In some examples, insulin-positive endocrine cells can be matured in a NS-GFs medium, MCDB131 medium, DMEM medium, or CMRL medium. In some cases, the insulin-positive endocrine cells can be matured in a CMRLs medium supplemented with 10% FBS. In some cases, the insulin-positive endocrine cells can be matured in a DMEM medium supplemented with 1% HSA. In other cases, SC-β cells can be obtained by culturing the population of cells containing the insulin-positive endocrine cells in a MCDB131 medium that can be supplemented by 2% BSA. In some cases, the MCDB131 medium with 2% BSA for maturation of insulin-positive endocrine cells into SC-β cells can be comprise no small molecule factors as described herein. In some case, the MCDB131 medium with 2% BSA for maturation of insulin-positive endocrine cells into SC-β cells can comprise no serum (e.g., no FBS).

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, optionally vi) at least one growth factor from the epidermal growth factor (EGF) family, and optionally vii) a BMP signaling pathway inhibitor, every other day for a period of between five and seven days; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature R cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor, v) a PKC activator, vi) a ROCK inhibitor, and vii) a growth factor from TGFβ superfamily, for a period of 2 days; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, optionally vi) at least one growth factor from the epidermal growth factor (EGF) family, and optionally vii) a BMP signaling pathway inhibitor, every other day for a period of between five and seven days; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a PKC activator, and v) a ROCK inhibitor; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a 7-secretase inhibitor, and optionally vi) at least one growth factor from the epidermal growth factor (EGF) family, every other day for a period of between five and seven days; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

The medium used to culture the cells dissociated from the first cell cluster can be xeno-free. A xeno-free medium for culturing cells and/or cell clusters of originated from an animal can have no product from other animals. In some cases, a xeno-free medium for culturing human cells and/or cell clusters can have no products from any non-human animals. For example, a xeno-free medium for culturing human cells and/or cell clusters can comprise human platelet lysate (PLT) instead of fetal bovine serum (FBS). For example, a medium can comprise from about 1% to about 20%, from about 5% to about 15%, from about 8% to about 12%, from about 9 to about 11% serum. In some cases, medium can comprise about 10% of serum. In some cases, the medium can be free of small molecules and/or FBS. For example, a medium can comprise MCDB131 basal medium supplemented with 2% BSA. In some cases, the medium is serum-free. In some examples, a medium can comprise no exogenous small molecules or signaling pathway agonists or antagonists, such as, growth factor from fibroblast growth factor family (FGF, such as FGF2, FGF8B, FGF 10, or FGF21), Sonic Hedgehog Antagonist (such as Santi, Sant2, Sant4, Sant4, Cur61414, forskolin, tomatidine, AY9944, triparanol, cyclopamine, or derivatives thereof), Retinoic Acid Signaling agonist (e.g., retinoic acid, CD1530, AM580, TTHPB, CD437, Ch55, BMS961, AC261066, AC55649, AM80, BMS753, tazarotene, adapalene, or CD2314), inhibitor of Rho-associated, coiled-coil containing protein kinase (ROCK) (e.g., Thiazovivin, Y-27632, Fasudil/HA1077, or 14-1152), activator of protein kinase C (PKC) (e.g., phorbol 12,13-dibutyrate (PDBU), TPB, phorbol 12-myristate 13-acetate, bryostatin 1, or derivatives thereof), antagonist of TGF 3 super family (e.g., Alk5 inhibitor II (CAS 446859-33-2), A83-01, SB431542, D4476, GW788388, LY364947, LY580276, SB505124, GW6604, SB-525334, SD-208, SB-505124, or derivatives thereof), inhibitor of Bone Morphogenetic Protein (BMP) type 1 receptor (e.g., LDN193189 or derivatives thereof), thyroid hormone signaling pathway activator (e.g., T3 or derivatives thereof), gamma-secretase inhibitor (e.g., XXI, DAPT, or derivatives thereof), activator of TGF-β signaling pathway (e.g., WNT3a or Activin A) growth factor from epidermal growth factor (EGF) family (e.g., betacellulin or EGF), broad kinase (e.g., staurosporine or derivatives thereof), non-essential amino acids, vitamins or antioxidants (e.g., cyclopamine, vitamin D, vitamin C, vitamin A, or derivatives thereof), or other additions like N-acetyl cysteine, zinc sulfate, or heparin. In some cases, the reaggregation medium can comprise no exogenous extracellular matrix molecule. In some cases, the reaggregation medium does not comprise Matrigel™. In some cases, the reaggregation medium does not comprise other extracellular matrix molecules or materials, such as, collagen, gelatin, poly-L-lysine, poly-D-lysine, vitronectin, laminin, fibronectin, PLO laminin, fibrin, thrombin, and RetroNectin and mixtures thereof, for example, or lysed cell membrane preparations.

A person of ordinary skill in the art will appreciate that that the concentration of serum albumin supplemented into the medium may vary. For example, a medium (e.g., MCDB131) can comprise about 0.01%, 0.05%, 0.1%, 1%, about 2%, about 3%, about 4%, about 5%, about 10%, or about 15% BSA. In other cases, a medium can comprise about 0.01%, 0.05%, 0.1%, 1%, about 2%, about 3%, about 4%, about 5%, about 10%, or about 15% HSA. The medium used (e.g., MCDB131 medium) can contain components not found in traditional basal media, such as trace elements, putrescine, adenine, thymidine, and higher levels of some amino acids and vitamins. These additions can allow the medium to be supplemented with very low levels of serum or defined components. The medium can be free of proteins and/or growth factors, and may be supplemented with EGF, hydrocortisone, and/or glutamine. The medium can comprise one or more extracellular matrix molecules (e.g., extracellular proteins). Non-limiting exemplary extracellular matrix molecules used in the medium can include collagen, placental matrix, fibronectin, laminin, merosin, tenascin, heparin, heparin sulfate, chondroitin sulfate, dermatan sulfate, aggrecan, biglycan, thrombospondin, vitronectin, and decorin. In some cases, the medium comprises laminin, such as LN-332. In some cases, the medium comprises heparin.

The medium can be changed periodically in the culture, e.g., to provide optimal environment for the cells in the medium. When culturing the cells dissociated from the first cell cluster for re-aggregation, the medium can be changed at least or about every 4 hours, 12 hours, 24 hours, 48 hours, 3 days or 4 days. For example, the medium can be changed about every 48 hours.

In some cases, cells can be cultured under dynamic conditions (e.g., under conditions in which the cells are subject to constant movement or stirring while in the suspension culture). For dynamic culturing of cells, the cells can be cultured in a container (e.g., an non-adhesive container such as a spinner flask (e.g., of 200 ml to 3000 ml, for example 250 ml; of 100 ml; or in 125 ml Erlenmeyer), which can be connected to a control unit and thus present a controlled culturing system. In some cases, cells can be cultured under non-dynamic conditions (e.g., a static culture) while preserving their proliferative capacity. For non-dynamic culturing of cells, the cells can be cultured in an adherent culture vessel. An adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, fibronectin, PLO laminin, fibrin, thrombin, and RetroNectin and mixtures thereof, for example, Matrigel™, and lysed cell membrane preparations.

Medium in a dynamic cell culture vessel (e.g., a spinner flask) can be stirred (e.g., by a stirrer). The spinning speed can correlate with the size of the re-aggregated second cell cluster. The spinning speed can be controlled so that the size of the second cell cluster can be similar to an endogenous pancreatic islet. In some cases, the spinning speed is controlled so that the size of the second cell cluster can be from about 75 µm to about 250 µm. The spinning speed of a dynamic cell culture vessel (e.g., a spinner flask) can be about 20 rounds per minute (rpm) to about 100 rpm, e.g., from about 30 rpm to about 90 rpm, from about 40 rpm to about 60 rpm, from about 45 rpm to about 50 rpm. In some cases, the spinning speed can be about 50 rpm.

Stage 6 cells as provided herein may or may not be subject to the dissociation and reaggregation process as described herein. In some cases, the cell cluster comprising the insulin-positive endocrine cells can be reaggregated. The reaggregation of the cell cluster can enrich the insulin-positive endocrine cells. In some cases, the insulin-positive endocrine cells in the cell cluster can be further matured into pancreatic β cells. For example, after reaggregation, the second cell cluster can exhibit in vitro GSIS, resembling native pancreatic islet. For example, after reaggregation, the second cell cluster can comprise non-native pancreatic β cell that exhibits in vitro GSIS. In some embodiments, the reaggregation process can be performed according to the disclosure of PCT application PCT/US2018/043179, which is incorporated herein by reference in its entirety.

In some embodiments, the present disclosure relates to cryopreservation of the non-native pancreatic β cells or precursors thereof obtained using the methods provided herein. In some embodiments, the cell population comprising non-native pancreatic β cells can be stored via cryopreservation. For instances, the cell population comprising non-native β cells, e.g., Stage 6 cells in some cases, can be dissociated into cell suspension, e.g., single cell suspension, and the cell suspension can be cryopreserved, e.g., frozen in a cryopreservation solution. The dissociation of the cells can be conducted by any of the technique provided herein, for example, by enzymatic treatment. The cells can be frozen at a temperature of at highest −20° C., at highest −30° C., at highest −40° C., at highest −50° C., at highest −60° C., at highest −70° C., at highest −80° C., at highest −90° C., at highest −100° C., at highest −110° C., at highest −120° C., at highest −130° C., at highest −140° C., at highest −150° C., at highest −160° C., at highest −170° C., at highest −180° C., at highest −190° C., or at highest −200° C. In some cases, the cells are frozen at a temperature of about −80° C. In some cases, the cells are frozen at a temperature of about −195° C. Any cooling methods can be used for providing the low temperature needed for cryopreservation, such as, but not limited to, electric freezer, solid carbon dioxide, and liquid nitrogen. In some cases, any cryopreservation solution available to one skilled in the art can be used for incubating the cells for storage at low temperature, including both custom made and commercial solutions. For example, a solution containing a cryoprotectant can be used. The cryoprotectant can be an agent that is configured to protect the cell from freezing damage. For instance, a cryoprotectant can be a substance that can lower the glass transition temperature of the cryopreservation solution. Exemplary cryoprotectants that can be used include DMSO (dimethyl sulfoxide), glycols (e.g., ethylene glycol, propylene glycol and glycerol), dextran (e.g., dextran-40), and trehalose. Additional agents can be added in to the cryopreservation solution for other effects. In some cases, commercially available cryopreservation solutions can be used in the method provided herein, for instance, FrostaLife™, pZerve™, Prime-XV©, Gibco Synth-a-Freeze Cryopreservation Medium, STEM-CELL-BANKER®, CryoStor® Freezing Media, HypoThermosol® FRS Preservation Media, and CryoDefend® Stem Cells Media.

V. Differentiation Factors

Aspects of the disclosure relate to contacting progenitor cells (e.g., stem cells, e.g., iPS cells, definitive endoderm cells, primitive gut tube cells, Pdx1-positive pancreatic progenitor cells, NKX6.1-positive pancreatic progenitor cells, insulin-positive endocrine cells) with β cell differentiation factors, for example, to induce the maturation of the insulin-positive endocrine cells or differentiation of other progenitor cells into SC-β cells (e.g., mature pancreatic β cells). In some embodiments, the differentiation factor can induce the differentiation of pluripotent cells (e.g., iPSCs or hESCs) into definitive endoderm cells, e.g., in accordance with a method described herein. In some embodiments, the differentiation factor can induce the differentiation of definitive endoderm cells into primitive gut tube cells, e.g., in accordance with a method described herein. In some embodiments, the differentiation factor can induce the differentiation of primitive gut tube cells into Pdx1-positive pancreatic progenitor cells, e.g., in accordance with a method described herein. In some embodiments, the differentiation factor can induce the differentiation of Pdx1-positive pancreatic progenitor cells into NKX6-1-positive pancreatic progenitor cells, e.g., in accordance with a method described herein. In some embodiments, the differentiation factor can induce the differentiation of NKX6-1-positive pancreatic progenitor cells into insulin-positive endocrine cells, e.g., in accordance with a method described herein. In some embodiments, the differentiation factor can induce the maturation of insulin-positive endocrine cells into SC-β cells, e.g., in accordance with a method described herein.

At least one differentiation factor described herein can be used alone, or in combination with other differentiation actors, to generate SC-β cells according to the methods as disclosed herein. In some embodiments, at least two, at least three, at least four, at least five, at least six, at least seven, at least eight, at least nine, or at least ten differentiation factors described herein are used in the methods of generating SC-β cells.

Transforming Growth Factor-β (TGF-β) Superfamily

Aspects of the disclosure relate to the use of growth factors from the transforming growth factor-β (TGF-β) superfamily as differentiation factors. The "TGF-β superfamily" means proteins having structural and functional characteristics of known TGFβ family members. The TGFβ family of proteins can include the TGFβ series of proteins, the Inhibins (including Inhibin A and Inhibin B), the Activins (including Activin A, Activin B, and Activin AB), MIS (Müllerian inhibiting substance), BMP (bone morphogenetic proteins), dpp (decapentaplegic), Vg-1, MNSF (monoclonal nonspecific suppressor factor), and others. Activity of this family of proteins can be based on specific binding to certain receptors on various cell types. Members of this family can share regions of sequence identity, particularly at the C-terminus, that correlate to their function. The TGFβ family can include more than one hundred distinct proteins, all sharing at least one region of amino acid sequence identity. Members of the family that can be used in the method disclosed herein can include, but are not limited to, the following proteins, as identified by their GenBank accession numbers: P07995, P18331, P08476, Q04998, P03970, P43032, P55102, P27092, P42917, P09529, P27093, P04088, Q04999, P17491, P55104, Q9WUK5, P55103, O88959, O08717, P58166, O61643, P35621, P09534, P48970, Q9NR23, P25703, P30884, P12643, P49001, P21274, O46564, O19006, P22004, P20722, Q04906, Q07104, P30886, P18075, P23359, P22003, P34821, P49003, Q90751, P21275, Q06826, P30885, P34820, Q29607, P12644, Q90752, O46576, P27539, P48969, Q26974, P07713, P91706, P91699, P27091, O42222, Q24735, P20863, O18828, P55106, Q9PTQ2, O14793, O08689, O42221, O18830, O18831, O18836, O35312, O42220, P43026, P43027, P43029, O95390, Q9R229, 093449, Q9Z1W4, Q9BDW8, P43028, Q7Z4P5, P50414, P17246, P54831, PO4202, P01137, P09533, P18341, O19011, Q9Z1Y6, P07200, Q9Z217, O95393, P55105, P30371, Q9MZE2, Q07258, Q96S42, P97737, AAA97415.1, NP-776788.1, NP-058824.1, EAL24001.1, 1 S4Y, NP-001009856.1, NP-1-032406.1, NP-999193.1, XP-519063.1, AAG17260.1, CAA40806.1, NP-1-001009458.1, AAQ55808.1, AAK40341.1, AAP33019.1, AAK21265.1, AAC59738.1, CA146003.1, B40905, AAQ55811.1, AAK40342.1, XP-540364.1, P55102, AAQ55810.1, NP-990727.1, CAA51163.1, AAD50448.1, JC4862, PN0504, BAB17600.1, AAH56742.1, BAB17596.1, CAG06183.1, CAG05339.1, BAB17601.1, CAB43091.1, A36192, AAA49162.1, AAT42200.1, NP-789822.1, AAA59451.1, AAA59169.1, XP-541000.1, NP-990537.1, NP-1-002184.1, AAC14187.1, AAP83319.1, AAA59170.1, BAB16973.1, AAM66766.1, WFPGBB, 1201278C, AAH30029.1, CAA49326.1, XP-344131.1, AA-148845.1, XP-1-148966.3, 148235, B41398, AAH77857.1, AAB26863.1, 1706327A, BAA83804.1, NP-571143.1, CAG00858.1, BAB17599.1, BAB17602.1, AAB61468.1, PN0505, PN0506, CAB43092.1, BAB17598.1, BAA22570.1, BAB16972.1, BAC81672.1, BAA12694.1, BAA08494.1, B36192, C36192, BAB16971.1, NP-034695.1, AAA49160.1, CAA62347.1, AAA49161.1, AAD30132.1, CAA58290.1, NP-005529.1, XP-522443.1, AAM27448.1, XP-538247.1, AAD30133. I, AAC36741.1, AAH10404.1, NP-032408.1, AANO3682.1, XP-509161.1, AAC32311.1, NP-651942.2, AAL51005.1, AAC39083.1, AAH85547.1, NP-571023.1, CAF94113.1, EAL29247.1, AAW30007.1, AAH90232.1, A29619, NP-001007905.1, AAH73508.1, AADO22O1.1, NP-999793.1, NP-990542.1, AAF19841.1, AAC97488.1, AAC60038.1, NP 989197.1, NP-571434.1, EAL41229.1, AAT07302.1, CA119472.1, NP-031582.1, AAA40548.1, XP-535880.1, NP-1-037239.1, AAT72007.1, XP-418956.1, CAA41634.1, BAC30864.1, CAA38850.1, CAB81657.2, CAA45018.1, CAA45019.1, BAC28247.1, NP-031581.1, NP-990479.1, NP-999820.1, AAB27335.1, S45355, CAB82007.1, XP-534351.1, NP-058874.1, NP-031579.1, IREW, AAB96785.1, AAB46367.1, CAA05033.1, BAA89012.1, IES7, AAP20870.1, BAC24087.1, AAG09784.1, BAC06352.1, AAQ89234.1, AAM27000.1, AAH30959.1, CAGO1491.1, NP-571435.1, 1REU, AAC60286.1, BAA24406.1, A36193, AAH55959.1, AAH54647.1, AAH90689.1, CAG09422.1, BAD16743.1, NP-032134.1, XP-532179.1, AAB24876.1, AAH57702.1, AAA82616.1, CAA40222.1, CAB90273.2, XP-342592.1, XP-534896.1, XP-534462.1, 1LXI, XP-417496.1, AAF34179.1, AAL73188.1, CAF96266.1, AAB34226.1, AAB33846.1, AAT12415.1, AA033819.1, AAT72008.1, AAD38402.1, BAB68396.1, CAA45O21.1, AAB27337.1, AAP69917.1, AAT12416.1, NP-571396.1, CAA53513.1, AA033820.1, AAA48568.1, BAC02605.1, BAC02604.1, BAC02603.1, BAC02602.1, BAC02601.1, BAC02599.1, BAC02598.1, BAC02597.1, BAC02595.1, BAC02593.1, BAC02592.1, BAC02590.1, AAD28039.1, AAP74560.1, AAB94786.1, NP-001483.2, XP-528195.1, NP-571417.1, NP-001001557. I, AAH43222.1, AAM33143.1, CAG10381.1, BAA31132.1, EAL39680.1, EAA12482.2, P34820, AAP88972.1, AAP74559.1, CA116418.1, AAD30538.1, XP-345502.1, NP-1-038554.1, CAG04089.1, CAD60936.2, NP-031584.1, B55452, AAC60285.1, BAA06410.1, AAH52846.1, NP-031580.1, NP-1-036959.1, CAA45836.1, CAA45020.1, Q29607, AAB27336.1, XP-547817.1, AAT12414.1, AAM54049.1, AAH78901.1, AA025745.1, NP-570912.1, XP-392194.1, AAD20829.1, AAC97113.1, AAC61694.1, AAH60340.1, AAR97906.1, BAA32227.1, BAB68395.1, BAC02895.1, AAWS 1451.1, AAF82188.1, XP-544189.1, NP-990568.1, BAC80211.1, AAW82620.1, AAF99597.1, NP-571062.1, CAC44179.1, AAB97467.1, AAT99303.1, AAD28038.1, AAH52168.1, NP-001004122.1, CAA72733.1, NP-032133.2, XP-394252.1, XP-224733.2, JH0801, AAP97721.1, NP-989669.1, S43296, P43029, A55452, AAH32495.1, XP-542974.1, NP-032135.1, AAK30842.1, AAK27794.1, BAC30847.1, EAA12064.2, AAP97720.1, XP-525704.1, AAT07301.1, BAD07014.1, CAF94356.1, AAR27581.1, AAG13400.1, AAC60127.1, CAF92055.1, XP-540103.1, AA020895.1, CAF97447.1, AAS01764.1, BAD08319.1, CAA10268.1, NP-998140.1, AAR03824.1, AAS48405.1, AAS48403.1, AAK53545.1, AAK84666.1, XP-395420.1, AAK56941.1, AAC47555.1, AAR88255.1, EAL33036.1, AAW47740.1, AAW29442.1, NP-722813.1, AAR08901.1, AAO 15420.2, CAC59700.1, AAL26886.1, AAK71708.1, AAK71707.1, CAC51427.2, AAK67984.1, AAK67983.1, AAK28706.1, P07713, P91706, P91699, CAG02450.1, AAC47552.1, NP-005802.1, XP-343149.1, AW34055.1, XP-538221.1, AAR27580.1, XP-125935.3, AAF21633.1, AAF21630.1, AAD05267.1, Q9Z1 W4, NP-1-031585.2, NP-571094.1, CAD43439.1, CAF99217.1, CAB63584.1, NP-722840.1, CAE46407.1, XP-1-417667.1, BAC53989.1, BAB19659.1, AAM46922.1, AAA81169.1, AAK28707.1, AAL05943.1, AAB17573.1, CAH25443.1, CAG10269.1, BAD16731.1, EAA00276.2, AAT07320.1, AAT07300.1, AAN15037.1, CAH25442.1, AAK08152.2, 2009388A, AAR12161.1, CAGO1961.1, CAB63656.1, CAD67714.1, CAF94162.1, NP-477340.1, EAL24792.1, NP-1-001009428.1, AAB86686.1, AAT40572.1, AAT40571.1, AAT40569.1, NP-033886.1, AAB49985.1, AAG39266.1, Q26974, AAC77461.1, AAC47262.1, BAC05509.1, NP-055297.1, XP-546146.1, XP-525772.1, NP-060525.2, AAH33585.1, AAH69080.1, CAG12751.1, AAH74757.2, NP-034964.1, NP-038639.1, 042221, AAF02773.1, NP-062024.1, AAR18244.1, AAR14343.1, XP-228285.2, AAT40573.1, AAT94456.1, AAL35278.1, AAL35277.1, AAL17640.1, AAC08035.1, AAB86692.1, CAB40844.1, BAC38637.1, BAB16046.1, AAN63522.1, NP-571041.1, AAB04986.2, AAC26791.1, AAB95254.1, BAA11835.1, AAR18246.1, XP-538528.1, BAA31853.1, AAK18000.1, XP-1-420540.1, AAL35276.1, AAQ98602.1, CAE71944.1, AAW50585.1, AAV63982.1, AAW29941.1, AAN87890.1, AAT40568.1, CAD57730.1, AAB81508.1, AAS00534.1, AAC59736.1, BAB79498.1, AAA97392.1, AAP85526.1, NP-999600.2, NP-878293.1, BAC82629.1, CAC60268.1, CAG04919.1, AAN10123.1, CAA07707.1 AAK20912.1, AAR88254.1, CAC34629.1, AAL35275.1, AAD46997. I, AAN03842.1, NP-571951.2, CAC50881.1, AAL99367.1, AAL49502.1, AAB71839.1, AAB65415.1, NP-624359.1, NP-990153.1, AAF78069.1, AAK49790.1, NP-919367.2, NP-001192.1, XP-544948.1, AAQ18013.1, AAV38739.1, NP-851298.1, CAA67685.1, AAT67171.1, AAT37502.1, AAD27804.1, AAN76665.1, BAC11909.1, XP-1-421648.1, CAB63704.1, NP-037306.1, A55706, AAF02780.1, CAG09623.1, NP-067589.1, NP-035707.1, AAV30547.1, AAP49817.1, BAC77407.1, AAL87199.1, CAG07172.1, B36193, CAA33024.1, NP-1-001009400.1, AAP36538.1, XP-512687.1, XP-510080.1, AAH05513.1, 1KTZ, AAH14690.1, AAA31526.1.

The growth factor from the TGF-β superfamily in the methods and compositions provided herein can be naturally obtained or recombinant. In some embodiments, the growth factor from the TGF-β superfamily comprises Activin A. The term "Activin A" can include fragments and derivatives of Activin A. The sequence of an exemplary Activin A (SEQ ID NO: 1) is disclosed as SEQ ID NO: 1 in U.S. Pub. No. 2009/0155218 (the '218 publication). Other non-limiting examples of Activin A (SEQ ID NOS 2-16) are provided in SEQ ID NO: 2-16 of the '218 publication, and non-limiting examples of nucleic acids encoding Activin A (SEQ ID NOS 17-18) are provided in SEQ ID NO:33-34 of the '218 publication. In some embodiments, the growth factor from the TGF-β superfamily can comprise a polypeptide having an amino acid sequence at least 30%, at least 40%, at least 50%, at least 60%, at least 70%, at least 80%, at least 90%, at least 95%, or at least 99%, or greater identical to SEQ ID NO: 1, which is disclosed as SEQ ID NO: 1 of the '218 publication.

In some embodiments, the growth factor from the TGF-β superfamily comprises growth differentiation factor 8 (GDF8). The term "GDF8" can include fragments and derivatives of GDF8. The sequences of GDF8 polypeptides are available to the skilled artisan. In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF8 polypeptide sequence (GenBank Accession EAX10880).

In some embodiments, the growth factor from the TGF-β superfamily comprises a growth factor that is closely related to GDF8, e.g., growth differentiation factor 11 (GDF11). In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF11 polypeptide sequence (GenBank Accession AAF21630).

In some embodiments, the growth factor from the TGF-β superfamily can be replaced with an agent mimics the at least one growth factor from the TGF-β superfamily. Exemplary agents that mimic the at least one growth factor from the TGF-β superfamily, include, without limitation, IDE1 and IDE2.

Bone Morphogenetic Protein (BMP) Signaling Pathway Inhibitors

Aspects of the disclosure relate to the use of BMP signaling pathway inhibitors as β cell differentiation factors. The BMP signaling family is a diverse subset of the TGF-β superfamily (Sebald et al. Biol. Chem. 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. Cell Signal 16:291-299, 2004). Soluble BMP antagonists such as noggin, chordin, gremlin, and follistatin limit BMP signaling by ligand sequestration.

In some embodiments, the BMP signaling pathway inhibitor in the methods and composition provided herein comprises DMH-1, or a derivative, analogue, or variant thereof. In some embodiments, the BMP signaling pathway inhibitor in the methods and composition provided herein comprises the following compound (Formula A) or a derivative, analogue, or variant of the following compound (Formula A):

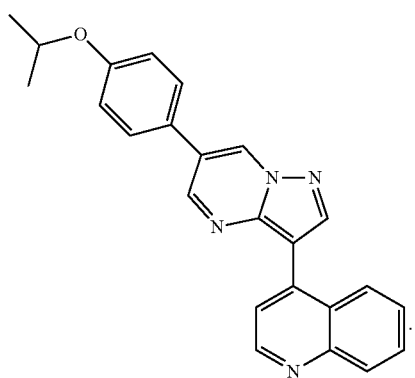

(A)

In some embodiments, the BMP signaling pathway inhibitor in the methods and composition provided herein comprises LDN193189 (also known as LDN193189, 1062368-24-4, LDN-193189, DM 3189, DM-3189, IUPAC Name: 4-[6-(4-piperazin-1-ylphenyl)pyrazolo[1,5-a]pyrimidin-β-yl]quinolone). In some embodiments, the BMP signaling pathway inhibitor in the methods and composition provided herein comprises the following compound or a derivative, analogue, or variant of the following compound:

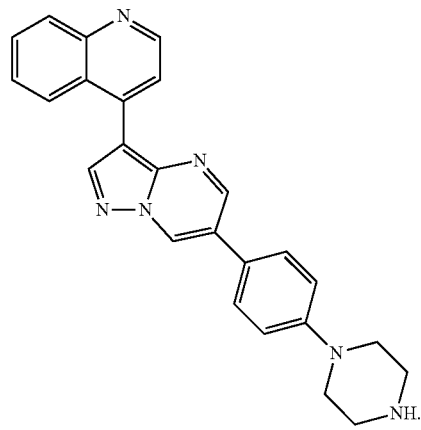 [SMILES: c1ccc2c(-c3cnn4cc(-c5ccc(N6CCNCC6)cc5)cnc34)ccnc2c1]

In some cases, DMH-1 can be more selective as compared to LDN193189. In some embodiments of the present disclosure, DMH-1 can be particularly useful for the methods provided herein. In some embodiments, the methods and compositions provided herein exclude use of LDN193189. In some embodiments, the methods and compositions provided herein exclude use of LDN193189, or a derivative, analogue, or variant thereof for generating Pdx1-positive pancreatic progenitor cells from primitive gut tube cells. In some embodiments, the methods and compositions provided herein relate to use of DMH-1, or a derivative, analogue, or variant thereof for generating Pdx1-positive pancreatic progenitor cells from primitive gut tube cells.

In some embodiments, the BMP signaling pathway inhibitor in the methods and composition provided herein comprise an analog or derivative of LDN193189, e.g., a salt, hydrate, solvent, ester, or prodrug of LDN193189. In some embodiments, a derivative (e.g., salt) of LDN193189 comprises LDN193189 hydrochloride.

In some embodiments, the BMP signaling pathway inhibitor in the methods and composition provided herein comprises a compound of Formula I from U.S. Patent Publication No. 2011/0053930.

TGF-β Signaling Pathway Inhibitors

Aspects of the disclosure relate to the use of TGF-β signaling pathway inhibitors as β cell differentiation factors.

In some embodiments, the TGF-β signaling pathway comprises TGF-β receptor type I kinase (TGF-β RI) signaling. In some embodiments, the TGF-β signaling pathway inhibitor comprises ALK5 inhibitor II (CAS 446859-33-2, an ATP-competitive inhibitor of TGF-B RI kinase, also known as RepSox, IUPAC Name: 2-[5-(6-methylpyridin-2-yl)-1H-pyrazol-4-yl]-1,5-naphthyridine. In some embodiments, the TGF-β signaling pathway inhibitor is an analog or derivative of ALK5 inhibitor II.

In some embodiments, the analog or derivative of ALK5 inhibitor II (also named "ALK5i") is a compound of Formula I as described in U.S. Patent Publication No. 2012/0021519, incorporated by reference herein in its entirety.

In some embodiments, the TGF-β signaling pathway inhibitor in the methods and compositions provided herein is a TGF-β receptor inhibitor described in U.S. Patent Publication No. 2010/0267731. In some embodiments, the TGF-β signaling pathway inhibitor in the methods and compositions provided herein comprises an ALK5 inhibitor described in U.S. Patent Publication Nos. 2009/0186076 and 2007/0142376. In some embodiments, the TGF-β signaling pathway inhibitor in the methods and compositions provided herein is A 83-01. In some embodiments, the TGF-β signaling pathway inhibitor in the methods and compositions provided herein is not A 83-01. In some embodiments, the compositions and methods described herein exclude A 83-01. In some embodiments, the TGF-β signaling pathway inhibitor in the methods and compositions provided herein is SB 431542. In some embodiments, the TGF-β signaling pathway inhibitor is not SB 431542. In some embodiments, the compositions and methods described herein exclude SB 431542. In some embodiments, the TGF-β signaling pathway inhibitor in the methods and compositions provided herein is D 4476. In some embodiments, the TGF-β signaling pathway inhibitor is not D 4476. In some embodiments, the compositions and methods described herein exclude D 4476. In some embodiments, the TGF-β signaling pathway inhibitor in the methods and compositions provided herein is GW 788388. In some embodiments, the TGF-β signaling pathway inhibitor is not GW 788388. In some embodiments, the compositions and methods described herein exclude GW 788388. In some embodiments, the TGF-β signaling pathway inhibitor in the methods and compositions provided herein is LY 364947. In some embodiments, the TGF-β signaling pathway inhibitor is not LY 364947. In some embodiments, the compositions and methods described herein exclude LY 364947. In some embodiments, the TGF-β signaling pathway inhibitor in the methods and compositions provided herein is LY 580276. In some embodiments, the TGF-β signaling pathway inhibitor is not LY 580276. In some embodiments, the compositions and methods described herein exclude LY 580276. In some embodiments, the TGF-β signaling pathway inhibitor in the methods and compositions provided herein is SB 525334. In some embodiments, the TGF-β signaling pathway inhibitor is not SB 525334. In some embodiments, the compositions and methods described herein exclude SB 525334. In some embodiments, the TGF-β signaling pathway inhibitor in the methods and compositions provided herein is SB 505124. In some embodiments, the TGF-β signaling pathway inhibitor is not SB 505124. In some embodiments, the compositions and methods described herein exclude SB 505124. In some embodiments, the TGF-β signaling pathway inhibitor in the methods and compositions provided herein is SD 208. In some embodiments, the TGF-β signaling pathway inhibitor is not SD 208. In some embodiments, the compositions and methods described herein exclude SD 208. In some embodiments, the TGF-β signaling pathway inhibitor in the methods and compositions provided herein is GW 6604. In some embodiments, the TGF-β signaling pathway inhibitor is not GW 6604. In some embodiments, the compositions and methods described herein exclude GW 6604. In some embodiments, the TGF-β signaling pathway inhibitor in the methods and compositions provided herein is GW 788388. In some embodiments, the TGF-β signaling pathway inhibitor in the methods and compositions provided herein is not GW 788388. In some embodiments, the compositions and methods described herein exclude GW 788388.

From the collection of compounds described above, the following can be obtained from various sources: LY-364947, SB-525334, SD-208, and SB-505124 available from Sigma, P.O. Box 14508, St. Louis, Mo., 63178-9916; 616452 and 616453 available from Calbiochem (EMD Chemicals, Inc.), 480 S. Democrat Road, Gibbstown, N.J., 08027; GW788388 and GW6604 available from GlaxoSmithKline, 980 Great West Road, Brentford, Middlesex, TW8 9GS, United Kingdom; LY580276 available from Lilly Research, Indianapolis, Ind. 46285; and SM16 available from Biogen Idec, P.O. Box 14627, 5000 Davis Drive, Research Triangle Park, N.C., 27709-4627.

WNT Signaling Pathway

Aspects of the disclosure relate to the use of activators of the WNT signaling pathway as β cell differentiation factors.

In some embodiments, the WNT signaling pathway activator in the methods and compositions provided herein comprises CHIR99021. In some embodiments, the WNT signaling pathway activator in the methods and compositions provided herein comprises a derivative of CHIR99021, e.g., a salt of CHIR99021, e.g., trihydrochloride, a hydrochloride salt of CHIR99021. In some embodiments, the WNT signaling pathway activator in the methods and compositions provided herein comprises Wnt3a recombinant protein. In some embodiments, the WNT signaling pathway activator in the methods and compositions provided herein comprises a glycogen synthase kinase 3 (GSK3) inhibitor. Exemplary GSK3 inhibitors include, without limitation, 3F8, A 1070722, AR-A 014418, BIO, BIO-acetoxime, FRATide, 10Z-Hymenialdisine, Indirubin-3'oxime, kenpaullone, L803, L803-mts, lithium carbonate, NSC 693868, SB 216763, SB 415286, TC-G 24, TCS 2002, TCS 21311, TWS 119, and analogs or derivatives of any of these. In certain embodiments, the methods, compositions, and kits disclosed herein exclude a WNT signaling pathway activator.

Fibroblast Growth Factor (FGF) Family

Aspects of the disclosure relate to the use of growth factors from the FGF family as β cell differentiation factors.

In some embodiments, the growth factor from the FGF family in the methods and compositions provided herein comprises keratinocyte growth factor (KGF). The polypeptide sequences of KGF are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human KGF polypeptide sequence (GenBank Accession AAB21431).

In some embodiments, the growth factor from the FGF family in the methods and composition provided herein comprises FGF2. The polypeptide sequences of FGF2 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF2 polypeptide sequence (GenBank Accession NP 001997).

In some embodiments, the at least one growth factor from the FGF family in the methods and composition provided herein comprises FGF8B. The polypeptide sequences of FGF8B are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF8B polypeptide sequence (GenBank Accession AAB40954).

In some embodiments, the at least one growth factor from the FGF family in the methods and composition provided herein comprises FGF10. The polypeptide sequences of FGF10 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF10 polypeptide sequence (GenBank Accession CAG46489).

In some embodiments, the at least one growth factor from the FGF family in the methods and composition provided herein comprises FGF21. The polypeptide sequences of FGF21 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF21 polypeptide sequence (GenBank Accession AAQ89444.1).

Sonic Hedgehog (SHH) Signaling Pathway

Aspects of the disclosure relate to the use of SHH signaling pathway inhibitors as β cell differentiation factors.

In some embodiments, the SHH signaling pathway inhibitor in the methods and composition provided herein comprises Sant1. In some embodiments, the SHH signaling pathway inhibitor in the methods and composition provided herein comprises SANT2. In some embodiments, the SHH signaling pathway inhibitor in the methods and composition provided herein comprises SANT3. In some embodiments, the SHH signaling pathway inhibitor in the methods and composition provided herein comprises SANT4. In some embodiments, the SHH signaling pathway inhibitor comprises Cur61414. In some embodiments, the SHH signaling pathway inhibitor in the methods and composition provided herein comprises forskolin. In some embodiments, the SHH signaling pathway inhibitor in the methods and composition provided herein comprises tomatidine. In some embodiments, the SHH signaling pathway inhibitor in the methods and composition provided herein comprises AY9944. In some embodiments, the SHH signaling pathway inhibitor in the methods and composition provided herein comprises triparanol. In some embodiments, the SHH signaling pathway inhibitor in the methods and composition provided herein comprises compound A or compound B (as disclosed in U.S. Pub. No. 2004/0060568). In some embodiments, the SHH signaling pathway inhibitor in the methods and composition provided herein comprises a steroidal alkaloid that antagonizes hedgehog signaling (e.g., cyclopamine or a derivative thereof) as disclosed in U.S. Pub. No. 2006/0276391. In certain embodiments, the methods, compositions, and kits disclosed herein exclude a SHH signaling pathway inhibitor.

Retinoic Acid Signaling Pathway

Aspects of the disclosure relate to the use of modulators of retinoic acid signaling as β cell differentiation factors.

In some embodiments, the modulator of retinoic acid signaling in the methods and composition provided herein comprises an activator of retinoic acid signaling. In some embodiments, the RA signaling pathway activator in the methods and composition provided herein comprises retinoic acid. In some embodiments, the RA signaling pathway activator in the methods and composition provided herein comprises a retinoic acid receptor agonist. Exemplary retinoic acid receptor agonists in the methods and composition provided herein include, without limitation, CD 1530, AM 580, TTNPB, CD 437, Ch 55, BMS 961, AC 261066, AC 55649, AM 80, BMS 753, tazarotene, adapalene, and CD 2314.

In some embodiments, the modulator of retinoic acid signaling in the methods and composition provided herein comprises an inhibitor of retinoic acid signaling. In some embodiments, the retinoic acid signaling pathway inhibitor comprises DEAB (IUPAC Name: 2-[2-(diethylamino)ethoxy]-β-prop-2-enylbenzaldehyde). In some embodiments, the retinoic acid signaling pathway inhibitor comprises an analog or derivative of DEAB.

In some embodiments, the retinoic acid signaling pathway inhibitor in the methods and composition provided herein comprises a retinoic acid receptor antagonist. In some embodiments, the retinoic acid receptor antagonist in the methods and composition provided herein comprises (E)-4-[2-(5,6-dihydro-5,5-dimethyl-8-phenyl-2-naphthalenyl)ethenyl]benzoic acid, (E)-4-[[(5,6-dihydro-5,5-dimethyl-8-phenylethynyl)-2-naphthalenyl]ethenyl]benzoic acid, (E)-4-[2-[5,6-dihydro-5,5-dimethyl-8-(2-naphthalenyl)-2-naphthalenyl]ethenyl]-benzoic acid, and (E)-4-[2-[5,6-dihydro-5,5-dimethyl-8-(4-methoxyphenyl)-2-naphthalenyl]ethenyl]benzoic acid. In some embodiments, the retinoic acid receptor antagonist comprises BMS 195614 (CAS #253310-42-8), ER 50891 (CAS #187400-85-7), BMS 493 (CAS #170355-78-9), CD 2665 (CAS #170355-78-9), LE 135 (CAS #155877-83-1), BMS 453 (CAS #166977-43-1), or MM 11253 (CAS #345952-44-5).

In certain embodiments, the methods, compositions, and kits disclosed herein exclude a modulator of retinoic acid signaling. In certain embodiments, the methods, compositions, and kits disclosed herein exclude a retinoic acid signaling pathway activator. In certain embodiments, the methods, compositions, and kits disclosed herein exclude a retinoic acid signaling pathway inhibitor.

Protein Kinase C

Aspects of the disclosure relate to the use of protein kinase C activators as β cell differentiation factors. Protein kinase C is one of the largest families of protein kinase enzymes and is composed of a variety of isoforms. Conventional isoforms include α, βI, βII, γ; novel isoforms include δ, ε, η, Θ; and atypical isoforms include ξ, and ι/λ. PKC enzymes are primarily cytosolic but translocate to the membrane when activated. In the cytoplasm, PKC is phosphorylated by other kinases or autophosphorylates. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all. PKC activators that bind to the DAG site include, but are not limited to, bryostatin, picologues, phorbol esters, aplysiatoxin, and gnidimacrin. PKC activators that bind to the PS site include, but are not limited to, polyunsaturated fatty acids and their derivatives. It is contemplated that any protein kinase C activator that is capable, either alone or in combination with one or more other β cell differentiation factors, of inducing the differentiation of at least one insulin-producing, endocrine cell or precursor thereof into a SC-β cell can be used in the methods, compositions, and kits described herein.

In some embodiments, the PKC activator in the methods and composition provided herein comprises PdbU. In some embodiments, the PKC activator in the methods and composition provided herein comprises TPB. In some embodiments, the PKC activator in the methods and composition provided herein comprises cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, and growth factor activators, as described in WIPO Pub. No. WO/2013/071282. In some embodiments, the bryostain comprises bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In certain embodiments, the methods, compositions, and kits disclosed herein exclude a protein kinase C activator.

Y-Secretase Inhibitors

Aspects of the disclosure relate to the use of γ-secretase inhibitors as β cell differentiation factors.

In some embodiments, the γ-secretase inhibitor in the methods and composition provided herein comprises XXI. In some embodiments, the γ-secretase inhibitor in the methods and composition provided herein comprises DAPT. Additional exemplary γ-secretase inhibitors in the methods and composition provided herein include, without limitation, the γ-secretase inhibitors described in U.S. Pat. Nos. 7,049,296, 8,481,499, 8,501,813, and WIPO Pub. No. WO/2013/052700. In certain embodiments, the methods, compositions, and kits disclosed herein exclude a γ-secretase inhibitor.

Thyroid Hormone Signaling Pathway Activators

Aspects of the disclosure relate to the use of thyroid hormone signaling pathway activators as β cell differentiation factors.

In some embodiments, the thyroid hormone signaling pathway activator in the methods and composition provided herein comprises triiodothyronine (T3). In some embodiments, the thyroid hormone signaling pathway activator in the methods and composition provided herein comprises an analog or derivative of T3. Exemplary analogs of T3 in the methods and composition provided herein include, but are not limited to, selective and non-selective thyromimetics, TRO selective agonist-GC-1, GC-24,4-Hydroxy-PCB 106, MB07811, MB07344,3,5-diiodothyropropionic acid (DITPA); the selective TR-β agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and β-iodothyronamine (T1AM) and thyronamine (TOAM) (via T4 and T3 deiodination and amino acid decarboxylation), as well as for TH structural analogs, such as 3,5,3'-triiodothyropropionic acid (Triprop), 3,5-dibromo-β-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy] acetic acid (GC-1), 3,5-dichloro-4-[(4-hydroxy-β-isopropylphenoxy)phenyl]acetic acid (KB-141), and 3,5-diiodothyropropionic acid (DITPA).

In some embodiments, the thyroid hormone signaling pathway activator in the methods and composition provided herein comprises a prodrug or prohormone of T3, such as T4 thyroid hormone (e.g., thyroxine or L-3,5,3',5'-tetraiodothyronine).

In some embodiments, the thyroid hormone signaling pathway activator in the methods and composition provided herein is an iodothyronine composition described in U.S. Pat. No. 7,163,918.

Epidermal Growth Factor (EGF) Family

Aspects of the disclosure relate to the use of growth factors from the EGF family as β cell differentiation factors.

In some embodiments, the at least one growth factor from the EGF family in the methods and composition provided herein comprises betacellulin. In some embodiments, at least one growth factor from the EGF family in the methods and composition provided herein comprises EGF. Epidermal growth factor (EGF) is a 53 amino acid cytokine which is proteolytically cleaved from a large integral membrane protein precursor. In some embodiments, the growth factor from the EGF family in the methods and composition provided herein comprises a variant EGF polypeptide, for example an isolated epidermal growth factor polypeptide having at least 90% amino acid identity to the human wild-type EGF polypeptide sequence, as disclosed in U.S. Pat. No. 7,084,246. In some embodiments, the growth factor from the EGF family in the methods and composition provided herein comprises an engineered EGF mutant that binds to and agonizes the EGF receptor, as is disclosed in U.S. Pat. No. 8,247,531. In some embodiments, the at least one growth factor from the EGF family in the methods and composition provided herein is replaced with an agent that activates a signaling pathway in the EGF family. In some embodiments, the growth factor from the EGF family in the methods and composition provided herein comprises a compound that mimics EGF. In certain embodiments, the methods, compositions, and kits disclosed herein exclude a growth factor from the EGF family.

Protein Kinase Inhibitors

Aspects of the disclosure relate to the use of protein kinase inhibitors as β cell differentiation factors.

In some embodiments, the protein kinase inhibitor in the methods and composition provided herein comprises staurosporine. In some embodiments, the protein kinase inhibitor in the methods and composition provided herein comprises an analog of staurosporine. Exemplary analogs of staurosporine in the methods and composition provided herein include, without limitation, Ro-31-8220, a bisindolylmaleimide (Bis) compound, 10'-{5"-[(methoxycarbonyl)amino]-2"-methyl}-phenylaminocarbonylstaurosporine, a staralog (see, e.g., Lopez et al., "Staurosporine-derived inhibitors broaden the scope of analog-sensitive kinase technology", *J. Am. Chem. Soc.* 2013; 135(48):18153-18159), and, cgp41251.

In some embodiments, the protein kinase inhibitor in the methods and composition provided herein is an inhibitor of PKCβ. In some embodiments, the protein kinase inhibitor in the methods and composition provided herein is an inhibitor of PKCβ with the following structure or a derivative, analogue or variant of the compound as follows:

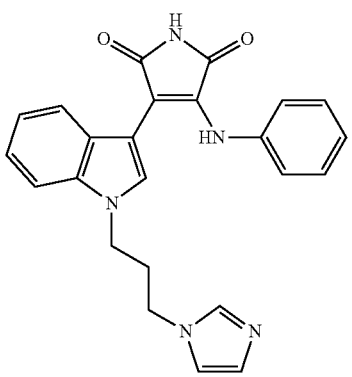 [SMILES: O=C1NC(=O)C(c2cn(CCCn3ccnc3)c3ccccc23)=C1Nc1ccccc1]

In some embodiments, the inhibitor of PKCβ is a GSK-2 compound with the following structure or a derivative, analogue or variant of the compound as follows:

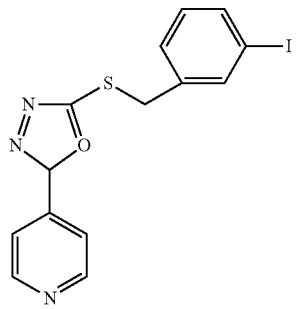

In some embodiments, the inhibitor of PKC in the methods and composition provided herein is a bisindolylmaleimide. Exemplary bisindolylmaleimides include, without limitation, bisindolylmaleimide I, bisindolylmaleimide II, bisindolylmaleimide III, hydrochloride, or a derivative, analogue or variant thereof.

In some embodiments, the PKC inhibitor in the methods and composition provided herein is a pseudohypericin, or a derivative, analogue, or variant thereof. In some embodiments, the PKC inhibitor in the methods and composition provided herein is indorublin-β-monoximc, 5-Iodo or a derivative, analogue or variant thereof. In certain embodiments, the methods, compositions, and kits disclosed herein exclude a protein kinase inhibitor.

VI. Pharmaceutical Compositions

In some cases, the present disclosure provides pharmaceutical compositions that can utilize non-native pancreatic β cell (beta cells) populations and cell components and products in various methods for treatment of a disease (e.g., diabetes). Certain cases encompass pharmaceutical compositions comprising live cells (e.g., non-native pancreatic β cells alone or admixed with other cell types). Other cases encompass pharmaceutical compositions comprising non-native pancreatic β cell components (e.g., cell lysates, soluble cell fractions, conditioned medium, ECM, or components of any of the foregoing) or products (e.g., trophic and other biological factors produced by non-native pancreatic β cells or through genetic modification, conditioned medium from non-native pancreatic β cell culture). In either case, the pharmaceutical composition may further comprise other active agents, such as anti-inflammatory agents, exogenous small molecule agonists, exogenous small molecule antagonists, anti-apoptotic agents, antioxidants, and/or growth factors known to a person having skill in the art.

Pharmaceutical compositions of the present disclosure can comprise non-native pancreatic β cell, or components or products thereof, formulated with a pharmaceutically acceptable carrier (e.g. a medium or an excipient). The term pharmaceutically acceptable carrier (or medium), which may be used interchangeably with the term biologically compatible carrier or medium, can refer to reagents, cells, compounds, materials, compositions, and/or dosage forms that are not only compatible with the cells and other agents to be administered therapeutically, but also are suitable for use in contact with the tissues of human beings and animals without excessive toxicity, irritation, allergic response, or other complication. Suitable pharmaceutically acceptable carriers can include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical compositions comprising cellular components or products, but not live cells, can be formulated as liquids. Pharmaceutical compositions comprising living non-native pancreatic β cells can be formulated as liquids, semisolids (e.g., gels, gel capsules, or liposomes) or solids (e.g., matrices, scaffolds and the like).

As used here, the term "pharmaceutically acceptable" can refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" can refer to a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL;

(22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

The phrase "therapeutically-effective amount" as used herein in respect to a population of cells means that amount of relevant cells in a population of cells, e.g., SC-β cells or mature pancreatic β cells, or composition comprising SC-β cells of the present disclosure which is effective for producing some desired therapeutic effect in at least a sub-population of cells in an animal at a reasonable benefit/risk ratio applicable to any medical treatment. For example, an amount of a population of SC-β cells administered to a subject that is sufficient to produce a statistically significant, measurable change in at least one symptom of Type 1, Type 1.5 or Type 2 diabetes, such as glycosylated hemoglobin level, fasting blood glucose level, hypoinsulinemia, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

Pharmaceutical compositions can comprise auxiliary components as would be familiar to a person having skill in the art. For example, they can contain antioxidants in ranges that vary depending on the kind of antioxidant used. Reasonable ranges for commonly used antioxidants are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. Other representative compounds include mercaptopropionyl glycine, N-acetyl cysteine, β-mercaptoethylamine, glutathione and similar species, although other anti-oxidant agents suitable for renal administration, e.g. ascorbic acid and its salts or sulfite or sodium metabisulfite may also be employed.

A buffering agent can be used to maintain the pH of formulations in the range of about 4.0 to about 8.0; so as to minimize irritation in the target tissue. For direct intraperitoneal injection, formulations should be at pH 7.2 to 7.5, preferably at pH 7.35-7.45. The compositions may also include tonicity agents suitable for administration to the kidney. Among those suitable is sodium chloride to make formulations approximately isotonic with blood.

In certain cases, pharmaceutical compositions are formulated with viscosity enhancing agents. Exemplary agents are hydroxyethylcellulose, hydroxypropylcellulose, methylcellulose, and polyvinylpyrrolidone. The pharmaceutical compositions may have cosolvents added if needed. Suitable cosolvents may include glycerin, polyethylene glycol (PEG), polysorbate, propylene glycol, and polyvinyl alcohol. Preservatives may also be included, e.g., benzalkonium chloride, benzethonium chloride, chlorobutanol, phenylmercuric acetate or nitrate, thimerosal, or methyl or propylparabens.

Pharmaceutical compositions comprising cells, cell components or cell products may be delivered to the kidney of a patient in one or more of several methods of delivery known in the art. In some cases, the compositions are delivered to the kidney (e.g., on the renal capsule and/or underneath the renal capsule). In another embodiment, the compositions may be delivered to various locations within the kidney via periodic intraperitoneal or intrarenal injection. Alternatively, the compositions may be applied in other dosage forms known to those skilled in the art, such as pre-formed or in situ-formed gels or liposomes.

Pharmaceutical compositions comprising live cells in a semi-solid or solid carrier are may be formulated for surgical implantation on or beneath the renal capsule. It should be appreciated that liquid compositions also may be administered by surgical procedures. In particular cases, semi-solid or solid pharmaceutical compositions may comprise semi-permeable gels, lattices, cellular scaffolds and the like, which may be non-biodegradable or biodegradable. For example, in certain cases, it may be desirable or appropriate to sequester the exogenous cells from their surroundings, yet enable the cells to secrete and deliver biological molecules (e.g., insulin) to surrounding cells or the blood stream. In these cases, cells may be formulated as autonomous implants comprising living non-native pancreatic β cells or cell population comprising non-native pancreatic β cell surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression.

In other cases, various degradable gels and networks can be used for the pharmaceutical compositions of the present disclosure. For example, degradable materials particularly suitable for sustained release formulations include biocompatible polymers, such as poly(lactic acid), poly (lactic-co-glycolic acid), methylcellulose, hyaluronic acid, collagen, and the like.

In other cases, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established.

Examples of scaffold or matrix (sometimes referred to collectively as "framework") material that may be used in the present disclosure include nonwoven mats, porous foams, or self-assembling peptides. Nonwoven mats, for example, may be formed using fibers comprising a synthetic absorbable copolymer of glycolic and lactic acids (PGA/PLA), foams, and/or poly(epsilon-caprolactone)/poly(glycolic acid) (PCL/PGA) copolymer.

In another embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures. In many of the abovementioned cases, the framework may be molded into a useful shape. Furthermore, it will be appreciated that non-native pancreatic β cells may be cultured on pre-formed, non-degradable surgical or implantable devices.

The matrix, scaffold or device may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In one aspect, the present disclosure provided devices comprising a cell cluster comprising at least one pancreatic β cell. A device provided herein can be configured to produce and release insulin when implanted into a subject. A device can comprise a cell cluster comprising at least one pancreatic β cell, e.g., a non-native pancreatic β cell. A cell cluster in the device can exhibit in vitro GSIS. A device can further comprise a semipermeable membrane. The semipermeable membrane can be configured to retain the cell cluster in the device and permit passage of insulin secreted by the cell cluster. In some cases of the device, the cell cluster can be encapsulated by the semipermeable membrane. The encapsulation can be performed by any technique available to one skilled in the art. The semipermeable membrane can also be made of any suitable material as one skilled in the art would appreciate and verify. For example, the semipermeable membrane can be made of polysaccharide or polycation. In some cases, the semipermeable membrane can be made of poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, poly-ortho esters, polyacetals, polycyanoacrylates, biodegradable polyurethanes, albumin, collagen, fibrin, polyamino acids, prolamines, alginate, agarose, agarose with gelatin, dextran, polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, polyethylene oxide, or any combinations thereof. In some cases, the semipermeable membrane comprises alginate. In some cases, the cell cluster is encapsulated in a microcapsule that comprises an alginate core surrounded by the semipermeable membrane. In some cases, the alginate core is modified, for example, to produce a scaffold comprising an alginate core having covalently conjugated oligopeptides with an RGD sequence (arginine, glycine, aspartic acid). In some cases, the alginate core is modified, for example, to produce a covalently reinforced microcapsule having a chemoenzymatically engineered alginate of enhanced stability. In some cases, the alginate core is modified, for example, to produce membrane-mimetic films assembled by in-situ polymerization of acrylate functionalized phospholipids. In some cases, microcapsules are composed of enzymatically modified alginates using epimerases, In some cases, microcapsules comprise covalent links between adjacent layers of the microcapsule membrane. In some embodiment, the microcapsule comprises a subsieve-size capsule comprising alginate coupled with phenol moieties. In some cases, the microcapsule comprises a scaffold comprising alginate-agarose. In some cases, the SC-β cell is modified with PEG before being encapsulated within alginate. In some cases, the isolated populations of cells, e.g., SC-β cells are encapsulated in photoreactive liposomes and alginate. It should be appreciated that the alginate employed in the microcapsules can be replaced with other suitable biomaterials, including, without limitation, polyethylene glycol (PEG), chitosan, polyester hollow fibers, collagen, hyaluronic acid, dextran with ROD, BHD and polyethylene glycol-diacrylate (PEGDA), poly(MPC-co-n-butyl methacrylate-co-4-vinylphenyl boronic acid) (PMBV) and poly (vinyl alcohol) (PVA), agarose, agarose with gelatin, and multilayer cases of these. In some cases, the device provided herein comprise extracorporeal segment, e.g., part of the device can be outside a subject's body when the device is implanted in the subject. The extracorporeal segment can comprise any functional component of the device, with or without the cells or cell cluster provided herein.

VII. Methods of Treating

Further provided herein are methods for treating or preventing a disease in a subject. A composition comprising the cell clusters or cells provided herein or generated according to the methods provided herein can be administered into a subject to restore a degree of pancreatic function in the subject. For example, the cell clusters resembling endogenous pancreatic islets, or the cells resembling endogenous pancreatic β cells (e.g., non-native pancreatic β cells or SC-β cells) or the precursors thereof can be transplanted to a subject to treat diabetes.

The methods can comprise transplanting the cell cluster or the cell disclosed in the application to a subject, e.g., a subject in need thereof. The term "transplanting" can refer to the placement of cells or cell clusters, any portion of the cells or cell clusters thereof, or any compositions comprising cells, cell clusters or any portion thereof, into a subject, by a method or route which results in at least partial localization of the introduced cells or cell clusters at a desired site. The cells or cell clusters can be implanted directly to the pancreas, or alternatively be administered by any appropriate route which results in delivery to a desired location in the subject where at least a portion of the implanted cells or cell remain viable. The period of viability of the cells or cell clusters after administration to a subject can be as short as a few hours, e.g. twenty-four hours, to a few days, to as long as several years. In some instances, the cells or cell clusters, or any portion of the cells or cell clusters thereof, can also be transadministered at a non-pancreatic location, such as in the liver or subcutaneously, for example, in a capsule (e.g., microcapsule) to maintain the implanted cells or cell clusters at the implant location and avoid migration.

As used herein, the term "treating" and "treatment" can refer to administering to a subject an effective amount of a composition (e.g., cell clusters or a portion thereof) so that the subject as a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (e.g., partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment," "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Delaying the onset of diabetes in a subject refers to delay of onset of at least one symptom of diabetes, e.g., hyperglycemia, hypoinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

In some aspects, the disclosure relates to a method comprising implanting in a subject a device comprising a cell or cell cluster provided herein (e.g., insulin producing cells), wherein the device releases insulin in an amount sufficient for a reduction of blood glucose levels in the subject. In some embodiments, the insulin producing cells are glucose responsive insulin producing cells.

In some embodiments, the reduction of blood glucose levels in the subject, as induced by the transplantation of the cell or cell cluster, or the device provided herein, results in an amount of glucose which is lower than the diabetes threshold. In some embodiments, the subject is a mammalian subject. In some embodiments, the mammalian subject is human. In some embodiments, the amount of glucose is reduced to lower than the diabetes threshold in 1, 2, 3, 4, 5, 6, 7, 8, 9, or 10 days after the implanting.

As described in detail above, the pharmaceutical compositions of the present disclosure can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

A subject that can be treated by the methods herein can be a human or a non-human animal. In some cases, a subject can be a mammal. Examples of a subject include but are not limited to primates, e.g., a monkey, a chimpanzee, a bamboo, or a human. In some cases, a subject is a human. A subject can be non-primate animals, including, but not limited to, a dog, a cat, a horse, a cow, a pig, a sheep, a goat, a rabbit, and the like. In some cases, a subject receiving the treatment is a subject in need thereof, e.g., a human in need thereof.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used as subjects that represent animal models of Type 1 diabetes, Type 2 Diabetes Mellitus, or pre-diabetic conditions. In addition, the methods described herein can be used to treat domesticated animals and/or pets. A subject can be male or female. A subject can be one who has been previously diagnosed with or identified as suffering from or having Diabetes (e.g., Type 1 or Type 2), one or more complications related to Diabetes, or a pre-diabetic condition, and optionally, but need not have already undergone treatment for the Diabetes, the one or more complications related to Diabetes, or the pre-diabetic condition. A subject can also be one who is not suffering from Diabetes or a pre-diabetic condition. A subject can also be one who has been diagnosed with or identified as suffering from Diabetes, one or more complications related to Diabetes, or a pre-diabetic condition, but who show improvements in known Diabetes risk factors as a result of receiving one or more treatments for Diabetes, one or more complications related to Diabetes, or the pre-diabetic condition. Alternatively, a subject can also be one who has not been previously diagnosed as having Diabetes, one or more complications related to Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to Diabetes or a pre-diabetic condition as defined herein, or alternatively, a subject can be one who has not been previously diagnosed with or identified as having one or more complications related to Diabetes or a pre-diabetic condition.

The methods can comprise transplanting the cell cluster to a subject using any means in the art. For example the methods can comprise transplanting the cell cluster via the intraperitoneal space, renal subcapsule, renal capsule, omentum, subcutaneous space, or via pancreatic bed infusion. For example, transplanting can be subcapsular transplanting, intramuscular transplanting, or intraportal transplanting, e.g., intraportal infusion. Immunoprotective encapsulation can be implemented to provide immunoprotection to the cell clusters. In some cases, the methods of treatment provided herein can comprise administer immune response modulator for modulating or reducing transplant rejection response or other immune response against the implant (e.g., the cells or the device). Examples of immune response modulator that can be used in the methods can include purine synthesis inhibitors like Azathioprine and Mycophenolic acid, pyrimidine synthesis inhibitors like Leflunomide and Teriflunomide, antifolate like Methotrexate, Tacrolimus, Ciclosporin, Pimecrolimus, Abetimus, Gusperimus, Lenalidomide, Pomalidomide, Thalidomide, PDE4 inhibitor, Apremilast, Anakinra, Sirolimus, Everolimus, Ridaforolimus, Temsirolimus, Umirolimus, Zotarolimus, Anti-thymocyte globulin antibodies, Anti-lymphocyte globulin antibodies, CTLA-4, fragment thereof, and fusion proteins thereof like Abatacept and Belatacept, TNF inhibitor like Etanercept and Pegsunercept, Aflibercept, Alefacept, Rilonacept, antibodies against complement component 5 like Eculizumab, anti-TNF antibodies like Adalimumab, Afelimomab, Certolizumab pegol, Golimumab, Infliximab, and Nerelimomab, antibodies against Interleukin 5 like Mepolizumab, anti-Ig E antibodies like Omalizumab, anti-Interferon antibodies like Faralimomab, anti-IL-6 antibodies like Elsilimomab, antibodies against IL-12 and IL-23 like Lebrikizumab and Ustekinumab, anti-IL-17A antibodies like Secukinumab, anti-CD3 antibodies like Muromonab-CD3, Otelixizumab, Teplizumab, and Visilizumab, anti-CD4 antibodies like Clenoliximab, Keliximab, and Zanolimumab, anti-CD11a antibodies like Efalizumab, anti-CD18 antibodies like Erlizumab, anti-CD20 antibodies like Obinutuzumab, Rituximab, Ocrelizumab and Pascolizumab, anti-CD23 antibodies like Gomiliximab and Lumiliximab, anti-CD40 antibodies like Teneliximab and Toralizumab, antibodies against CD62 L/L-selectin like Aselizumab, anti-CD80 antibodies like Galiximab, anti-CD147/Basigin antibodies like Gavilimomab, anti-CD154 antibodies like Ruplizumab, anti-BLyS antibodies like Belimumab and Blisibimod, anti-CTLA-4 antibodies like Ipilimumab and Tremelimumab, anti-CAT antibodies like Bertilimumab, Lerdelimumab, and Metelimumab, anti-Integrin antibodies like Natalizumab, antibodies against Interleukin-6 receptor like Tocilizumab, anti-LFA-1 antibodies like Odulimomab, antibodies against IL-2 receptor/CD25 like Basiliximab, Daclizumab, and Inolimomab, antibodies against T-lymphocyte (Zolimomab aritox) like Atorolimumab, Cedelizumab, Fontolizumab, Maslimomab, Morolimumab, Pexelizumab, Reslizumab, Rovelizumab, Siplizumab, Talizumab, Telimomab aritox, Vapaliximab, and Vepalimomab.

EXAMPLES

These examples are provided for illustrative purposes only and not to limit the scope of the claims provided herein.

Example 1—Selection of Cell Lines for SC-β Cell Production

Embryonic stem cell (ESC) cell lines can be used for SC-β cell production.

Criteria for the ESC cell line selection can include consistent expansion in 2D culture system, adaptation to 3D culture, differentiation capacity, and function in vitro and in vivo. Example cell lines are shown in FIG. 1.

Example 2-2D Culture Criteria for ESC Cell Line

Figures 2A, 2B:
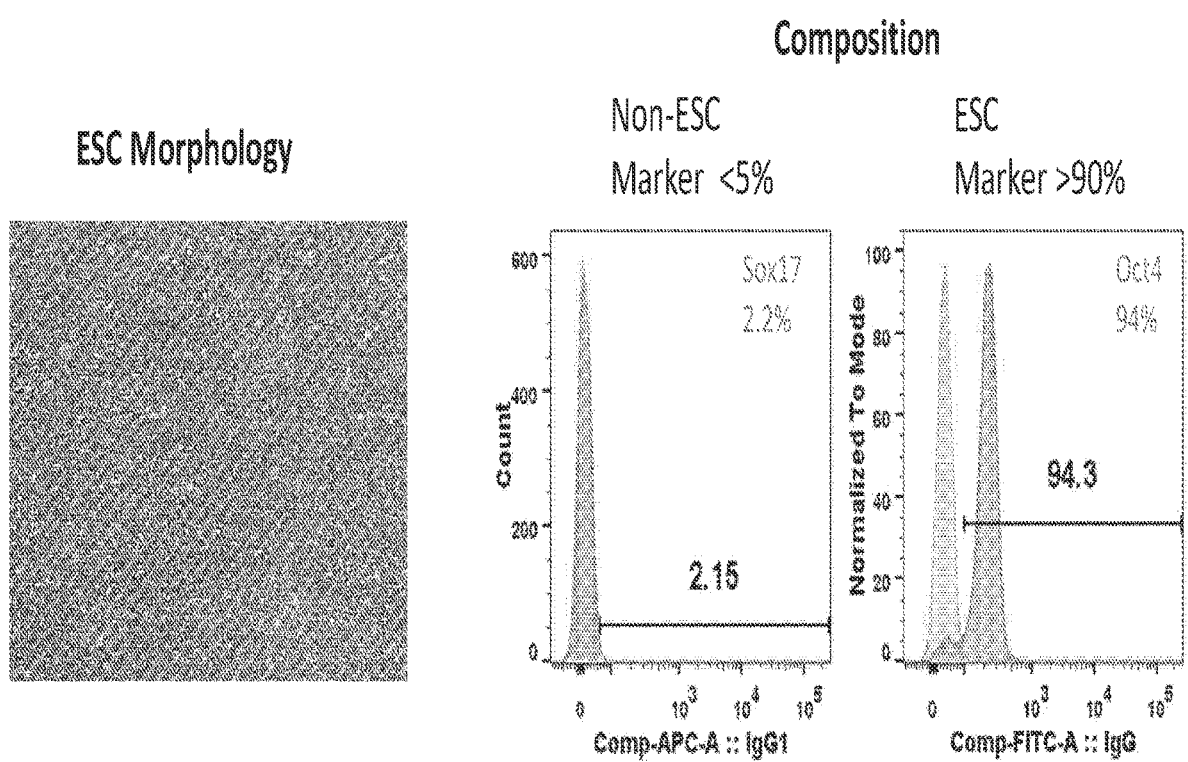
FIG. 2A depicts morphology of an exemplary 2D culture of embryonic stem cells (ESCs).
FIG. 2B depicts percentage of ESCs expressing cell surface marker Sox17 or Oct4 of an exemplary 2D culture.

Examples of selected ESC cell line morphology and composition are shown in FIGS. 2A and 2B. In this example, cells expressing non-ESC cell marker Sox17 and ESC-marker Oct4 were detected by flow cytometry. More than 90% of ESC cells were detected in the cell population.

Example 3—Differentiation Protocol of ESC Cell Line

Figure 3A:
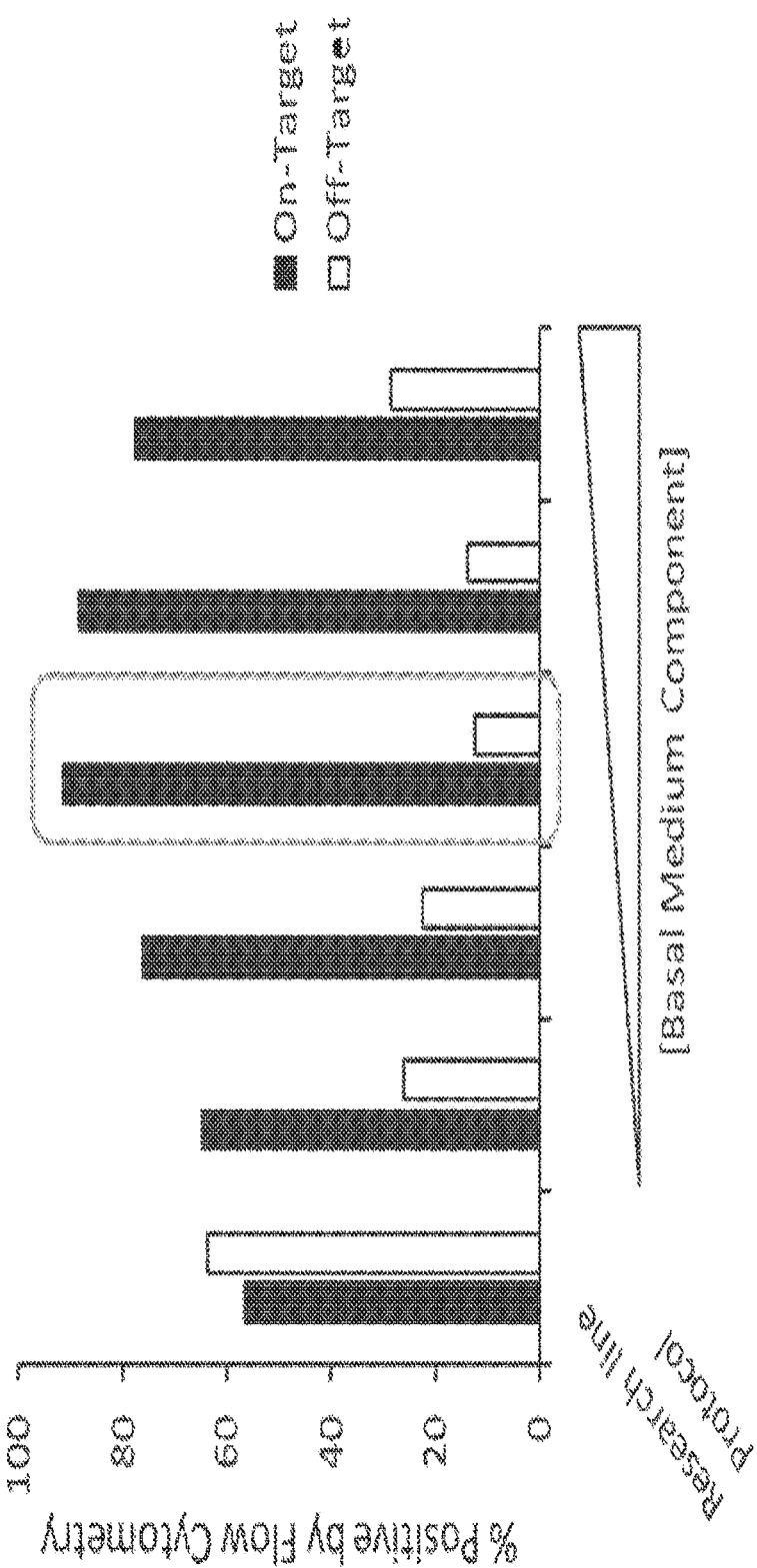
FIGS. 3A and 3B depict examples flow cytometry data for on-target and off-target progenitor populations.
Figure 3B:
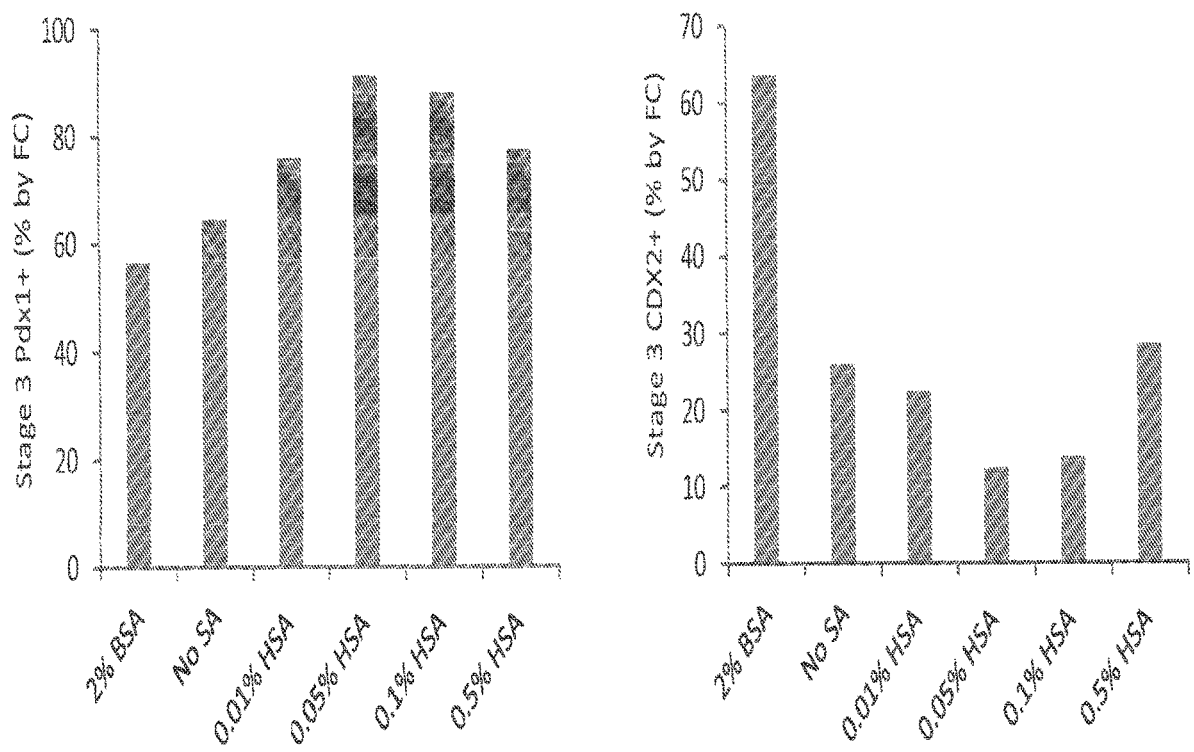

This example shows that exemplary basal culture medium according to the present disclosure can have improve differentiation efficiency as qualified by on-target and off-target progenitor populations. As shown in FIG. 3A, basal medium containing an exemplary component can increase percentage of on-target cells while decrease percentage of off-target cells. FIG. 3B shows that an exemplary component of the basal culture medium, human serum albumin (HSA), significantly increased the percentage of Pdx1-positive cells (Pdx1+) at the end of stage 3, as compared to differentiating the cells in culture medium containing bovine serum albumin (BSA) instead or culture medium having no serum albumin ("No SA"), when cells are differentiated following an exemplary differentiation protocol according to the present disclosure. At the same time, the presence of HSA significantly decreased the percentage of off-target CDX2-positive (CDX2+) cells at the end of stage 3, as compared to cells differentiated in culture medium containing BSA or No SA. The data also demonstrated a concentration-dependent effect of HSA on percentage of Pdx1+ and CDX2+ cells.

Another example as illustrated here demonstrated that an exemplary differentiation protocol according to the present disclosure (v10 protocol), which comprises differentiating primitive gut tube (PGT) cells into Pdx1-positive pancreatic progenitor cells (Stage 3) by incubating PGT cells in medium containing Activin A (20 ng/mL) and DMH-1 (0.25 μM), can significantly increase differentiation efficiency as determined by percentage of NKX6.1-positive, C-peptide-positive SC-β cells at the end of Stage 6 differentiation. As shown in FIGS. 4A and 4B, percentage of SC-β cells was increased by protocol v10 in comparison with other exemplary protocols without the incubation of both Activin A and DMH-1 at Stage 3 (v8 and v9). 1.5 to 2 fold increase of NKX6.1-positive, C-peptide-positive SC-β cells SC-β cell percentage was achieved by using protocol v10 as compared to another exemplary protocol. As shown in FIG. 4B, exemplary cell clusters generated by v10 protocol comprised more than 35% NKX6.1-positive, C-peptide-positive SC-β cells.

SC-β cells differentiated using the exemplary methods provided herein (exemplary protocols) resemble the natural pancreatic islet cells. As shown in image data in FIG. 5, SC-β cells had similar morphology as the natural islet cells. The images were produced by staining a β cell specific gene and insulin.

Example 4—Functional Analysis of Differentiated SC-β Cells

Signaling factors (e.g., exemplary differentiation factors disclosed herein, e.g., Activin A, DMH-1, LDN193189, or Alk5i) according to present disclosure can improve the in vitro function of SC-β cells generated using exemplary methods provided herein.

Figure 6A:
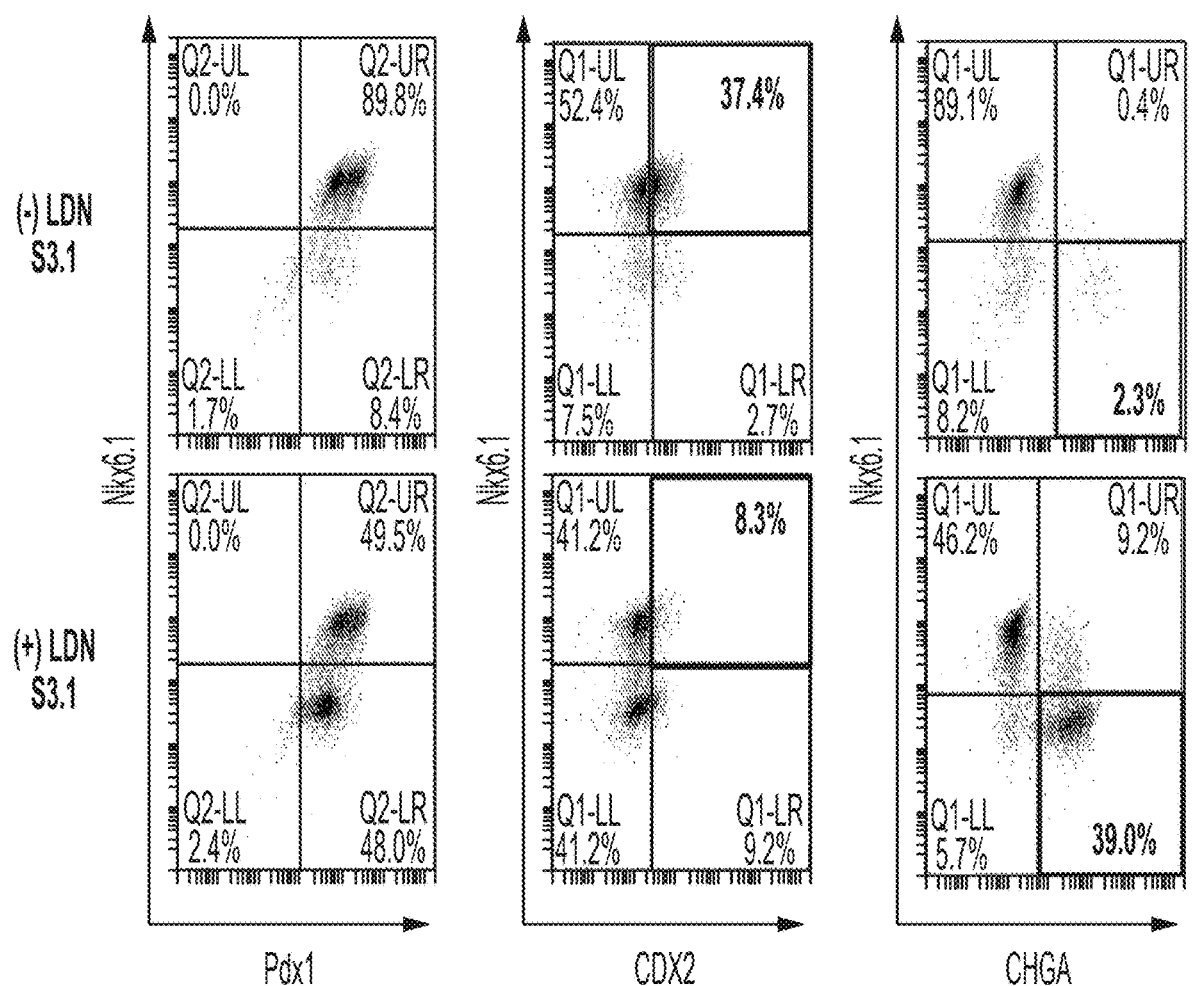
FIG. 6A depicts effects of exemplary differentiation factor (LDN) on Stage 4 cells differentiated using an exemplary method disclosed herein.

In one example, flow cytometry analysis showed that the presence or absence of LDN193189 at Stage 3 changed the cell constituent obtained at Stage 4-complete (e.g., at the completion of Stage 4 culture) according to one exemplary differentiation method provided herein. As shown in FIG. 6A, in this example, incubation of PGT cells (Stage 2 cells) with LDN193189 ("LDN" in the figure) clearly reduced the percentage of CDX2-positive cells in the cell population obtained at Stage 4-complete. In the meantime, LDN193189 also promoted chromogranin A (CHGA) expression in Stage 4-complete cells.

Figure 6B:
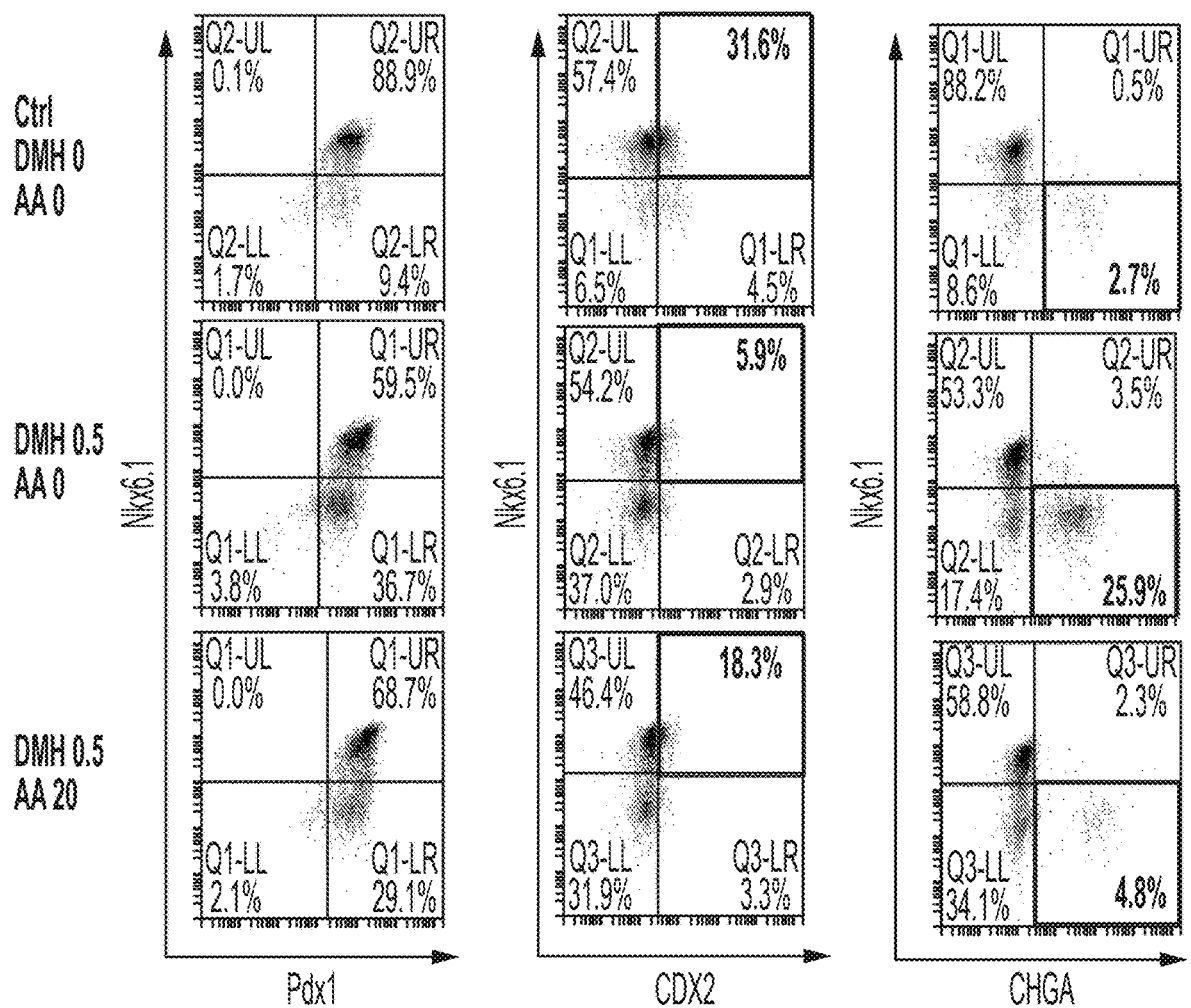
FIG. 6B depicts effects of exemplary differentiation factors (DMH-1 and Activin A) on Stage 4 cells differentiated using an exemplary method disclosed herein.

In another example, flow cytometry analysis showed that incubation of the cells comprising PGT cells (Stage 2 cells) with certain exemplary signaling factors (e.g., Activin A and DMH-1) affected the cell constituent obtained at Stage 4-complete (e.g., at the completion of Stage 4 culture) according to one exemplary differentiation method provided herein. As shown in FIG. 6B, in this example, incubation of 0.5 μM DMH-1 alone reduced the percentage of cells expressing CDX2 but increased the percentage of cells expressing CHGA as compared to no incubation of DMH-1, similar to the effect of LDN193189 in the other example as shown in FIG. 6A. However, co-incubation of 0.5 μM DMH-1 and 20 ng/mL Activin A ("AA" in the figure) reduced the percentage of CDX2-positive cells but also controlled the percentage of CHGA-positive cells under a low level as compared to the Stage 4-complete cells obtained without any DMH-1 or Activin A.

Figure 6C:
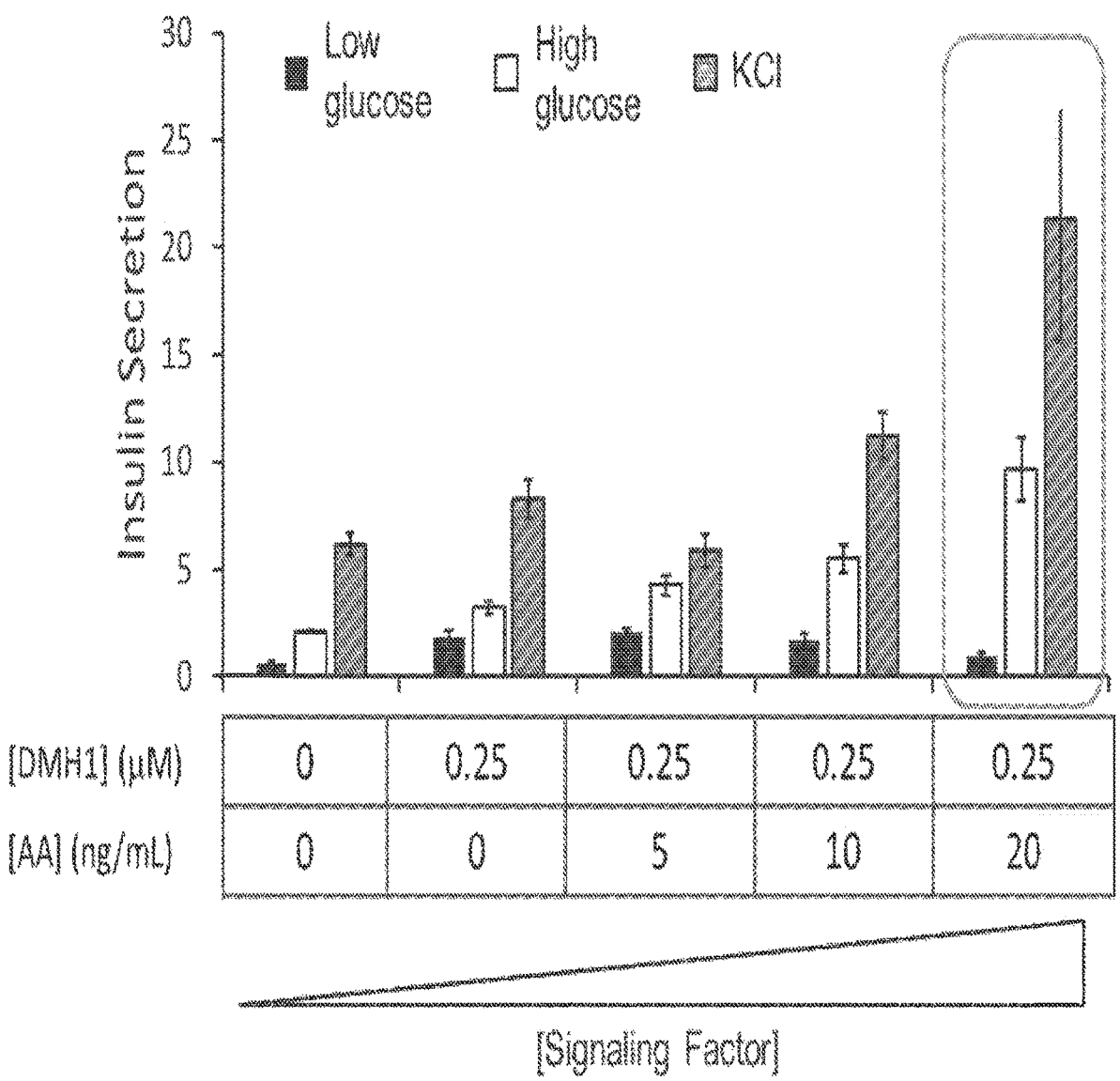
FIG. 6C depicts an example result of glucose stimulated insulin secretion (GSIS) assay using produced SC-β cells at increasing concentration of exemplary factors (DMH-1 and Activin A).
Figure 7:
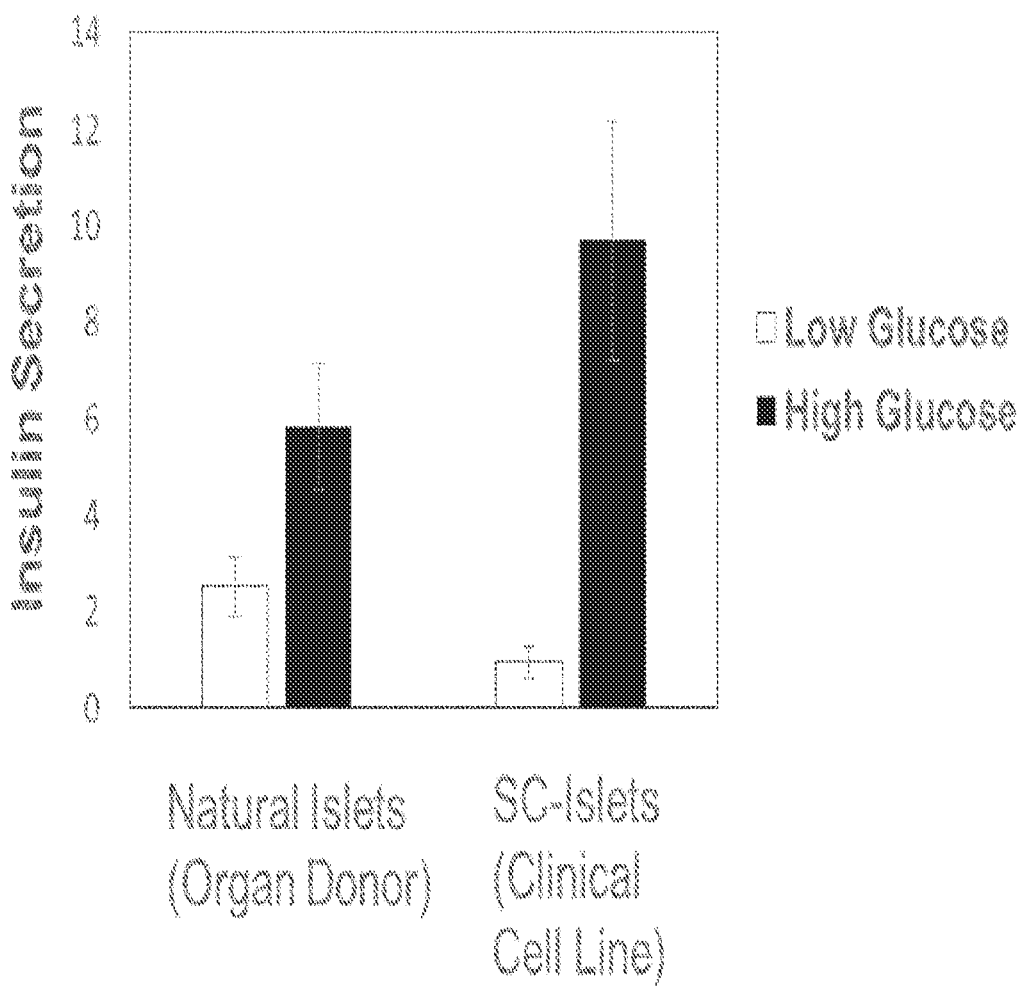
FIG. 7 depicts a comparison of insulin secretion of natural islet cells and exemplary SC-β cells at low or high glucose stimulation.
Figure 8:
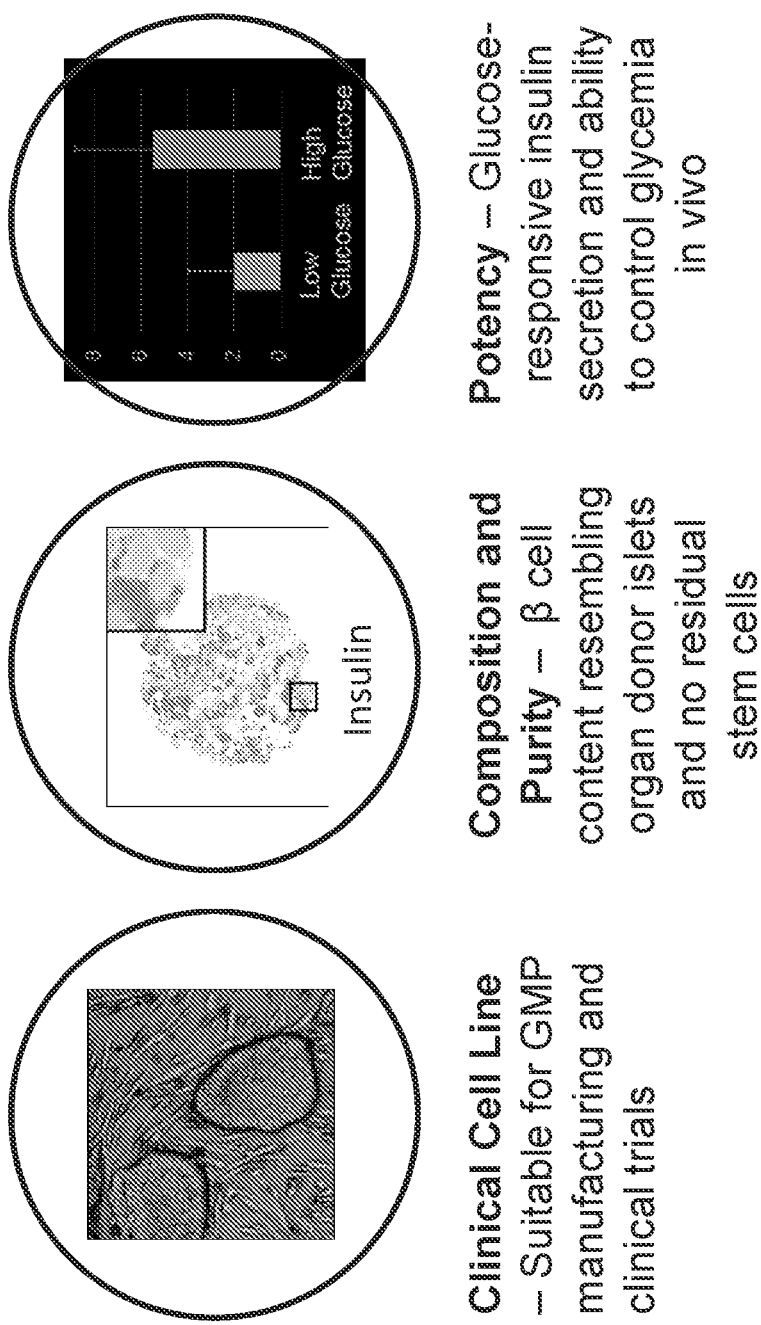
FIG. 8 depicts process development goals for SC-β cell product.

In another example, incubation of the cells comprising PGT cells (Stage 2 cells) with certain exemplary signaling factors (e.g., Activin A and DMH-1) significantly improved the insulin secretion of the cell population obtained at Stage 6 that comprises the SC-β cells. In vitro glucose-stimulated insulin secretion (GSIS) assay was used to quantify the function of SC-β cells in insulin secretion. As shown in FIG. 6C, addition of the exemplary signaling factors (DMH-1 and Activin A) at Stage 3 proved to improve the GSIS reactions in the presence of low glucose (2.8 mM), high glucose (20 mM), or KCl (30 mM KCl+2.8 mM glucose). As demonstrated by the figure, the exemplary signaling factors (Activin A and DMH-1) significantly increased the GSIS stimulation index as calculated by insulin secretion in response to high glucose stimulation divided by insulin secretion in response to low glucose stimulation. For instance, the stimulation index of Stage 6 cells obtained with the exemplary protocol using 20 ng/mL Activin A and 0.25 μM DMH-1 at Stage 3 was at least 3 times higher than the Stage 6 cells obtained with the exemplary protocol that does not use Activin A or DMH-1 at Stage 3. On the other hand, addition of Activin A and DMH-1 also significantly increased insulin secretion in response to KCl stimulation in a concentration-dependent manner. For example, the exemplary Stage 6 cells obtained with the exemplary protocol using 20 ng/mL Activin A and 0.25 μM DMH-1 at Stage 3 secreted at least 3 times higher insulin in response to KCl stimulation as compared to the Stage 6 cells obtained with the exemplary protocol using no Activin A or DMH-1 at Stage 3, while Stage 6 cells obtained with 10 ng/mL Activin A and 0.25 μM DMH-1 at Stage 3 secreted about 2 times higher insulin in response to the same KCl stimulation.

Example 5—Manufacturing of SC-β Cells in Large Scale

Production of SC-β cells was tested in large-scale cultures, for example, 0.1 L, 0.5 L, and 3 L cultures as shown in FIGS. 9A-9C. Fold expansion of cells was increased when the culture size was increased. The population of Oct4 expressing cells was qualified in each large-scale culture, and each of the large-scale cultures produced close to 100% Oct4 expressing cells.

Figure 10:
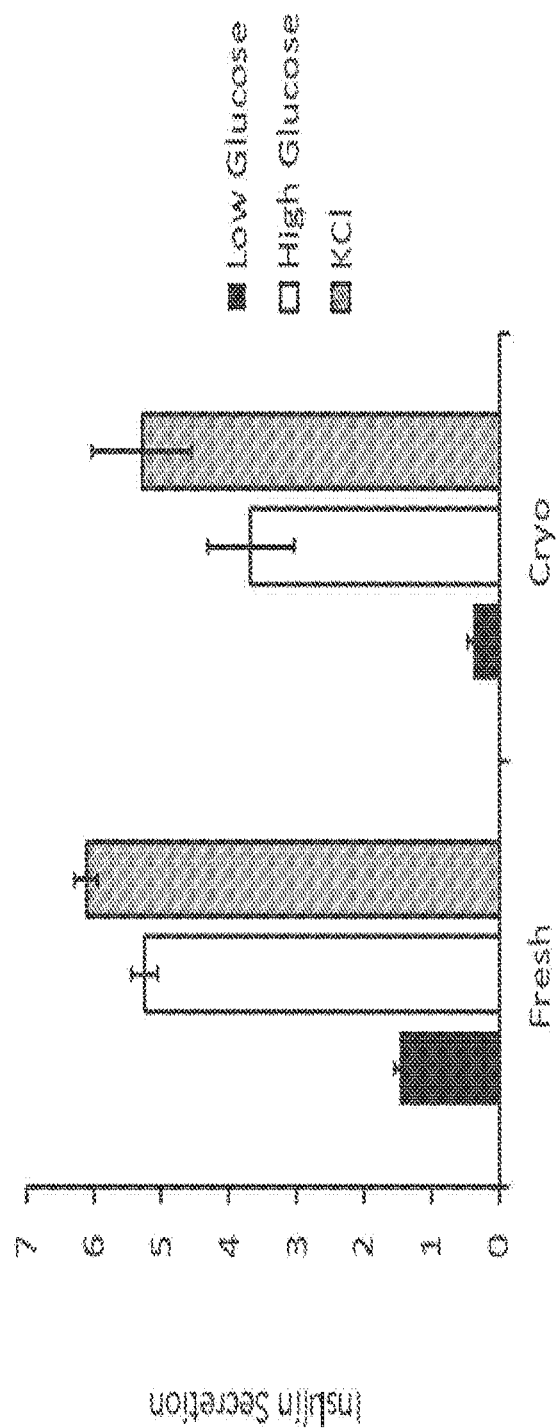
FIG. 10 depicts a comparison of insulin secretion of cryopreserved SC-β cells and fresh SC-β cells.

The produced SC-β cells still maintained the appropriate function (e.g. the ability to sense glucose and secrete insulin) after cryopreservation. As shown is FIG. 10, fresh SC-β cells and cryopreserved SC-β cells were compared in their ability to sense glucose and secrete insulin. Cryopreserved SC-β cells exhibited comparable activity.

Example 6—Treatment of Animal Models with SC-β Cells

Figure 11:
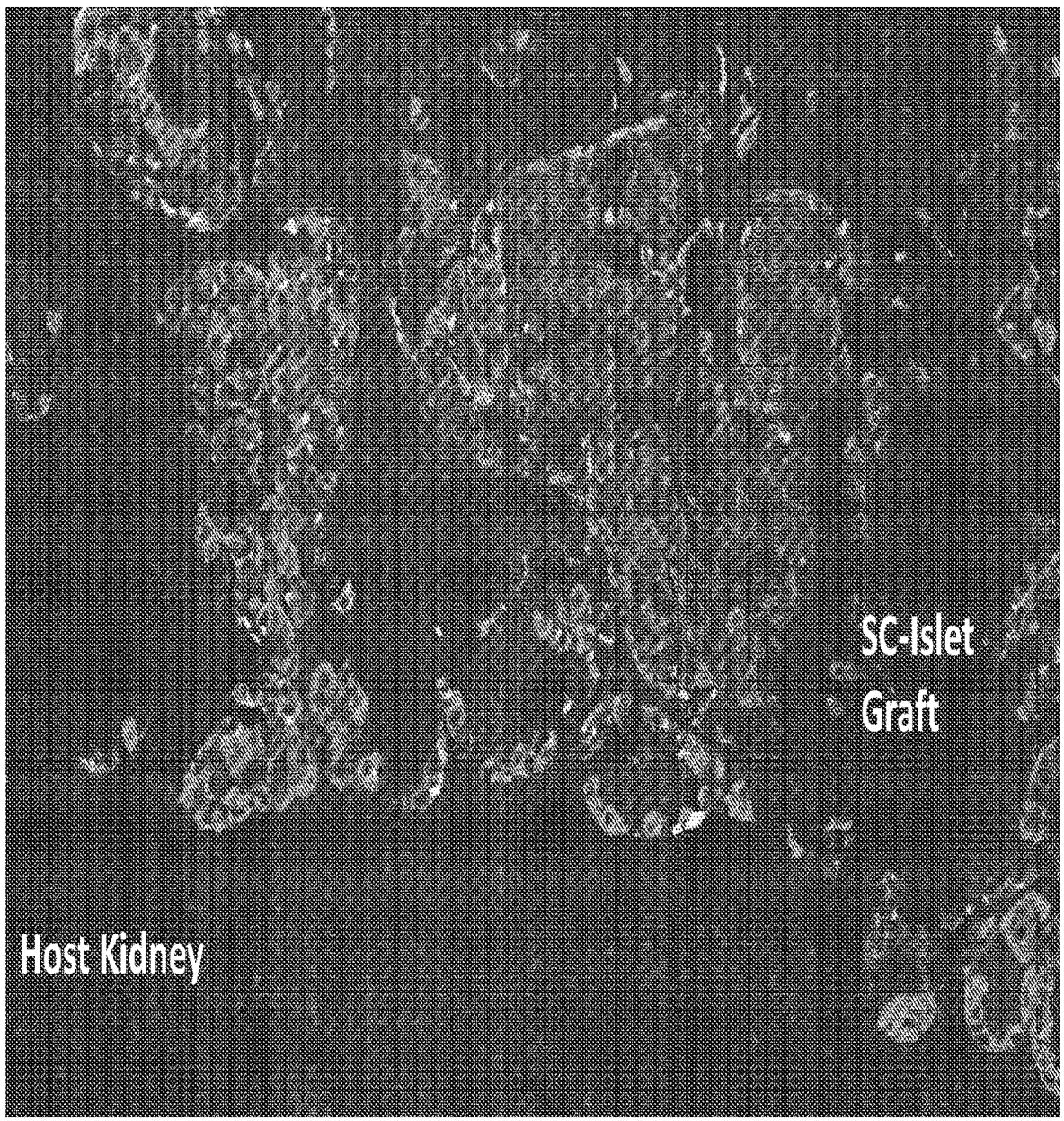
FIG. 11 depicts an image of transplanted SC-islet graft at 6 months.

SC-β cells were implanted into animal models, optionally by placing in a device, and implanting the device (e.g. diabetic immunodeficient mice). Tissue samples were obtained after 6 month of transplant. An example image of the tissue sample is shown in FIG. 11. Transplanted SC-β cell graft contained large numbers of a and β cells. Image was stained using C-peptide, glucagon, and DAPI.

Figure 12:
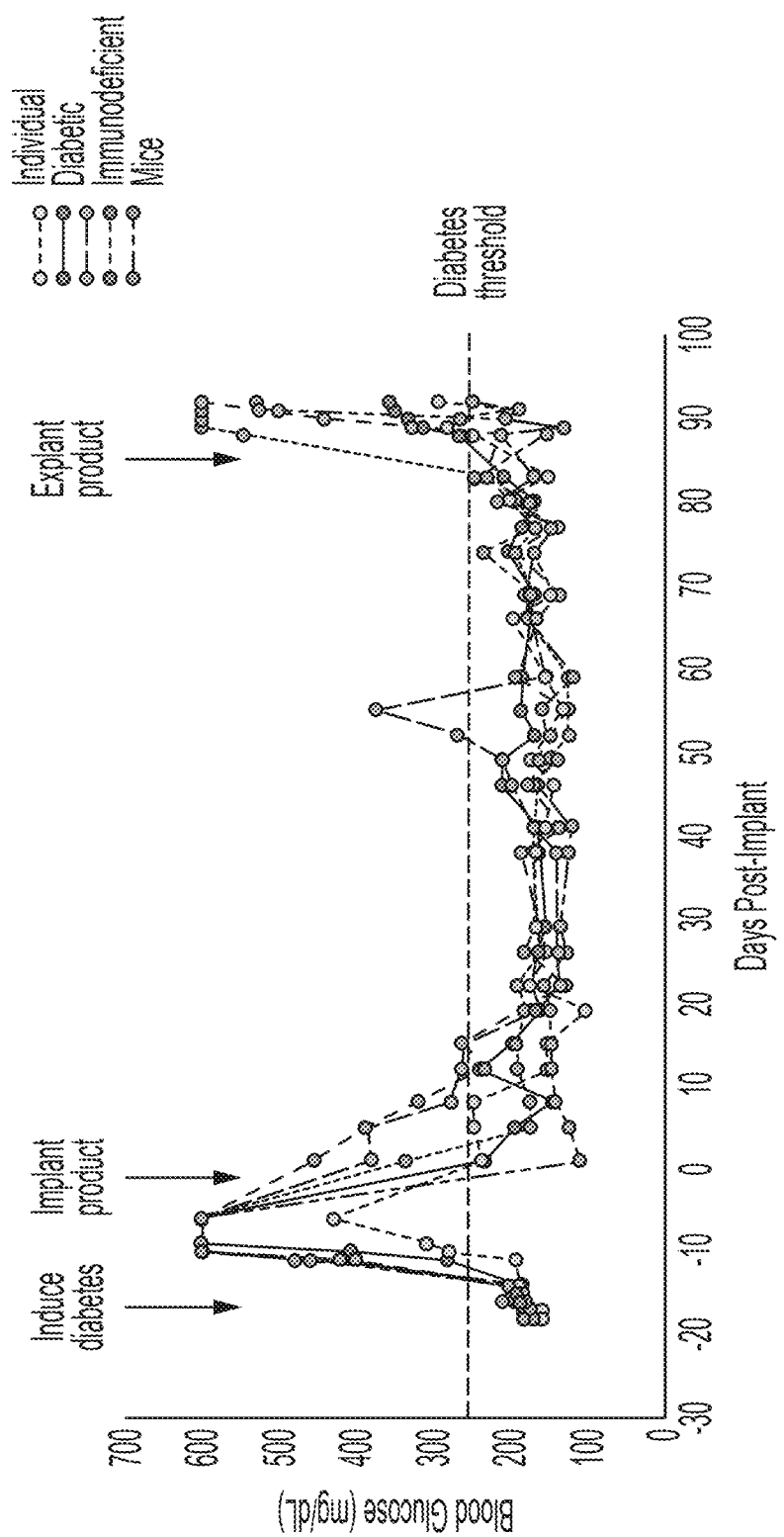
FIG. 12 depicts an example result of blood glucose level before or after SC-β cell implant, and before or after SC-β cell explant in animal models.

Encapsulated SC-β cells can cure diabetes in animal models (e.g. diabetic immunodeficient mice). As shown in FIG. 12, mice were first induced to have diabetes, encapsulated SC-β cells were then implanted into mice after inducing diabetes, and finally the SC-β cells were explanted after certain time. Blood glucose level was monitored through the whole process. After inducing diabetes, the blood glucose level went up to a level much higher than diabetes threshold. After implantation of SC-β cells, blood glucose level was dropped to below the diabetes threshold level. After explanation, the blood glucose level increased back to the high level.

Figure 14:
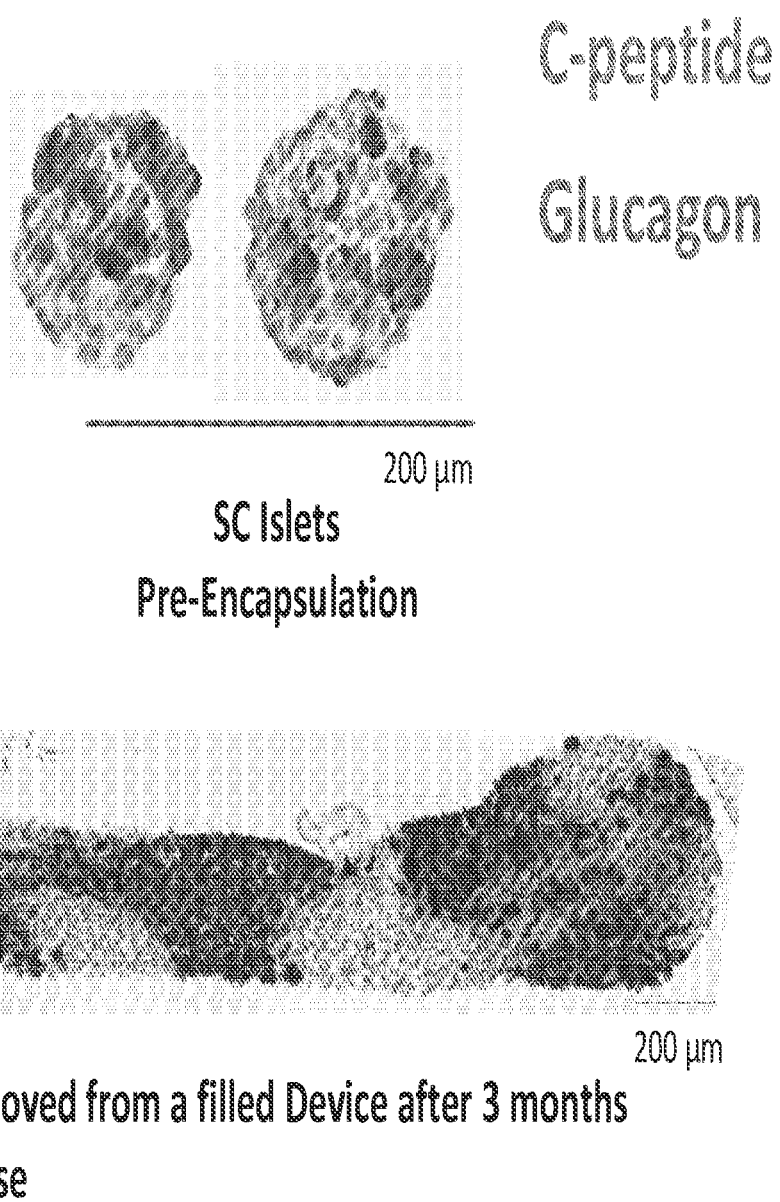
FIG. 14 depicts images of exemplary SC-islet cells before encapsulation and 3 months post-implant in a mouse.

In another example, mice were implanted with a device filled with an exemplary SC-β cell population that was developed in vitro. FIG. 14 shows an image of the in vitro developed SC islets before encapsulation of the cells in the capsule device, as well as an image of the cells that were removed from the device 3 months after implantation into a mouse. As demonstrated by the C-peptide and Glucagon immunostaining, these encapsulated SC-islets show high number of viable β cells post-implant in mice.

Example 7—Constituent Analysis of Differentiated SC-β Cells

Figure 13:
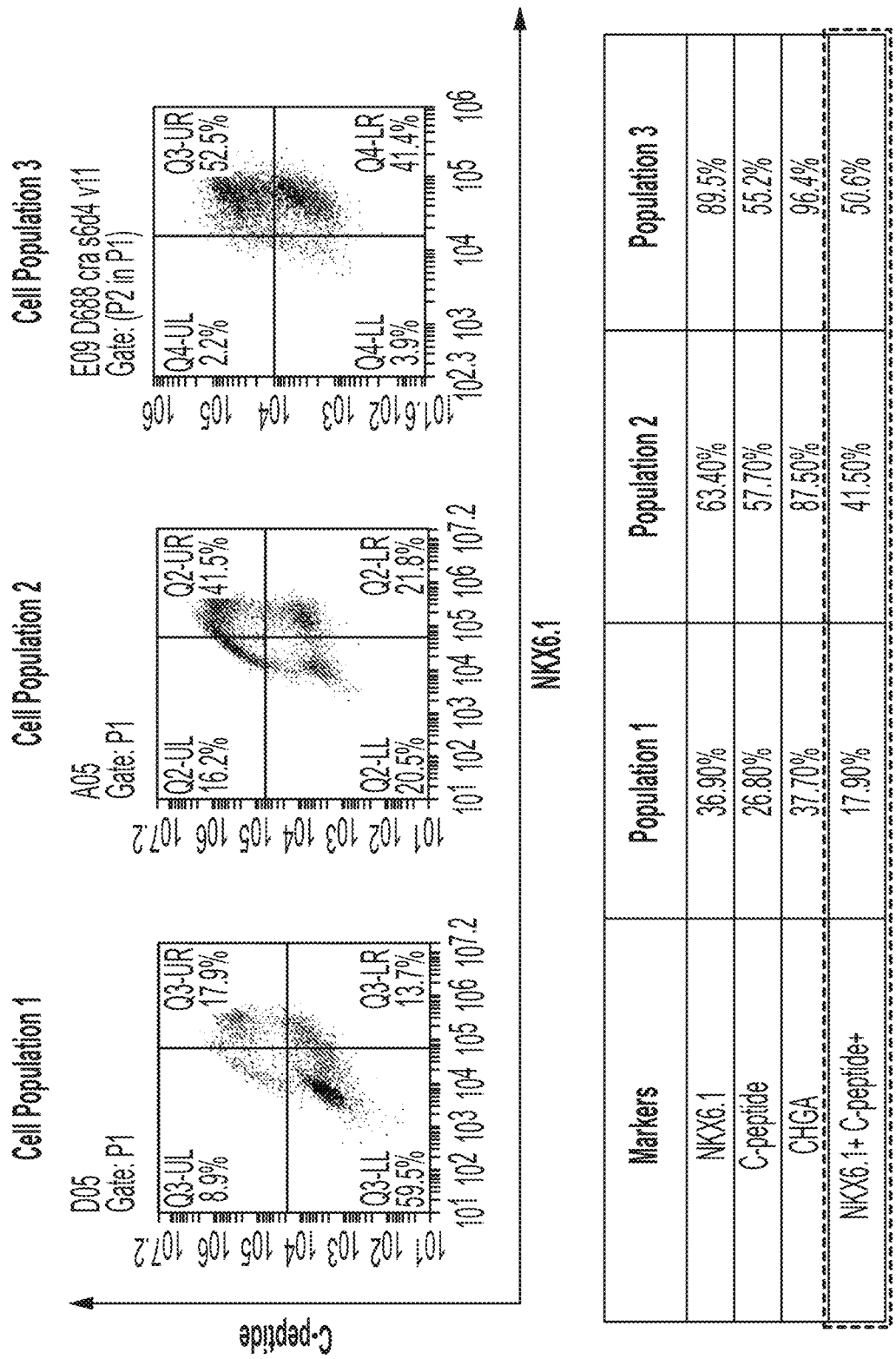
FIG. 13 depicts a comparison of exemplary differentiated cell populations.

Exemplary differentiated SC-β cell populations were examined by flow cytometry to analyze their constituents. According to some aspect of the present disclosure, three differentiated populations were generated by three different protocols, and their flow cytometry analysis results are shown in FIG. 13. Cell population 1 was generated using conventional protocol, while cell populations 2 and 3 were generated using exemplary protocols as provided herein. As shown in FIG. 13, cell populations 1, 2, and 3 are all mixtures of different cell types, as suggested by different marker expression patterns. Notably, cell population 3 had the highest β cell population (NKX6.1+/C-peptide+).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A composition comprising a population of PDX1-negative primitive gut tube cells and a BMP signaling pathway inhibitor, wherein the BMP signaling pathway inhibitor is a compound of Formula A,

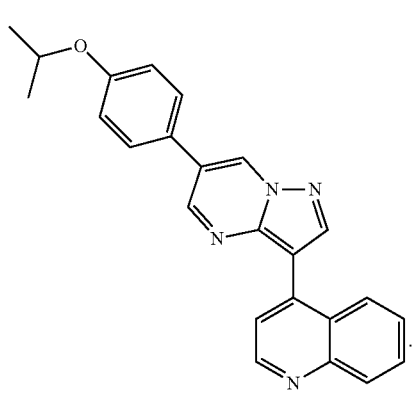

(A)

2. The composition of claim 1, wherein the composition further comprises a growth factor from the transformation growth factor β (TGF-β) superfamily.

3. The composition of claim 2, wherein the growth factor from the transformation growth factor β (TGF-β) superfamily is selected from the group consisting of an Inhibin, an Activin, a Mullerian inhibiting substance (MIS), a bone morphogenic protein (BMP), decapentaplegic (dpp), Vg-1, monoclonal nonspecific suppressor factor (MNSF), growth differentiating factor 8 (GDF8), and growth differentiating factor 11 (GDF11).

4. The composition of claim 2, wherein the growth factor from the transformation growth factor β (TGF-β) superfamily comprises Activin A.

5. The composition of claim 4, wherein the composition comprises about 2 ng/ml to about 50 ng/ml of Activin A.

6. The composition of claim 1, wherein the composition comprises about 0.1 μM to about 0.3 μM of the BMP signaling inhibitor.

7. The composition of claim 1, wherein the composition further comprises keratinocyte growth factor (KGF).

8. The composition of claim 1, wherein the composition further comprises SANT1.

9. The composition of claim 1, wherein the composition further comprises retinoic acid.

10. The composition of claim 1, wherein the composition further comprises PdbU.

11. The composition of claim 1, wherein the composition further comprises thiazovivin.

12. The composition of claim 1, wherein the composition further comprises activin A and keratinocyte growth factor (KGF).

13. The composition of claim 1, wherein the composition further comprises activin A and SANT1.

14. The composition of claim 1, wherein the composition further comprises activin A and retinoic acid.

15. The composition of claim 1, wherein the composition further comprises activin A and PdbU.

16. The composition of claim 1, wherein the composition further comprises activin A and thiazovivin.

17. The composition of claim 1, wherein the composition comprises two or more of the following: keratinocyte growth factor (KGF), SANT1, retinoic acid, PdbU, and thiazovivin.

18. The composition of claim 1, wherein the composition comprises three or more of the following: keratinocyte growth factor (KGF), SANT1, retinoic acid, PdbU, and thiazovivin.

19. The composition of claim 1, wherein the composition comprises four or more of the following: keratinocyte growth factor (KGF), SANT1, retinoic acid, PdbU, and thiazovivin.

20. The composition of claim 1, wherein the composition comprises keratinocyte growth factor (KGF), SANT1, retinoic acid, PdbU, and thiazovivin.

21. The composition of claim 17, wherein the composition comprises activin A.

22. The composition of claim 18, wherein the composition comprises activin A.

23. The composition of claim 19, wherein the composition comprises activin A.

24. The composition of claim 20, wherein the composition comprises activin A.

* * * * *

```
                       SEQUENCE LISTING

Sequence total quantity: 18
SEQ ID NO: 1            moltype = AA  length = 116
FEATURE                 Location/Qualifiers
source                  1..116
                        mol_type = protein
                        organism = Homo sapiens
SEQUENCE: 1
GLECDGKVNI CCKKQFFVSF KDIGWNDWII APSGYHANYC EGECPSHIAG TSGSSLSFHS   60
TVINHYRMRG HSPFANLKSC CVPTKLRPMS MLYYDDGQNI IKKDIQNMIV EECGCS      116

SEQ ID NO: 2            moltype = DNA  length = 351
FEATURE                 Location/Qualifiers
source                  1..351
                        mol_type = other DNA
                        organism = Homo sapiens
SEQUENCE: 2
ggcttggagt gtgatggcaa ggtcaacatc tgctgtaaga aacagttctt tgtcagtttc   60
aaggacatcg gctggaatga ctggatcatt gctccctctg gctatcatgc caactactgc  120
gagggtgagt gcccgagcca tatagcaggc acgtccgggt cctcactgtc cttccactca  180
acagtcatca accactaccg catgcggggc catgccccct ttgccaacct caaatcgtgc  240
tgtgtgccca ccaagctgag acccatgtcc atgttgtact atgatgatgg tcaaaacatc  300
atcaaaaagg acattcagaa catgatcgtg gaggagtgtg ggtgctcata g           351

SEQ ID NO: 3            moltype = AA  length = 426
FEATURE                 Location/Qualifiers
source                  1..426
                        mol_type = protein
                        organism = Homo sapiens
SEQUENCE: 3
MPLLWLRGFL LASCWIIVRS SPTPGSEGHS AAPDCPSCAL AALPKDVPNS QPEMVEAVKK   60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDTGE EAAEEVGLKGE RSELLLSEKV VDARKSTWHV FPVSSSIQRL LDQGKSSLDV  240
RIACEQCQES GASLVLLGKK KKKEEEGEGK KKGGGEGGAG ADEEKEQSHR PFLMLQARQS  300
EDHPHRRRRR GLECDGKVNI CCKKQFFVSF KDIGWNDWII APSGYHANYC EGECPSHIAG  360
TSGSSLSFHS TVINHYRMRG HSPFANLKSC CVPTKLRPMS MLYYDDGQNI IKKDIQNMIV  420
EECGCS                                                             426

SEQ ID NO: 4            moltype = AA  length = 130
FEATURE                 Location/Qualifiers
source                  1..130
                        mol_type = protein
                        organism = Homo sapiens
SEQUENCE: 4
ARQSEDHPHR RRRGLECDG KVNICCKKQF FVSFKDIGWN DWIIAPSGYH ANYCEGECPS    60
HIAGTSGSSL SFHSTVINHY RMRGHSPFAN LKSCCVPTKL RPMSMLYYDD GQNIIKKDIQ  120
NMIVEECGCS                                                         130

SEQ ID NO: 5            moltype = AA  length = 115
FEATURE                 Location/Qualifiers
source                  1..115
                        mol_type = protein
                        organism = Homo sapiens
SEQUENCE: 5
GLECDGKVNI CCKKQFFVSF KDIGWNDWII APSGYHANYC EGECPSHIAG TSGSSLSFHS   60
TVINHYACGH SPFANLKSCC VPTKLRPMSM LYYDDGQNII KKDIQNMIVE ECGCS       115

SEQ ID NO: 6            moltype = AA  length = 426
FEATURE                 Location/Qualifiers
source                  1..426
                        mol_type = protein
                        organism = Homo sapiens
SEQUENCE: 6
MPLLWLRGFL LASCWIIVRS SPTPGSEGHS AAPDCPSCAL AALPKDVPNS QPEMVEAVKK   60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDTGE EAEEVGLKGE RSELLLSEKV VDARKSTWHV FPVSSSIQRL LDQGKSSLDV  240
```

```
RIACEQCQES GASLVLLGKK KKKEEEGEGK KKGGGEGGAG ADEEKEQSHR PFLMLQARQS   300
EDHPHRRRRR GLECDGKVNI CCKKQFFVSF KDIGWNDWII APSGYHANYC EGECPSHIAG   360
TSGSSLSFHS TVINHYRMRG HSPFANLKSC CVPTKLRPMS MLYYDDGQNI IKKDIQNMIV   420
EECGCS                                                             426

SEQ ID NO: 7              moltype = AA   length = 424
FEATURE                   Location/Qualifiers
source                    1..424
                          mol_type = protein
                          organism = Mus musculus
SEQUENCE: 7
MPLLWLRGFL LASCWIIVRS SPTPGSEGHG SAPDCPSCAL ATLPKDGPNS QPEMVEAVKK   60
HILNMLHLKK RPDVTQPVPK AALLNAIRKL HVGKVGENGY VEIEDDIGRR AEMNELMEQT   120
SEIITFAESG TARKTLHFEI SKEGSDLSVV ERAEVWLFLK VPKANRTRTK VTIRLFQQQK   180
HPQGSLDTGD EAEEMGLKGE RSELLLSEKV VDARKSTWHI FPVSSSIQRL LDQGKSSLDV   240
RIACEQCQES GASLVLLGKK KKKEVDGDGK KKDGSDGGLE EEKEQSHRPF LMLQARQSED   300
HPHRRRRRGL ECDGKVNICC KKQFFVSFKD IGWNDWIIAP SGYHANYCEG ECPSHIAGTS   360
GSSLSFHSTV INHYRMRGHS PFANLKSCCV PTKLRPMSML YYDDGQNIIK KDIQNMIVEE   420
CGCS                                                               424

SEQ ID NO: 8              moltype = AA   length = 424
FEATURE                   Location/Qualifiers
source                    1..424
                          mol_type = protein
                          organism = Rattus norvegicus
SEQUENCE: 8
MPLLWLRGFL LASCWIIVRS SPTPGSEGHG AAPDCPSCAL ATLPKDGPNS QPEMVEAVKK   60
HILNMLHLKK RPDVTQPVPK AALLNAIRKL HVGKVGENGY VEIEDDIGRR AEMNELMEQT   120
SEIITFAESG TARKTLHFEI SKEGSDLSVV ERAEVWLFLK VPKANRTRTK VTIRLFQQQK   180
HPQGSLDMGD EAEEMGLKGE RSELLLSEKV VDARKSTWHI FPVSSSIQRL LDQGKSSLDV   240
RIACEQCQES GASLVLLGKK KKKEVDGDGK KKDGSDGGLE EEKEQSHRPF LMLQARQSED   300
HPHRRRRRGL ECDGKVNICC KKQFFVSFKD IGWNDWIIAP SGYHANYCEG ECPSHIAGTS   360
GSSLSFHSTV INHYRMRGHS PFANLKSCCV PTKLRPMSML YYDDGQNIIK KDIQNMIVEE   420
CGCS                                                               424

SEQ ID NO: 9              moltype = AA   length = 424
FEATURE                   Location/Qualifiers
source                    1..424
                          mol_type = protein
                          organism = Gallus gallus
SEQUENCE: 9
MPLLWKRGFL LVICWIIVRS SPTPGSEGHS SVADCPSCAL TTLSKDVPSS QPEMVEAVKK   60
HILNMLHLRD RPNITQPVPK AALLNATKKL HVGKVGDDGY VEIEDDVGRR AEMNEVVEQT   120
SEIITFAESG TPKKTLHFEI SKEGSELSVV EHAEVWLFLK VSKANRSRTK VTIRLFQQQR   180
QPKGNSEAAE DMEDMGLKGE RSETLISEKA VDARKSTWHI FPISSSVQRL LDQGQSSLDV   240
RIACDLCQET GASLVLLGKK KKKEDDGEGK EKDGGELTGE EEKEQSHRPF LMMLARHSED   300
RQHRRRERGL ECDGKVNICC KKQFFVSFKD IGWSDWIIAP TGYHANYCEE ECPSHIAGTS   360
GSSLSFHSTV INHYRMRGHS PFANLKSCCV PTKLRPMSML YYDDGQNIIK KDIQNMIVEE   420
CGCS                                                               424

SEQ ID NO: 10             moltype = AA   length = 425
FEATURE                   Location/Qualifiers
source                    1..425
                          mol_type = protein
                          organism = Bos taurus
SEQUENCE: 10
MPLLWLRGFL LASCWIIVRS SPTPGSEGHS AAPDCPSCAL ATLPKDVPNS QPEMVEAVKK   60
HILNMLHLKK RPDVTQPVPK AALLNAIRKL HVGKVGENGY VEIEDDIGRR AEMNELMEQT   120
SEIITFAESG TARKTLHFEI SKEGSDLSVV ERAEIWLFLK VPKANRTRSK VTIRLFQQQK   180
HLQGSLDAGE EAEEVGLKGE KSEMLISEKV VDARKSTWHI FPVSSCIQRL LDQGKSSLDI   240
RIACEQCQET GASLVLLGKK KKKEEEGEGK KRDGEGGAGG DEEKEQSHRP FLMLQARQSE   300
DHPHRRRRRG LECDGKVNIC CKKQFFVSFK DIGWNDWIIA PSGYHANYCE GECPSHIAGT   360
SGSSLSFHST VINHYRMRGH SPFANLKSCC VPTKLRPMSM LYYDDGQNII KKDIQNMIVE   420
ECGCS                                                              425

SEQ ID NO: 11             moltype = AA   length = 426
FEATURE                   Location/Qualifiers
source                    1..426
                          mol_type = protein
                          organism = Equus caballus
SEQUENCE: 11
MPLLWLRGFL LASCWIIVKS SPTPGSEGHS AAPNCPSCAL ATLPKDVPNA QPEMVEAVKK   60
HILNMLHLKK RPDVTQPVPK AALLNAIRKL HVGKVGENGY VEIEDDIGRR AEMNELMEQT   120
SEIITFAESG TARKTLHFEI SKEGSDLSVV ERAEVWLFLK VPKANRTRSK VTIRLLQQQK   180
HPQGSSDTRE EAEEADLMEE RSEQLISEKV VDARKSTWHI FPVSSSIQRL LDQGKSSLDI   240
RIACDQCHET GASLVLLGKK KKKEEEGEGK KKDGGEAGAG VDEEKEQSHR PFLMLQARQS   300
EDHPHRRRRR GLECDGKVNI CCKKQFFVSF KDIGWNDWII APSGYHANYC EGECPSHIAG   360
TSGSSLSFHS TVINQYRLRG HNPFANLKSC CVPTKLRPMS MLYYDDGQNI IKKDIQNMIV   420
EECGCS                                                             426
```

```
SEQ ID NO: 12              moltype = AA   length = 424
FEATURE                    Location/Qualifiers
source                     1..424
                           mol_type = protein
                           organism = Sus scrofa
SEQUENCE: 12
MPLLWLRGFL LASCWIIVRS SPTPGSGGHS AAPDCPSCAL ATLPKDVPNS QPEMVEAVKK    60
HILNMLHLKK RPDVTQPVPK AALLNAIRKL HVGKVGENGY VELEDDIGRR AEMNELMEQT   120
SEIITFAEAG TARKTLRFEI SKEGSDLSVV ERAEIWLFLK VPKANRTRTK VSIRLFQQQR   180
RPQGSADAGE EAEDVGFPEE KSEVLISEKV VDARKSTWHI FPVSSSIQRL LDQGKSALDI   240
RTACEQCHET GASLVLLGKK KKKEEEAEGR KRDGEGAGVD EEKEQSHRPF LMLQARQSEE   300
HPHRRRRRGL ECDGKVNICC KKQFFVSFKD IGWNDWIIAP SGYHANYCEG ECPSHIAGTS   360
GSSLSFHSTV INHYRMRGHS PFANLKSCCV PTKLRPMSML YYDDGQNIIK KDIQNMIVEE   420
CGCS                                                                424

SEQ ID NO: 13              moltype = AA   length = 425
FEATURE                    Location/Qualifiers
source                     1..425
                           mol_type = protein
                           organism = Ovis aries
SEQUENCE: 13
MPLLWLRGFL LASCWIIVRS SPTPGSEGHS AAPDCPSCAL ATLPKDVPNS QPEMVEAVKK    60
HILNMLHLKK RPDVTQPVPK AALLNAIRKL HVGKVGENGY VEIEDDIGRR AEMNELMEQT   120
SEIITFAESG TARKTLHFEI SQEGSDLSVV ERAEIWLFLK VPKANRTRSK VTIRLFQQQK   180
HLQGSLDAGE EAEEVGLKGE KSEMLISEKV VDARKSTWHI FPVSSCIQRL LDQGKSSLDI   240
RIACEQCQET GASLVLLGKK KRKEEEGEGK KRDGEGGAGG DEEKEQSHRP FLMLQARQSE   300
DHPHRRRRRG LECDGKVNIC CKKQFFVSFK DIGWNDWIIA PSGYHANYCE GECPSHIAGT   360
SGSSLSFHST VINHYRMRGH SPFANLKSCC VPTKLRPMSM LYYDDGQNII KKDIQNMIVE   420
ECGCS                                                               425

SEQ ID NO: 14              moltype = AA   length = 424
FEATURE                    Location/Qualifiers
source                     1..424
                           mol_type = protein
                           organism = Felis catus
SEQUENCE: 14
MPLLWLRGFL LASCWIIVRS SPTPGSEGPG AAPDCPSCAL ATLPKDVPNS QPEMVEAVKK    60
HILNMLHLKK RPEVTQPVPK AALLNAIRKL HVGKVGENGY VEIEDDIGRR AEMNELMEQT   120
SEIITFAESG TARKTLHFEI SKEGSDLSVV ERAEVWLFLK VPKANRTRTK VTIQLLQKQP   180
QGGVDAGEEA EEMGLMEERN EVLISEKVVD ARKSTWHIFP VSSSIQRLLD QGKSSLDVRI   240
ACEQCHETGA SLVLLGKKKK KEEEGEGKKK DGGDGGAGAD EDKEQSHRPF LMLQARQSED   300
HPHRRRRRGL ECDGKVNICC KKQFFVSFKD IGWNDWIIAP SGYHANYCEG ECPSHIAGTS   360
GSSLSFHSTV INHYRMRGHS PFANLKSCCV PTKLRPMSML YYDDGQNIIK KDIQNMIVEE   420
CGCS                                                                424

SEQ ID NO: 15              moltype = AA   length = 395
FEATURE                    Location/Qualifiers
source                     1..395
                           mol_type = protein
                           organism = Danio rerio
SEQUENCE: 15
MSPLPLLSGI LLLLIRSCSL SAMVTKGSLP MSEQQAGATV CPSCALARFR KGVSESEDEG    60
AQQDVVEAVK RHILNMLHLQ ERPNITHPVP RAALLNAIRK VHVGRVAKDG SVLIEDEASN   120
RAETEQAEQT EIIITFAETGE APGIVNFLIS KEGGEMSVVD QANVWIFLRL PKGNRTRANV   180
NIRLLLQQGA GEKILAEKSV DTRRSGWHTF PASESVQSLL QRGGSTLSLR VSCPLCADAR   240
ATPVLVSPGG SEREQSHRPF LMAVVRQMDE LSLRRRRKRG LECDGKARVC CKRQFYVNFK   300
DIGWNDWIIA PSGYHANYCE GDCASNVASI TGNSLSFHST VISHYRIRGY SPFTNIKSCC   360
VPTRLRAMSM LYYNEEQKIV KKDIQNMIVE ECGCS                              395

SEQ ID NO: 16              moltype = AA   length = 404
FEATURE                    Location/Qualifiers
source                     1..404
                           mol_type = protein
                           organism = Carassius auratus
SEQUENCE: 16
MSSLTLVNRG TAALRLFVRG LLTHSSREWL SGDGEPDDPV TPCPSCALAQ RQKDSEEQTD    60
MVEAVKRHIL NMLHLNTRPN VTHPVPRAAL LNAIRRLHVG RVGEDGTVEM EEDGGGLGEH   120
REQSEEQPFE IITFAEPGDA PDIMKFDISM EGNTLSVVEQ ANVWLLLKVA KGSRGKGKVS   180
VQLLQHGKAD PGSADGPQEA VVSEKTVDTR RSGWHTLPVS RTVQTLLLGD SSMLSLRVSC   240
PMCAEAGAVP ILVPTESNKG KEREQSHRPF LMVVLKPAEE HPHRRSKRGL ECDGKIRVCC   300
KRQFYVNFKD IGWSDWIIAP SGYHANYCEG DCPSHVASIT GSALSFHSTV INHYRMRGYS   360
PFNNIKSCCV PTRLRAMSML YYNEEQKIIK KDIQNMIVEE CGCS                    404

SEQ ID NO: 17              moltype = DNA   length = 425
FEATURE                    Location/Qualifiers
source                     1..425
                           mol_type = other DNA
                           organism = Homo sapiens
```

```
SEQUENCE: 17
gcccggcagt ctgaagacca ccctcatcgc cggcgtcggc ggggcttgga gtgtgatggc   60
aaggtcaaca tctgctgtaa gaaacagttc tttgtcagtt tcaaggacat cggctggaat  120
gactggatca ttgctccctc tggctatcat gccaactact gcgagggtga gtgcccgagc  180
catatagcag gcacgtccgg gtcctcactg tccttccact caacagtcat caaccactac  240
cgcatgcggg gccatagccc ctttgccaac ctcaaatcgt gctgtgtgcc caccaagctg  300
agacccatgt ccatgttgta ctatgatgat ggtcaaaaca tcatcaaaaa ggacattcag  360
aacatgatcg tggaggagtg tgggtgctca tagagttgcc cagcccaggg ggaaagggag  420
caaga                                                              425

SEQ ID NO: 18          moltype = DNA length = 348
FEATURE                Location/Qualifiers
source                 1..348
                       mol_type = other DNA
                       organism = Homo sapiens
SEQUENCE: 18
ggcctggagt gcgacggcaa ggtcaacatc tgctgtaaga aacagttctt tgtcagtttc   60
aaggacatcg gctggaatga ctggatcatt gctccctctg gctatcatgc caactactgc  120
gagggtgagt gcccgagcca tatagcaggc acgtccgggt cctcactgtc cttccactca  180
acagtcatca accactacgc atgcggccat agccccttg ccaacctcaa atcgtgctgt  240
gtgcccacca agctgagacc catgtccatg ttgtactatg atgatggtca aaacatcatc  300
aaaaaggaca ttcagaacat gatcgtggag gagtgcgggt gctcctaa              348
```